United States Patent
Busch, Jr. et al.

(10) Patent No.: US 10,827,976 B2
(45) Date of Patent: Nov. 10, 2020

(54) PRESSURE MODULATION, MOTION DETECTION, INDIVIDUALIZED GEOMETRY, AND IMPROVED OPTIC-SKIN COUPLING TO IMPROVE LONG TERM CLINICAL MONITORING WITH DIFFUSE OPTICS

(71) Applicants: The Trustees of The University of Pennsylvania, Philadelphia, PA (US); The Children's Hospital of Philadelphia, Philadelphia, PA (US)

(72) Inventors: David R. Busch, Jr., Philadelphia, PA (US); Ashwin B. Parthasarathy, West Chester, PA (US); Wesley B. Baker, Philadelphia, PA (US); Malavika Chandra, Framingham, MA (US); Rickson C. Mesquita, Campinas (BR); Daniel J. Licht, Wallingford, PA (US); Arjun G. Yodh, Merion, PA (US); Kenneth Abramson, Ardmore, PA (US)

(73) Assignees: The Trustees of the University of Pennsylvania, Philadelphia, PA (US); The Children's Hospital of Philadelphia, Philadelphia, PA (US)

( * ) Notice: Subject to any disclaimer, the term of this patent is extended or adjusted under 35 U.S.C. 154(b) by 328 days.

(21) Appl. No.: 15/120,895

(22) PCT Filed: Feb. 24, 2015

(86) PCT No.: PCT/US2015/017286
§ 371 (c)(1),
(2) Date: Aug. 23, 2016

(87) PCT Pub. No.: WO2015/127436
PCT Pub. Date: Aug. 27, 2015

(65) Prior Publication Data
US 2016/0361017 A1    Dec. 15, 2016

Related U.S. Application Data

(60) Provisional application No. 61/943,907, filed on Feb. 24, 2014, provisional application No. 62/091,064, (Continued)

(51) Int. Cl.
*A61B 5/1455*       (2006.01)
*A61B 5/00*         (2006.01)
(Continued)

(52) U.S. Cl.
CPC .......... *A61B 5/6843* (2013.01); *A61B 5/0017* (2013.01); *A61B 5/0261* (2013.01);
(Continued)

(58) Field of Classification Search
CPC . A61B 5/0059; A61B 5/1455; A61B 5/14551; A61B 5/14552; A61B 5/14553;
(Continued)

(56) References Cited

U.S. PATENT DOCUMENTS 4,321,930 A * 3/1982 Jobsis .................. A61B 5/0059
                                                         600/344
5,103,829 A * 4/1992 Suzuki ............... A61B 5/14553
                                                         600/310
(Continued)

OTHER PUBLICATIONS

Baker et al., "Modified Beer-Lambert law for blood flow", Biomedical Optics Express, Oct. 28, 2014, 5, 4053-4075.
(Continued)

*Primary Examiner* — Chu Chuan Liu
(74) *Attorney, Agent, or Firm* — BakerHostetler

(57) ABSTRACT

The present disclosure provides devices and methods for improved hemodynamic monitoring, including devices for
(Continued)

characterizing hemodynamic activity within a tissue or region of interest.

22 Claims, 31 Drawing Sheets

Related U.S. Application Data filed on Dec. 12, 2014, provisional application No. 62/091,048, filed on Dec. 12, 2014.

(51) Int. Cl.
*A61B 5/026* (2006.01)
*A61B 5/0295* (2006.01)
*A61B 5/1495* (2006.01)

(52) U.S. Cl.
CPC .......... *A61B 5/0295* (2013.01); *A61B 5/1495* (2013.01); *A61B 5/14552* (2013.01); *A61B 5/14553* (2013.01); *A61B 5/6814* (2013.01); *A61B 5/7246* (2013.01); *A61B 5/7282* (2013.01); *A61B 2560/0223* (2013.01); *A61B 2562/0238* (2013.01); *A61B 2562/0242* (2013.01); *A61B 2562/146* (2013.01)

(58) Field of Classification Search
CPC ... A61B 5/0261; A61B 5/0295; A61B 5/0017; A61B 5/1495; A61B 5/7246; A61B 5/6843; A61B 5/6814; A61B 5/7282
See application file for complete search history.

(56) References Cited

U.S. PATENT DOCUMENTS

| | | | |
|---|---|---|---|
| 5,694,931 A * | 12/1997 | Tsuchiya | A61B 5/14553 600/310 |
| 6,671,528 B2 * | 12/2003 | Steuer | A61B 5/14552 600/322 |
| 8,082,015 B2 | 12/2011 | Yodh et al. | |
| 2006/0063995 A1 | 3/2006 | Yodh et al. | |
| 2006/0074283 A1 * | 4/2006 | Henderson | A61B 5/6814 600/315 |
| 2007/0259451 A1 | 11/2007 | Heanue et al. | |
| 2007/0282182 A1 * | 12/2007 | Messerges | A61B 5/0059 600/324 |
| 2008/0188724 A1 * | 8/2008 | Hwang | A61B 5/1455 600/316 |
| 2008/0200784 A1 | 8/2008 | Cheng | |
| 2009/0099425 A1 | 4/2009 | Starr et al. | |
| 2009/0143655 A1 | 6/2009 | Shani | |
| 2009/0317856 A1 | 12/2009 | Mycek et al. | |
| 2010/0191080 A1 | 7/2010 | Mills | |
| 2010/0324390 A1 | 12/2010 | McLaughlin et al. | |
| 2012/0296178 A1 * | 11/2012 | Lamego | A61B 5/1455 600/310 |
| 2013/0023744 A1 | 1/2013 | Benni | |
| 2014/0275891 A1 * | 9/2014 | Muehlemann | A61B 5/6801 600/328 |

OTHER PUBLICATIONS

Durduran et al., "Diffuse optics for tissue monitoring and tomography", Reports on Progress in Physics, Jun. 2, 2010, 73, 076701, 43 pages.

Fabbri et al., "Optical measurements of absorption changes in two-layered diffusive media", Physics in Medicine and Biology, 2004, 49, 1183-1201.

Yodh, "Spatially varying dynamical properties of turbid media probed with diffusing temporal light correlation", Journal of the Optical Society of America A, Jan. 1997, 14, 1, 192-215.

Li et al. Simultaneous measurement of deep tissue blood flow and oxygenation using noncontact diffuse correlation spectroscopy floxoximeter Scientific Reports 3:1358 Feb. 28, 2013 pp. 1-10.

\* cited by examiner

PRESSURE MODULATION, MOTION DETECTION, INDIVIDUALIZED GEOMETRY, AND IMPROVED OPTIC-SKIN COUPLING TO IMPROVE LONG TERM CLINICAL MONITORING WITH DIFFUSE OPTICS

CROSS-REFERENCE TO RELATED APPLICATIONS

The present application is a National Stage Application filed under 35 U.S.C. 371 of International Application No. PCT/US2015/017286, filed Feb. 24, 2015, which claims priority to and the benefit of U.S. Patent Application No. 61/943,907, "Probes And Pressure Modulation Algorithms For Reducing Extratissue Contamination In Hemodynamic Measurement" (filed on Feb. 24, 2014); U.S. Patent Application No. 62/091,048, "Probes And Pressure Modulation Algorithms For Reducing Extratissue Contamination In Hemodynamic Measurement" (filed on Dec. 12, 2014); and U.S. Patent Application No. 62/091,064, "Pressure Modulation, Motion Detection, Individualized Geometry, And Improved Optic-Skin Coupling To Improve Long Term Clinical Monitoring With Diffuse Optics" (filed on Dec. 12, 2014). All of the foregoing applications are incorporated herein by reference in their entireties for any and all purposes.

GOVERNMENT SUPPORT

This invention was made with government support under grant numbers NS060653, HL007915, and EB015893 awarded by the National Institutes of Health. The government has certain rights in the invention.

TECHNICAL FIELD

The present disclosure relates to the field of spectroscopic hemodynamic monitoring.

BACKGROUND

As but one example of the importance of hemodynamic information, cerebral oxygen delivery is critical in maintaining cognitive function and in the successful development of the young brain. Cerebral blood flow is regulated to ensure sufficient oxygen delivery. However, this blood flow autoregulation may be disrupted due to illness, injury, or medical treatment; without longitudinal measurements of cerebral oxygen delivery practical for bedside measurements, clinicians must utilize proxy measurements (e.g., systemic oxygenation) to anticipate and prevent ischemic brain injury. When the assumptions underlying these proxy measurements fail, clinical interventions may be poorly chosen.

Diffuse Correlation Spectroscopy (DCS) and Diffuse Optical Spectroscopy (DOS;DOS may be considered equivalent to NIRS for purposes of this disclosure) devices have been used in the head and other organs to continuously measure blood flow, volume, and oxygenation at the bedside. Current clinical cerebral oxygenation monitoring techniques measure blood flow in large vessels (e.g., Doppler ultrasound), require transport to an imaging suite (e.g., MRI) or radioactive contrasts (e.g., PET), or are restricted to monitoring temporal trends (cerebral oximeters). Diffuse optics utilizes low power red light (non-ionizing), similar to that utilized in clinically ubiquitous pulse oximeters.

However, the clinical utility and inter-study comparisons of diffuse optics are somewhat limited by technical challenges and instrument variability, restricting widespread adoption of diffuse optical techniques. Thus, there is a long-felt need in the art for improved devices and methods for collecting and monitoring hemodynamic information in body tissues, including blood flow, volume, and oxygenation, as well as other data of interest.

SUMMARY

Provided herein are, inter alia, technical advances that reduce intermeasurement and subject variability while permitting longitudinal measurements. One advance provided herein is the control and modulation of pressure applied to a patient's anatomy by an optical probe, accomplished by utilizing the pressure-dependent portion of the diffuse optical to separate signals from tissue (e.g., brain) and extratissue (e.g., extra-cerebral) signals. Non-invasive diffuse optics instruments measure optical signals that are influenced by hemodynamic contributions from the tissue (brain, cerebral region) but also the region exterior to that tissue (e.g., scalp and skull, extra-cerebral region). To improve treatment management with DCS (e.g., for stroke), it is desirable for DCS to accurately isolate and monitor blood flow changes in real time, e.g., U.S. Pat. No. 8,082,015 (Yodh et al.), incorporated herein by reference in its entirety for any and all purposes.

One may achieve real time monitoring with DCS (and/or with DOS) when the tissue in question (e.g., the head) is simplistically approximated as a semi-infinite homogeneous medium. This model, however, ignores differences between blood flow outside of the tissue (e.g., in the scalp and skull in the case of monitoring blood flow within the head) and blood flow in the tissue of interest.

In the illustrative example of cerebral blood flow, blood flow in the scalp and skull especially can affect the DCS (and/or DOS) signal, which in turn can lead experimenters to incorrectly assign physiological responses to deeper brain tissue. Further, inconsistent pressure applied on the head as the probe is being fastened can significantly alter the results of a DCS blood flow measurement. The pressure applied on the scalp directly affects the blood flow in the extra-cerebral region. When used with simplified homogeneous brain models, these measurements cannot be compared across patients and studies without an accurate measurement of the probe pressure. It should be understood, however, that the example of cerebral blood flow is illustrative only, as the disclosed methods and devices are not necessarily limited to use in cerebral studies. For example, the disclosed technologies may be used to collect, monitor, and analyze hemodynamic information from various body tissues, including the brain, the breast, muscle, joints, tumors, internal organs, and the like It should be understood that the disclosed devices and methods may be applied to DCS, DOS/NIRS, or any combination thereof. Where this disclosure mentions DCS, it should also be understood that the disclosed technology may in some embodiments also perform DOS measurement with the DCS measurement (or even in place of the DCS measurement). Likewise, where this disclosure mentions DOS, it should also be understood that the disclosed technology may in some embodiments also perform DCS measurement with the DOS measurement (or even in place of the DOS measurement) should the user decide to do so. It should further be understood that where the term "blood flow" is mentioned, the term is illustrative only and is intended to illustrate but one of several hemodynamic quantities that may be measured and/or evaluated. Thus, where the term "blood flow" is mentioned, the present disclosure also contemplates one or more of blood flow, blood volume and saturation.

There is hence a clear need to monitor the probe pressure in a standardized manner and as well as develop methods to remove the effects of blood flow from the extra cerebral components of the brain.

The present disclosure provides using pressure elements with optical probes, e.g., using an air bladder to control applied pressure as well as an element to sense the applied pressure. Algorithms may be used to isolate blood flow contributions from the tissue of interest.

Turning again to the non-limiting example of cerebral blood flow, one may use algorithms to isolate the cerebral blood flow contributions from the cortex from DCS (i.e., DCS and/or DOS) data using measurements at multiple pressures and optical source-detector separations. Pressure on the scalp may affect the blood flow in the extra-cerebral region.

For this reason, one may modulate pressure with an air bladder to permit continuous variation of the pressure applied to the skin, permitting continuous slow time scale (e.g., about 1-3 sec to about 10 min) modulation of the superficial blood flow and volume. Such modulation imposes a carrier wave on the superficial signal, but not affect the cerebral signal, and thus permit separation of cerebral blood flow. Again, the disclosed techniques are not limited to cerebral applications or the use of any particular device to modulate pressure, as the foregoing example is illustrative only.

Regarding the illustrative application to cerebral blood flow, the optical techniques of diffuse correlation spectroscopy (DCS) and diffuse optical spectroscopy are a noninvasive bedside, continuous, safe monitors of hemodynamics, e.g., cerebral blood flow (CBF) that improves individual patient management of stroke treatment as well as other brain diseases. To improve stroke treatment management with DCS and/or DOS, it is desirable to accurately monitor hemodynamics (e.g., cerebral blood flow changes) in real time. One may achieve real time monitoring with DCS/DOS by approximating the head as a semi-infinite homogeneous medium, i.e., the tissue is assumed to have spatially uniform blood flow over the sampled volume. One drawback of this model, however, is that it ignores differences between extracerebral blood flow (e.g., in the scalp and skull) and cerebral blood flow. Blood flow in the scalp and skull can affect the DCS signal and can lead experimenters to incorrectly assign physiological responses. Thus, a need for translation of DCS into the stroke clinic is a method for quickly removing extracerebral contamination in DCS cortical signals.

To handle heterogeneities in superficial (e.g., extra-cerebral) tissues, more complex, computationally intensive models have been proposed, including layered diffusion models and Monte Carlo techniques in realistic geometries of the head and other parts of the anatomy. But the complexity of these models generally makes it impractical to implement them for real time measurements of cerebral blood flow. Further, these models often require a priori anatomical information about the patient, which information may not always be available.

In one aspect, the present disclosure provides algorithms to reduce extracerebral contamination in DCS/DOS measurements of the brain in real time by acquiring DCS measurements of the head at multiple probe pressures and source-detector separations. Variations in the probe pressure against the head induce variations in extracerebral blood flow while cerebral blood flow remains constant, which permits the derivation of patient-specific analysis parameters to isolate cerebral blood flow signals. As explained below, this technique does not require a priori anatomical information, and is not limited to cerebral applications. Further, pressure is but one perturbation that a use might use to isolate tissue (e.g., cerebral) blood from superficial (e.g., extracerebral) blood flow and/or volume.

With specific regard to one non-limiting cerebral application to which one may put the disclosed technology, to reduce extracerebral contamination in cortical DCS/DOS measurements, an algorithm may use "initial" DCS/DOS measurements of the head at two (or more) different probe pressures against the scalp. One may demonstrate that increased probe pressure on the head induces decreases in scalp flow, but not cerebral flow. Hence, one way to remove extracerebral contamination is to apply a probe pressure high enough to reduce extracerebral blood flow to zero. Although this ensures that DCS/DOS does not measure blood flow in the scalp, probe pressure required to eliminate extracerebral blood flow may in some cases be too high for long term clinical monitoring. The disclosed approaches also use probe pressure to remove extra-tissue (e.g., extracerebral) contamination. However, instead of relying on one source-detector separation at a very high pressure, this approach uses two separations at two different pressures that are both low enough to be acceptable for clinical monitoring. It should be further understood that three, four, or more separations may be used at one, two, three, four, or more pressures.

The schematic in the left panel of exemplary, non-limiting FIG. 1 shows an illustrative instrument configuration that noninvasively probes the head with short and long source-detector separations: $\rho_s \sim 0.5$ cm and $\rho_l \sim 2.5$ cm. To distinguish extracerebral flow from cerebral flow, the head may be modeled as a two-layer medium (scalp+skull and brain), although the anatomy is considerably more complex. Source-detector separations may be chosen such that detected light from the long separation interrogates both layers, but detected light from the short separation is almost exclusively sensitive to the extracerebral layer. The specific source-detector separations are chosen based on subject anatomy, e.g., a neonate has a thinner skull+scalp layer than adults and requires appropriately scaled interfaces.

One may extend the Modified Beer Lambert Law to the DCS measurement. This formulation is particularly convenient in separating superficial and deep (e.g., skull/scalp and brain) DCS flow signals through a perturbation which changes blood flow in the superficial tissue, but not the deep tissue. In the following non-limiting example, we describe application of external force to the tissue-optical interface to reduce blood flow in the scalp without effecting the brain. Formally, this extension is derived by truncating the Taylor series expansion of the logarithm of the electric field autocorrelation function at monitoring time point t, delay time $\tau$, source-detector separation $\rho_l$, and probe pressure P (i.e., log $g_1(t,\tau,\rho_l,P)$) to first order:

$$-\log\left(\frac{g_1(t, \tau, \rho_l, P)}{g_{1,0}(\tau, \rho_l, P_0)}\right) \approx -\frac{\partial}{\partial F_{ec}}[\log g_{1,0}(\tau, \rho_l, P)]\Delta F_{ec}(t, P) - \quad (1)$$

$$\frac{\partial}{\partial F_c}[\log g_{1,0}(\tau, \rho_l, P)]\Delta F_c(t) =$$

$$L_{ec}(\tau, \rho_l, P_0)\Delta F_{ec}(t, P) + L_c(\tau, \rho_l, P_0)\Delta F_c(t)$$

Here, $g_{1,0}(\tau,\rho_l,P_0)$ is the "baseline" (i.e., t=0, P=P$_0$) measured electric field autocorrelation function when the extracerebral and cerebral DCS flow indices are $F_{ec,0}(P_0)$ and $F_{c,0}$, respectively. The multiplicative factors $L_{ec}(\tau,\rho_l,P_0)$ and $L_c(\tau,\rho_l,P_0)$ are DCS analogues to the partial differential pathlengths in the Modified Beer Lambert law. The temporal changes in extracerebral and cerebral flows from baseline are denoted by $\Delta F_{ec}(t,P) \equiv F_{ec}(t,P) - F_{ec,0}(P_0)$ and $\Delta F_c(t,P) \equiv F_c(t) - F_{c,0}$, respectively.

One may be interested in temporal cerebral blood flow changes ($\sim \Delta F_c(t)$), for example, prior to, during, and following clinical interventions. Because Equation 1 is linear, it can be solved quickly for real time display of these changes. However, in order to utilize Equation 1 to extract $\Delta F_c(t)$ from the measured field autocorrelation function, one may require knowledge of $L_{ec}$, $L_c$, and $\Delta F_{ec}$. As illustrated in the right panel of FIG. 1 and also in FIG. 3, the semi-infinite model can be accurately applied to DCS measurements at the short source-detector separation to extract $\Delta F_{ec}$ from $g_1(t,\tau,\rho_s,P)$ and $g_{1,0}(\tau,\rho_s,P_0)$.

As outlined in FIG. 1, a semi-infinite solution is fit to data collected at the short source-detector separation to provide $F_{ec,0}$, $F_{ec,P}$, and these quantities are utilized as inputs to a two-layer model fit simultaneously to two correlation curves acquired at different probe pressures at the long source-detector separation for the extracerebral layer thickness, d, and $F_{c,0}$. The two layer correlation diffusion equation solution is used to evaluate the partial derivatives in Equation 1 to obtain $L_{ec}$ and $L_c$. It should again be understood that although the foregoing discussion is focused on cerebral applications, the disclosed techniques may be generalized and applied to essentially any patient tissue. It should also be understood that a tissue being studied may be modeled as having two, three, four, or even more layers. Likewise, it should be understood that measurements may be made at one, two, three, or more pressures.

Another advance is integrated diffuse optic sensors. Traditionally, DCS and DOS measurements are carried out with rigid or semi-rigid probes using a 'one size fits most' paradigm. But implementing this paradigm is difficult because of the differences in anatomy (e.g., head) curvatures between neonates and adults or even between locations on the adult head. Rigid flat probes are only useful in certain anatomies and locations. Semi-flexible probes, which can be forced to conform to the head or other parts of a patient's anatomy, are widely used, but are not stable for long-term measurements and may cause pressure sores. In highly unstable or delicate patients, the pressure required to deform the probe may be clinically unsafe. Furthermore, the flexibility of these semi-rigid probes is usually at the expense of changes in source detector separation, which causes increased uncertainty of the measured hemodynamic values. A change in source-detector separation of only about 0.5 mm can result in changes in detected signal and calculated physiological properties. Flexible flat probes must be forced into conformation with the head or other anatomy, potentially leaving air gaps between probe and skin, reducing measurement signal to noise ratio.

There is thus a need for probes that maintain contact with the skin and retain original source detector separations. One may address this challenge with integrated paradigm for optical sensors that begins with anatomical imaging (e.g., head MRI, limb MRI), utilizes 3D printing to produce a mold matching the curvature of a particular location on a specific subject's anatomy (e.g., head), and produces a curved semi rigid probe that conforms well to the subject. Furthermore, one may insert non-stretchable mesh into probes to permit flexibility without changing the source-detector separations. An individually customized probe will enhance both data quality and patient comfort while permitting long-term serial monitoring over days or weeks.

Accordingly, in one aspect the present disclosure provides methods. These methods include measuring a motion of moving scattering particles in a subject's cerebral region, the measuring comprising illuminating the cerebral region and collecting illumination with a first source-detector pair and with a second source-detector pair, the source and detector of the first pair being separated by (a) a first distance and the source and detector of the second pair being separated by (b) a second distance. The pressures applied to the subject's cerebral region at or proximate to the locations of the first source and the second source are suitably different from one another, and one or both of the pressures is suitably applied to as to induce variations in superficial hemodynamics. One may isolate a deeper hemodynamic signal from the collected illumination. By hemodynamics is meant a characteristic of blood, e.g., flow, volume, pulsatility, oxygenation, viscosity, and other data of interest. The techniques described here also permit improved measurement of concentration of other endogenous chromophores (e.g., cytochrome c oxidase, lipid, water); measurements of contrast agents, with fluorescence, absorption, bioluminescence, or phosphorescence; and serial measurements over days to months of therapy (e.g., monitoring chemotherapy efficacy).

Other methods provided herein include measuring a motion of moving scattering particles in a subject's tissue, the measuring comprising illuminating the tissue and collecting illumination from a first source-detector pair and with a second source-detector pair, the source and detector of the first pair being separated by (a) a first distance and the source and detector of the second pair being separated by (b) a second distance, the pressures applied to the subject's tissue at or proximate to the locations of the first source and the second source being different from one another, one or both of the pressures being applied to as to induce variations in tissue hemodynamics, and isolating a tissue hemodynamic signal from the collected illumination. As explained elsewhere herein, one may use source-detector pairs separated by two, three, or more separation distances.

Also provided are devices, comprising: a first illumination source-detector pair, the source and detector being separated by a first distance (a); a second illumination source-detector pair, the source and detector being separated by a second distance (b); and an element configured to apply a pressure between the device and the subject's body. As described elsewhere herein, these devices may further include an accelerometer or other motion sensor element.

Also provided are methods. The methods comprise measuring moving particles in a tissue, the measuring comprising illuminating a first tissue region and illuminating a second tissue region superficial to the first tissue region; with a first source-detector pair and with a second source-detector pair, collecting illumination scattered by the particles, the source and detector of the first source-detector pair being separated by a first distance, the source and detector of the second source-detector pair being separated by a second distance, the second distance being greater than the first distance, the collecting being performed under application of (a) one or more perturbations directed to the second tissue region, (b) one or more perturbations proximate to the location of the first source-detector pair, proximate to the second source source-detector pair, or proximate to both the first and second source-detector pairs, or (c) any combination of (a) and (b), at least one perturbation effecting a hemodynamic change in the second tissue region, and estimating a blood flow of the first tissue region from the collected illumination.

Further provided are systems, the systems suitably comprising a first illumination source-detector pair having a source and detector separated by a first distance (a); a second illumination source-detector pair having a source and detector separated by a second distance (b), distances (a) and (b) being different from one another; an element configured to apply a pressure between the device and the subject's body; a processor configured to estimate a tissue's blood flow from illumination collected by at least one of the source-detector pairs.

Other methods include estimating a cerebral blood flow, comprising formulating a first estimate of extracerebral blood flow; perturbing extracerebral tissue; formulating a second estimate of extracerebral blood flow related to the perturbation of extracerebral tissue; and formulating a final estimate of cerebral blood flow related at least in part to the first and second estimates of extracerebral blood flow.

Still other methods disclosed herein include methods of monitoring a blood flow, comprising illuminating a tissue and a region superficial to the tissue; modulating one or more pressures applied to the region superficial to the tissue; collecting a blood flow signal related to illumination reflected by the tissue and to illumination reflected by the region superficial to the tissue; and removing from the signal at least a portion of the illumination reflected by the region superficial to the tissue.

BRIEF DESCRIPTION OF THE DRAWINGS

The file of this patent or patent application contains at least one drawing/photograph executed in color. Copies of this patent or patent application with color drawing(s)/photograph(s) will be provided by the Office upon request and payment of the necessary fee. The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
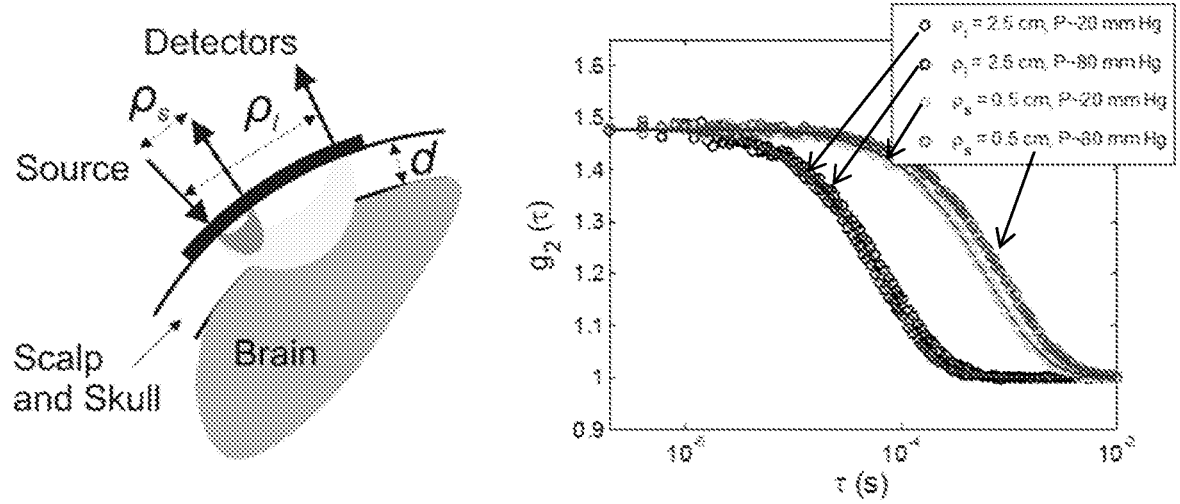
FIG. 1. Two exemplary source-detector pairs (with separations $\rho_l$ and $\rho_s$) sample tissue volumes as schematically indicated by the so-called "banana patterns" of photon propagation (left). The head is modelled as two-layer medium. The extracerebral top layer has a thickness d and DCS flow index $F_{ec}$, while the cerebral bottom layer (brain) has a DCS flow index $F_c$. Note that $F_{ec}$ depends on the probe pressure P against the scalp, but $F_c$ does not. Simulated DCS data of the head at two probe pressures (right) were generated from two-layer solutions of the correlation diffusion equation calculated with a top layer thickness of d=0.9 cm and cerebral and extracerebral optical properties and blood flow levels representative of the brain and scalp at these two probe pressures. Noise was added to the simulated data using a correlation noise model. The semi-infinite model was fit to the simulated data at the short separation, $\rho_s$, to accurately extract $F_{ec}$ at both probe pressures. These extracerebral flow indices were then used as inputs in a two layer model to simultaneously fit both correlation curves at the long separation, $\rho_l$, for d and $F_c$. The solid lines in the right panel are these fits to the data, and the recovered fitted parameters, d=0.91 cm and $F_c=1.12 \cdot 10^{-8}$ cm$^2$/s, agree well with the actual parameters, d=0.90 cm and $F_c=1.10 \cdot 10^{-8}$ cm$^2$/s.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value.

Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

Exemplary Methods

One application of the disclosed methods is developing and translating the optical technique of diffuse correlation spectroscopy (DCS) for continuous bedside monitoring of cerebral blood flow (CBF) in patients with brain disorders. This information provides clinicians with objective evidence about treatment need and efficacy.

In the illustrative but non-limiting example of patients with acute ischemic stroke, treatments are designed to maximize CBF in the brain region affected by the stroke in order to minimize stroke-related neurological damage. Doctors can prescribe many different interventions designed to increase CBF (e.g., hypertensive therapy, intravenous hydration, rtPA infusion) in stroke patients. However, each of these interventions has negative side effects and may not be effective (i.e., increase CBF in the ischemic stroke lesion) for an individual patient.

Continuous real-time monitoring of CBF over the ischemic stroke lesion permits the rapid assessment of the efficacy of a particular treatment intervention. If doctors observe that a prescribed treatment is not increasing CBF, then they can quickly test the CBF response to alternative treatments. In this way, CBF monitoring will substantially help clinicians optimize ischemic stroke treatment for each individual patient.

Due to the lack of tools available for noninvasive bedside monitoring of CBF, doctors currently must make decisions about treatment interventions empirically, based on expectations of neurological deficits, or in response to clinical deterioration. But changes in patient symptoms associated with the development of neurological deficits occur on a slower time scale than changes in CBF from a prescribed treatment intervention.

By the time patients are on an ineffective treatment paradigm exhibit deteriorating neurological symptoms, it may be too late to successfully administer alternative treatment. Thus, the detection of CBF changes before patients exhibit new symptoms is clinically valuable, because it is in this time window that the situation is most treatable.

The optical technique of diffuse correlation spectroscopy (DCS) is useful as a noninvasive bedside, continuous, safe monitor of CBF that improves individual patient management of stroke treatment as well as other brain diseases. To improve stroke treatment management with DCS, it is highly desirable for DCS/DOS to accurately monitor cerebral blood flow changes in real time.

Additionally, one may utilize diffuse optical spectroscopy (DOS) to measure tissue absorption and scattering and thence derive the concentration of physiologically important chromophores (e.g., oxy- and deoxy-hemoglobin). Together, DOS and DCS permit calculation of tissue oxygen metabolism.

One may achieve real time monitoring with DOS or DCS by approximating the head as a semi-infinite homogeneous medium, i.e., the tissue is assumed to have spatially uniform blood flow/volume/saturation over the sampled volume. One drawback of this model, however, is that it ignores differences between extracerebral (e.g., in the scalp and skull) and cerebral hemodynamics. Blood flow in the scalp and skull can affect the DCS signal and can lead experimenters to incorrectly assign physiological responses in cerebral blood flow (CBF). It should be understood that one may extend these techniques to other parts of the anatomy besides the head, e.g., the breast, internal organs, and the like, especially where a relatively pliable layer overlays a stiff layer.

To handle extracerebral heterogeneities, more complex, computationally intensive models have been proposed, including layered diffusion models and Monte Carlo techniques in realistic geometries of the head. But the complexity of these models generally makes it impractical to implement them for real time measurements of cerebral hemodynamics. Further, these models may require a priori anatomical information about the patient's head which may not always be available. Thus, one need for translation of DOS and DCS into the stroke clinic is a method for removing extracerebral contamination optical measurements, both to permit real-time flow monitoring and to improve the fidelity of the cortical signals.

Provided is a novel algorithm to remove extra-tissue (e.g., extracerebral) contamination in DCS/DOS measurements in real time by acquiring DCS/DOS measurements (e.g., of the head) at multiple probe pressures and source-detector separations. Variations in the probe pressure against the head induce variations in extra-tissue (e.g., extracerebral) blood flow while tissue (e.g., cerebral) blood flow remains constant, which permits the derivation of patient-specific analysis parameters to isolate tissue (e.g., cerebral) blood flow signals. As explained in detail in the next section, this technique does not require a priori anatomical information.

Provided herein are exemplary measurement/analysis technique that should substantially improve data collection and interpretation. In some embodiments, the technology removes extratissue contamination in DOS or DCS measurements by employing DOS or DCS data collected from two source-detector separations at two low probe pressures. The disclosed approach uses two separations at two different pressures that are both low enough to be acceptable for clinical monitoring.

The schematic in FIG. 1 shows an instrument configuration that noninvasively probes the head with short and long source-detector separations: ~0.5 cm and ~2.5 cm. To distinguish extra-cerebral from cerebral hemodynamics, the head is modeled as a two-layer medium.

Source-detector separations may be chosen such that detected light from the long separation interrogates both layers, but detected light from the shorter separation is almost exclusively sensitive to the extracerebral layer.

As explained elsewhere herein, to relate temporal changes in extracerebral flow and cerebral flow to the temporal changes in the measured DCS signal at the long separation, one may extend the so called partial pathlength version of the Modified Beer Lambert Law to DCS measurements. This procedure takes into account the contamination of the underlying cerebral signal by the superficial scalp blood flow, but can be applied to other parts of a patient's anatomy and is not limited to the head or cerebral applications.

DOS or DCS measurements at the short source-detector separation ($p_s$) reveal $\Delta F_{ec}(\tau)$, and since the short separation only samples the scalp, it is reasonable to apply the semi-infinite model to accurately extract superficial hemodynamics. Together, the measurements permit deconvolution of the clinically important cerebral blood flow from the less important and highly variable scalp dynamics.

Provided below is an illustrative step-by-step procedure for DCS monitoring of changes in cerebral blood flow due to treatment interventions. This procedure may be extended to other parts of the body besides the head and to models incorporating additional layers:

Patient-Specific DCS Measurement of Extra-Cerebral Blood Flow:
1. Acquire $g_1(t_p,\tau,\rho_l,P)$, $g_1(t_p,\tau,\rho_s,P)$, $g_{1,G}(\tau,\rho_l,P_0)$, and $g_{1,g}(\tau,\rho_s, P_0)$, the steady state field autocorrelation function measurements of the patient's head for the long ($\rho_l$) and ($\rho_s$) source-detector separations at the baseline probe pressure $P_0$ and a different probe pressure $P$ (exerted at time $t_p$).
2. Determine the pressure induced extracerebral flow change (i.e., $\Delta F_{ec,P} \equiv F_{ec}(t_p,P) - F_{ec,0}(P_0)$) by using the semi-infinite DCS approximation to extract the extracerebral flow indices $F_{ec,0}(P_0)$ and $F_{ec}(t_p,P)$ from the short source-detector separation field autocorrelation functions $g_{1,0}(\tau,\rho_s,P_0)$ and $g_1(t_p,\tau,\rho_s,P)$, respectively.
3. Via Equation 1, calculate $$L_{ec}(\tau, \rho_l, P_0) = -\frac{1}{\Delta F_{ec,p}} \log(g_1(t_P, \tau, \rho_l, P)/g_{1,0}(\tau, \rho_l, P_0)).$$

4. Simultaneously fit $g_{1,0}(\tau,\rho_l,P_0)$ and $g_1(t_p,\tau\rho_l,P)$ to the full two layer DCS diffusion model (Gagnon et al., Opt. Expr., 2008) in order to extract the baseline cerebral flow index ($F_{b,0}$) and the extracerebral layer thickness (L). Inputs in this fit will be $F_{ec}(t_p,P)$ and $F_{ec,0}(P_0)$ determined from step 2. Often, the thickness L is already known for the patient (e.g., from an MRI scan), which constrains this fit further.
5. Evaluate $$L_b(\tau, \rho_l, P_0) \equiv -\frac{\partial}{\partial F_b}[\log g_{1,0}(\tau, \rho_l, P_0)]$$

from the two layer DCS diffusion model's analytical expression for $g_{1,0}$. Required inputs in this evaluation are $F_{ec,0}(P_0)$, $F_{b,0}$, and l.

Real Time Cerebral Blood Flow Monitoring with DCS:
6. Administer desired treatment interventions to patient and continually measure the field autocorrelation functions $g_1(t,\tau,\rho_l,P)$ and $g_1(t,\tau,\rho_s,P)$.
7. As in step 2, extract the extracerebral flow index $F_{ec}(t,P)$ from the short separation autocorrelation function $g_1(t,\tau,\rho_s,P)$.
8. Given the inputs $F_{b,0}$ (step 4), $L_b(\tau,\rho_l,P_0)$ (step 5), $L_{ec}(\tau,\rho_l,P_0)$ (step 3), $g_{1,0}(\tau,\rho_l,P_0)$ (step 1), $g_1(t,\tau,\rho_l,P)$ (step 6), and $\Delta F_{ec}(t,P) \equiv F_{ec}(t,P) - F_{ec,0}(P_0)$ (steps 7 and 2), solve Equation 1 for the fractional cerebral blood flow change from baseline:

$$rCBF(t) \equiv \frac{\Delta F_b(t)}{F_{b,0}} = \qquad (2)$$

$$-\frac{1}{F_{b,0}L_b(\tau, \rho_l, P_0)} \left( \log\left(\frac{g_1(t, \tau, \rho_l, P)}{g_{1,0}(\tau, \rho_l, P_0)}\right) + L_{ec}(\tau, \rho_l, P_0)\Delta F_{ec}(t, P) \right).$$

Equation 2 assumes that changes in the electric field autocorrelation function, $g_1(\tau,\rho_l)$, are dominantly due to blood flow changes, and that these blood flow changes are also small enough for the first order Taylor series expansion in Equation 1 to be a reasonable approximation. Simulations how that Equation 1 accurately calculates cerebral flow changes (i.e., within 5% of actual) for the actual range of changes between −50% and 100%.

The fit in step 7 above may be further constrained by acquiring correlation curves at multiple probe pressures, and incrementally modifying the superficial blood flow; different pressures may each give a different autocorrelation function with the same baseline cerebral flow index. As discussed below, mechanical control of the probe pressure permits continuous variation of the pressure-dependent signal, effectively superimposing a carrier wave on the superficial signal.

One may measure absorption changes with diffuse optical spectroscopy (DOS). The Modified Beer Lambert law for the photon fluence rate is the DOS analogue of Equation 1. Thus, an analogous procedure to steps 1-8 above can be applied to extract extracerebral and cerebral absorption changes from DOS fluence rate measurements. It is straightforward to incorporate diffuse optical spectroscopy measurements of absorption changes into Equation 2 by including two additional terms in the Taylor series expansion in Equation 1:

$L_{\mu_a,ec}(\tau,\rho_l,P_0)\Delta\mu_{a,ec}(t,P)$ and $L_{\mu_a,b}(\Sigma,\rho_l,P_0)\Delta\mu_{a,b}(t)$. Here, $\Delta\mu_{a,ec}$ and $\Delta\mu_{a,b}$ are changes in extracerebral and cerebral absorption, respectively, and $$L_{\mu_a,ec} = -\frac{\partial}{\partial \mu_{a,ec}}[\log g_{1,0}(\tau, \rho_l, P_0)] \text{ and}$$

$$L_{\mu_a,b} = -\frac{\partial}{\partial \mu_{a,ec}}[\log g_{1,0}(\tau, \rho_l, P_0)]$$

are DCS partial absorption path lengths that can be evaluated analytically in the same way as described in step 5 above. The correction to Equation 2 accounting for absorption changes is $$rCBF(t) = \qquad (3)$$

$$-\frac{1}{F_{b,0}L_b(\tau, \rho_l, P_0)} \Bigg( \log\left(\frac{g_1(t, \tau, \rho_l, P)}{g_{1,0}(\tau, \rho_l, P_0)}\right) + L_{ec}(\tau, \rho_l, P_0)\Delta F_{ec}(t, P) +$$

$$L_{\mu_a,b}(\tau, \rho_l, P_0)\Delta\mu_{a,b}(t) + L_{\mu_a,ec}(\tau, \rho_l, P_0)\Delta\mu_{a,ec}(t, P) \Bigg).$$

An alternative formulation of the DCS Modified Beer-Lambert law for blood flow uses the intensity autocorrelation function, i.e., $g_2(\tau,\rho) \equiv \langle I(t,\rho)I(t+\tau,\rho)\rangle / \langle(I(t,\rho))^2\rangle$, where $I(t,\rho)$ is the detected light intensity at time t and source-detector separation $\rho$. Assuming constant tissue optical properties, the two-layer DCS Modified Beer-lambert law relates changes in a DCS optical density, $\Delta OD_{DCS}$, to changes in cerebral flow and extra-cerebral flow:

$$\Delta OD_{DCS} \equiv -\log\left[\frac{g_2(\tau, \rho) - 1}{g_2^0(\tau, \rho) - 1}\right] = d_c(\tau, \rho)\Delta F_c + d_{ec}(\tau, \rho)\Delta F_{ec}.$$

Here, $g_2(\tau,\rho)$ is the measured autocorrelation function with cerebral and extra-cerebral flow indices of $F_c$ and $F_{ec}$, respectively, and $g_2^0(\tau,\rho)$ is the "baseline" measured autocorrelation function with cerebral and extra-cerebral flow indices of $F_c^0$ and $F_{ec}^0$. The differential changes in cerebral and extra-cerebral flow from baseline are $\Delta F_c \equiv F_c - F_c^0$ and $\Delta F_{ec} \equiv F_{ec} - F_{ec}^0$, and $d_c(\tau,\rho) \equiv -\partial \log(g_2^0(\tau,\rho)-1)/\partial F_c$ and $d_{ec}(\tau,\rho) \equiv -\partial \log(g_2^0(\tau,\rho)-1)/\partial F_{ec}$ are weighting factors that indicate the contributions of cerebral and extra-cerebral flow changes to the DCS signal change.

As described above, cerebral flow monitoring (i.e., $\Delta F_c$) can be achieved with two source-detector separations: a long separation ($\rho_l$) that samples both cerebral and extra-cerebral tissues, and a short separation ($\rho_s$) that predominantly samples extra-cerebral tissue (i.e., $d_c(\tau,\rho_s) = 0$). The two-layer DCS Modified Beer-Lambert laws for the long and short separations are:

$$\Delta OD_{DCS}^{long} \equiv -\log\left[\frac{g_2(\tau,\rho_l)-1}{g_2^0(\tau,\rho_l)-1}\right] = d_c(\tau,\rho_l)\Delta F_c + d_{ec}(\tau,\rho_l)\Delta F_{ec},$$

$$\Delta OD_{DCS}^{short} \equiv -\log\left[\frac{g_2(\tau,\rho_s)-1}{g_2^0(\tau,\rho_s)-1}\right] = d_c(\tau,\rho_s)\Delta F_c + d_{ec}(\tau,\rho_s)\Delta F_{ec}.$$

Solving this system of equations for $\Delta F_c$, we obtain $$\Delta F_c = \frac{1}{d_c(\tau,\rho_l)}\left[\Delta OD_{DCS}^{long} - \frac{d_{ec}(\tau,\rho_l)}{d_{ec}(\tau,\rho_s)}\Delta OD_{DCS}^{short}\right].$$

Evaluating the above equation for $\Delta F_c$ requires knowledge of $d_c(\tau,\rho_l)$ and the ratio $d_{ec}(\tau,\rho_l)/d_{ec}(\tau,\rho_s)$. Collecting measurements at multiple probe pressures against the head enables these two parameters to be measured.

Figure 7:
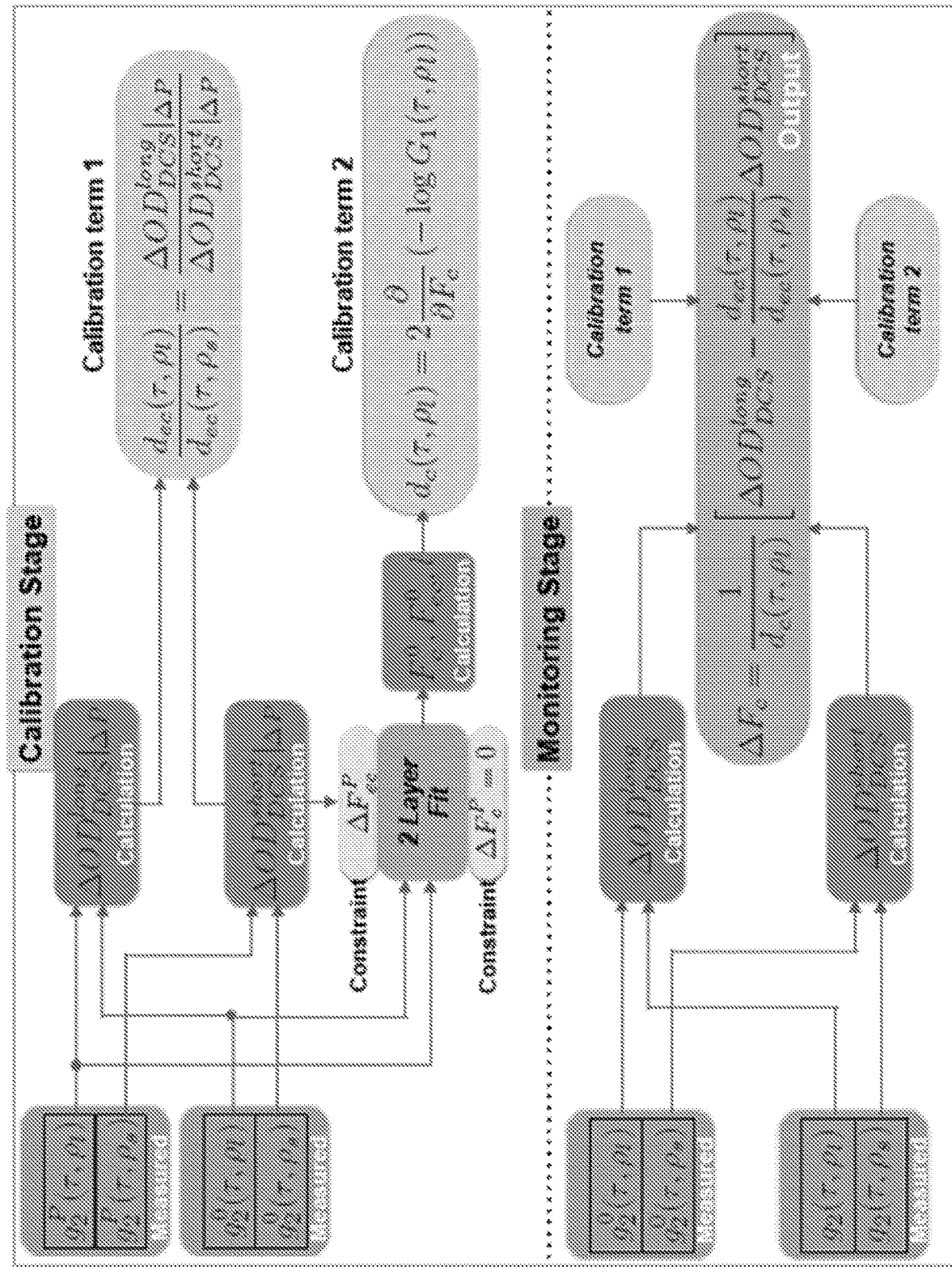
FIG. 7: A flowchart of an exemplary method—applying the DCS Modified Beer-Lambert law—for estimating a blood flow.

An exemplary schematic of the disclosed methods is provided in FIG. 7. As shown in that non-limiting figure, the probe pressure modulation algorithm for filtering superficial tissue contamination in cerebral blood flow monitoring may include a calibration stage and a monitoring stage. For the calibration stage, intensity autocorrelation function measurements at a short separation ($g_2^P(\tau,\rho_s)$) and a long separation ($g_2^P(\tau,\rho_l)$) are acquired at probe pressure P against the head. Then, the probe pressure is adjusted to a baseline value that is different than P, and baseline short-separation and long-separation intensity autocorrelation function measurements are made, i.e., $g_2^0(\tau,\rho_s)$ and $g_2^0(\tau,\rho_l)$. The measurements $g_2^P(\tau,\rho_l)$ and $g_2^0(\tau,\rho_l)$ are used to calculate the pressure-induced change in the long-separation DCS optical density, i.e., $\Delta OD_{DCS}^{long}|_{\Delta P} \equiv -\log [(g_2^P(\tau,\rho_l)-1)/(g_2^0(\tau,\rho_l)-1)]$. Similarly, the measurements $g_2^P(\tau,\rho_s)$ and $g_2^0(\tau,\rho_s)$ are used to calculate the pressure-induced change in the short-separation DCS optical density, i.e., $\Delta OD_{DCS}^{short}|_{\Delta P} \equiv -\log [(g_2^P(\tau,\rho_s)-1)/(g_2^0(\tau,\rho_s)-1)]$. Calibration term 1, which is the ratio of the long-separation extra-cerebral weighting factor to the short-separation extra-cerebral weighting factor, i.e., $d_{ec}(\tau,\rho_l)/d_{ec}(\tau,\rho_s)$, is equal to the ratio of $\Delta OD_{DDS}^{long}|_{\Delta P}$ to $\Delta OD_{DCS}^{short}|_{\Delta P}$. To see how, note that because $\Delta F_{ec} = 0$, the two-layer DCS Modified Beer-Lambert laws for a probe pressure-induced signal change are $\Delta OD_{DCS}^{long}|_{\Delta P} = d_{ec}(\tau,\rho_l)\Delta F_{ec}^P$ and $\Delta OD_{DCS}^{short}|_{\Delta P} = d_{ec}(\tau,\rho_s)\Delta F_{ec}^P$, where $\Delta F_{ec}^P$ is the pressure-induced change in extra-cerebral flow. Dividing these two equations results in $d_{ec}(\tau,\rho_l)/d_{ec} = \Delta OD_{DCS}^{short}|_{\Delta P}$.

Further, the pressure-induced change in extra-cerebral flow ($\Delta F_{ec}^P$) is determined from $\Delta OD_{DCS}^{short}|_{\Delta P}$ via the semi-infinite homogeneous DCS Modified Beer-Lambert law (see W. B. Baker, A. B. Parthasarathy, D. R. Busch, R. C. Mesquita, J. H. Greenberg, and A. Yodh, "Modified Beer-Lambert law for blood flow," Biomed. Opt. Express 5, 4053-4075 (2014)). Finally, the measurements $g_2^P(\tau,\rho_l)$ and $g_2^0(\tau,\rho_l)$ are simultaneously fit to a two-layer correlation diffusion model of light transport ($G_1(\tau,\rho_l)$) (see Baker et al.; see also D. A. Boas and A. G. Yodh, "Spatially varying dynamical properties of turbid media probed with diffusing temporal light correlation," J. Opt. Soc. Am. A 14, 192-215 (1997)) for the baseline cerebral flow, $F_c^0$, baseline extra-cerebral flow, $F_{ec}^0$, and the extra-cerebral layer thickness, l. This fit is tractable because the pressure-induced cerebral and extra-cerebral flow changes, i.e., $\Delta F_c^P$ and $\Delta F_{ec}^P$, are known. As described above, $\Delta F_{ec}^P$ is determined by the short separation measurements, and it is assumed that probe pressure variation does not affect cerebral flow, i.e., $\Delta F_c^P = 0$. This knowledge constrains the fit by reducing the number of unknown parameters to fit for in the model from five parameters ($F_c^0$, $F_{ec}^0$, $F_c^P$, $F_{ec}^P$, l) to three parameters ($F_c^0$, $F_{ec}^0$, l), which consequentially makes the fit more robust to noise. With knowledge of $F_c^0$, $F_{ec}^0$, and l, the derivative of the logarithm of the two-layer correlation diffusion solution with respect to cerebral flow is evaluated to obtain the long-separation cerebral weighting factor, $d_c(\tau,\rho_l) = -2\partial \log G_1(\tau,\rho_l)/\partial F_c$, which is calibration term 2.

In the monitoring stage, cerebral blood flow changes from baseline, i.e., $\Delta F_c \equiv F_c - F_c^0$, are determined. Here, $g_2(\tau,\rho_l)$ and $g_2(\tau,\rho_s)$ are the measured long-separation and short-separation intensity autocorrelation functions at a perturbed tissue state from baseline wherein the cerebral and extra-cerebral flows are $F_c$ and $F_{ec}$, respectively. With these measurements and the baseline measurements from the calibration stage, $\Delta OD_{DCS}^{long} \equiv -\log [(g_2(\tau,\rho_l)-1)/(g_2^0(\tau,\rho_l)-1)]$ and $\Delta OD_{DCS}^{short} \equiv -\log [(g_2(\tau,\rho_s)-1)/(g_2^0(\tau,\rho_s)-1)]$ are calculated and then combined with calibration terms 1 and 2 to compute $$\Delta F_c = \frac{1}{d_c(\tau,\rho_l)}\left[\Delta OD_{DCS}^{long} - \frac{d_{ec}(\tau,\rho_l)}{d_{ec}(\tau,\rho_s)}\Delta OD_{DCS}^{short}\right].$$

A directly analogous method can be applied for cerebral optical absorption monitoring (i.e., $\Delta\mu_{a,c}$) with light intensity measurements ($I(\rho)$). For cerebral absorption monitoring, $\Delta OD_{DCS}^{long}$ and $\Delta OD_{DCS}^{short}$ above are replaced with $\Delta OD^{long} \equiv -\log [I(\rho_l)/I^0(\rho_l)]$ and $\Delta OD^{short} \equiv -\log [I(\rho_s)/I^0(\rho_s)]$, respectively. The weighting factor parameters $d_c(\tau,\rho_l)$ and $d_{ec}(\tau,\rho_l)/d_{ec}(\tau,\rho_s)$ are replaced with the partial pathlengths $L_c(\rho_l)$ and $L_{ec}(\rho_l)/L_{ec}(\rho_s)$ (see F. Fabbri, A. Sassaroli, M. E. Henry, and S. Fantini, "Optical measurements of absorption changes in two-layered diffusive media," Phys. Med. Biol. 49, 1183-1201 (2004)). The ratio $L_{ec}(\rho_l)/L_{ec}(\rho_s) = \Delta OD^{long}|_{\Delta P}/\Delta OD^{short}|_{\Delta P}$, and the partial pathlength $L_c(\rho_l)$, is determined from evaluating the derivative of the analytical two-layer photon diffusion Green's function $G(\rho_l)$ (using knowledge of the extra-cerebral layer thickness, l, and baseline tissue properties), i.e., $L_c(\rho_l) = +\partial \log(G(\rho_l))/\partial\mu_{a,c}$. Cerebral absorption monitoring at multiple light wavelengths in turn enables the computation of cerebral oxy-hemoglobin, deoxy-hemoglobin, and blood oxygen saturation (see T. Durduran, R. Choe, W. B. Baker, and A. G. Yodh, "Diffuse optics for tissue monitoring and tomography," Reports on Progress in Physics 73, 076701 (2010)). This has implications for the growing field of functional near-infrared spectroscopy (fNIRS).

Results—Methods

Figure 2:
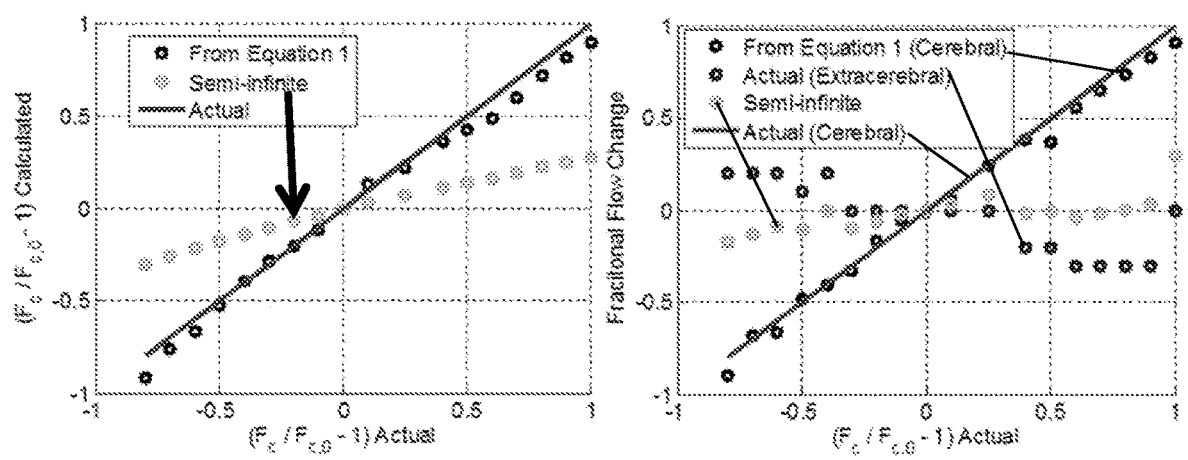
FIG. 2: Fractional cerebral blood flow changes calculated from the "probe pressure modulation algorithm" (i.e., Equation 1) and from the semi-infinite model versus the actual cerebral blood flow changes in simulated DCS data of the head under conditions of constant extracerebral blood flow (left) and varying extracerebral blood flow (right). The baseline simulated DCS data ($F_{c,0}$, $F_{ec,0}$) is depicted in the right panel of FIG. 1, and the simulated DCS data at different cerebral and extracerebral flow levels was generated the same way as described in connection with FIG. 1.

The provided "probe pressure modulation" scheme was tested on simulated DCS data of the head (FIGS. 1, 2).

Baseline simulated DCS data of the head was generated from adding simulated field autocorrelation function noise to two-layer solutions of the correlation diffusion equation at extracerebral and cerebral optical properties and flow levels representative of the scalp and brain. The cerebral blood flow was then varied from baseline while the extracerebral blood flow remained constant, which mimics localized cerebral blood flow responses to functional tasks such as finger tapping (FIG. 2, left panel).

In a second simulation data set, the cerebral blood flow was varied from the same baseline level while extracerebral blood flow also changed (FIG. 2, right panel), which is the case for more global flow perturbations such as hypercapnia that effect both the scalp and the brain.

The probe pressure modulation scheme (Equation 1) and the semi-infinite model were both applied to these simulated data sets to calculate the cerebral blood flow changes, and the results are in FIG. 2. The agreement between the calculated and actual cerebral blood flow changes is better when using the probe pressure modulation scheme than when using the semi-infinite model. The semi-infinite model is highly sensitive to the extracerebral layer. Thus, if the extracerebral flow is constant, then the semi-infinite model underestimates the true cerebral blood flow changes. Similarly, changes in extracerebral blood flow affect the calculated flow changes with the semi-infinite model.

Summary—Methods

The probe pressure modulation scheme described above on simulated DCS data of the head has been successfully employed to calculate cerebral blood flow changes with substantially less extracerebral contamination than the semi-infinite model (FIG. 2). As with the semi-infinite model, this probe pressure modulation scheme can recover cerebral blood flow changes in real time, and a priori anatomical information is not required. Of course, these techniques may be applied to other parts of a patient's anatomy.

In one aspect, the present disclosure provides methods. These methods include measuring a motion of moving scattering particles (e.g., blood components) in a subject's cerebral region, the measuring comprising illuminating the cerebral region and collecting illumination with a first source-detector pair and with a second source-detector pair, the source and detector of the first pair being separated by (a) a first distance and the source and detector of the second pair being separated by (b) a second distance, the pressures applied to the subject's cerebral region at or proximate to the locations of the first source and the second source being different from one another, one or both of the pressures being applied to as to induce variations in extracerebral hemodynamics, and isolating a cerebral hemodynamic signal from the collected illumination. Such a signal may relate to, e.g., blood flow, volume, oxygenation, and the like.

The pressures applied to the subject at the locations of the first source-detector pair and the second source-detector pair are typically selected to be clinically acceptable. A pressure applied to a subject's cerebral region at the locations of the first and second source-detector pairs is suitably in the range of from between about 0 and about 360 torr. Separation (a) may suitably be in the range of from about 0.1 to about 5 cm; separation (b) may also be in the range of from about 0.1 to about 5 cm. Illumination may be light between 300 nm and 1500 nm in wavelength; one suitable typical wavelength range is between about 660 and about 930 nm.

As described elsewhere herein, separations (a) and (b) may differ from one another. (a) and (b) may be chosen such that detected illumination from the longer of the two distances interrogates both layers when the head of the subject is modeled as a two-layer medium comprising cerebral and extracerebral layers and detected illumination from one of the two separations interrogates the extracerebral layer.

Temporal changes in extracerebral flow and cerebral flow may be related to temporal changes in measured signal at the longer of (a) and (b) and may be modeled via the Modified Beer Lambert Law applied to a two layer medium. The methods may be characterized as including diffuse correlation spectroscopy, diffuse optical spectroscopy, diffuse reflectance spectroscopy, or other techniques utilizing approximations to the radiative transport equation. This method may be extended to additional source-detector separations and layers (e.g., 5 source-detector separations and 3 layers).

Also provided are methods, comprising: measuring a motion of moving scattering particles in a subject's tissue, the measuring comprising illuminating the cerebral region and collecting illumination from a first source-detector pair and with a second source-detector pair, the source and detector of the first pair being separated by (a) a first distance and the source and detector of the second pair being separated by (b) a second distance, the pressures applied to the subject's tissue at or proximate to the locations of the first source and the second source being different from one another, one or both of the pressures being applied to as to induce variations in tissue hemodynamics, and isolating a tissue hemodynamic signal from the collected illumination.

A non-limiting listing of suitable tissues includes brain, muscle, and/or breast; brain is considered especially suitable as is pliable healthy tissue overlying a mechanically stiff tumor. One of the pressures applied to the subject's tissue at the locations of the first and second source-detector pairs is in the range of from about 0 to about 360 torr. As described elsewhere herein, (a) may be in the range of from about 0.1 to about 5 cm, and (b) may be in the range of from about 0.1 to about 5 cm. Illumination may be illumination having a wavelength of between about 300 nm and about 1500 nm. It should be understood that a user may use two, three, or even more source-detector pairs to perform the disclosed methods and that—likewise—the disclosed devices may include two, three, four, or even more source-detector pairs.

Separations (a) and (b) may differ from one another, and (a) and (b) may be chosen such that detected illumination from the longer of the two distances interrogates both layers when the tissue is modeled as a two-layer medium that comprises tissue and extra-tissue layers and detected illumination from one of the two separations interrogates the extra-tissue layer. Temporal changes in extra-tissue blood flow and tissue blood may be related to temporal changes in measured signal at the longer of (a) and (b) modeled with the Modified Beer Lambert Law. The methods may be characterized as including diffuse correlation spectroscopy, diffuse optical spectroscopy, diffuse reflectance spectroscopy, or other techniques utilizing approximations to the radiative transport equation. Again, it should be understood that although the foregoing discussion is focused on cerebral applications, the disclosed techniques may be generalized and applied to essentially any patient tissue.

Devices

As described elsewhere herein, Diffuse Correlation Spectroscopy (DCS) is a light scattering technique that measures CBF through the interaction of coherent light with moving particles. In practice, tissue (e.g., the head) is illuminated with coherent laser light using fiber optics, and the light scattered through the tissue (e.g., brain) is detected ~2.5 cm away on the surface of the head. Interaction of the scattered light with moving particles in the blood (RBCs) causes the detected intensity to fluctuate in time. The characteristic time scale of these fluctuations is a measure of CBF or other anatomical blood flow. More quantitatively, the temporal autocorrelation function of the detected intensity is computed and fit to a correlation diffusion equation to extract a quantitative and validated measure of CBF or other anatomical blood flow. Because DCS is sensitive to all moving particles in the sampling area, it is well-correlated with micro-vascular and parenchymal flow, as opposed to transcranial Doppler (TCD) measurements, which are sensitive to large vessels.

Figure 3:
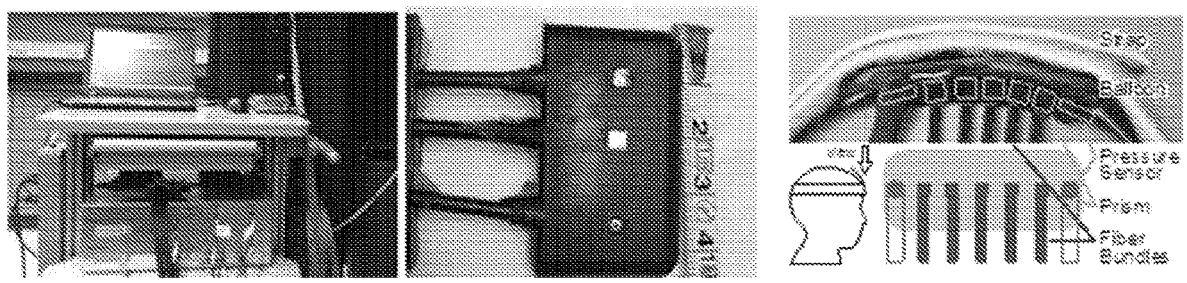
FIG. 3: (left) A portable DCS/DOS instrument with attached fiber optics, (middle) prism coupled exemplary DCS/DOS fiber optic probe with two source-detector separations, and (right) schematic and photo of exemplary fiber optic probe with κ prisms and 2 pressure sensors, balloon for pressure modulation and elastic band. An embedded accelerometer is not shown.
Figure 4:
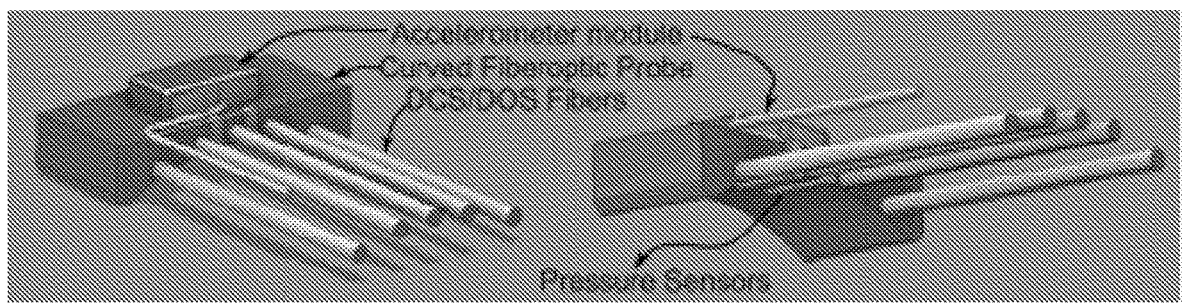
FIG. 4: a 3-D rendering of an exemplary, non-limiting curved probe with accelerometer.
Figure 5:
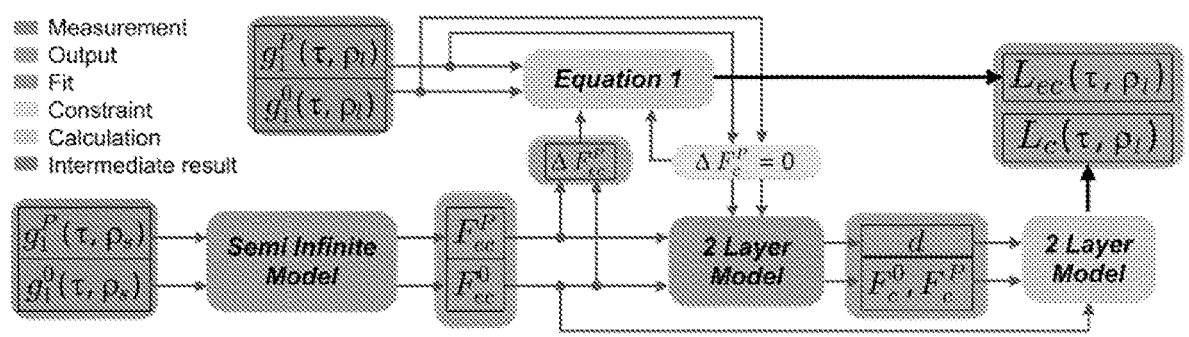
FIG. 5: A flowchart of an exemplary algorithm to derive patient-specific layer properties to be used to isolate CBF via Eq. 1 during clinical manipulation

An exemplary DCS instrument used in this study is shown in FIG. 3—left. The portable device consists of 2 long coherence length near infrared lasers (785 nm, Crystalaser) and 8 photon counting avalanche photodiodes (APD, Perkin Elmer), connected to flexible single mode fiber optics (Fiberoptic Systems Inc.). A built-in correlator (Correlator.com) reads the photon counts from the APDs and computes the intensity correlation functions. Exemplary data acquisition and estimation of CBF was done using custom written software. In one study, flexible fiber optic probes were attached to a patient's forehead with medical-grade adhesive and were secured using soft elastic wraps around the head (FIG. 3—right).

Several approaches to a fiber probe—skin interface are presented in one DCS instrument. First, the illumination and detector fibers were terminated with a 3 mm prism (Thorlabs, PS905), which improved signal-to-noise (SNR) by ~3×. Additionally, multiple detector fibers were terminated to a signal prism (and hence a single detector position), allowing for averaging of computed correlation curves to further improve signal-to-noise ratio. This design ensured that the probe (FIG. 3—middle) was small, flexible and patient friendly.

Probes were manufactured using molds produced by 3D printing technology (Next Fab inc.), which enabled precise positioning of the prisms, and contouring of the probes to fit the head curvature. FIG. 3's, middle and right figures show different exemplary probes; the probe in the middle panel is a DCS probe that features two probe-detector separations. The probe in the right panel is a DCS/DOS probe that features four different separations. Finally, pressure sensors and accelerometers were incorporated into the probe to enable robust measurement. Pressure measurements ensure proper and uniform probe-skin contact, while accelerometers help detect periods with motion artifacts.

In one non-limiting application of the disclosed technology, one may apply the technology to analysis of stroke patients. The following discussion is one non-limiting, exemplary use of the disclosed technology in a cerebral application.

Acute strokes are characterized by permanent damage to some portion of the brain—the ischemic core, and a surrounding region—the penumbra—where damage is reversible. The primary goal of stroke intervention techniques is to increase cerebral blood flow in the brain, specifically in the penumbra, to minimize damage.

Simple methods to increase CBF like lowering of the head of the patient have shown measurable effects and clinical potential. Techniques like administration of hypertensive agents are not widely applicable and have shown inconclusive results. An intravenous administration of saline increases the fluid volume and hence CBF. The utility of this stroke intervention for patients with AIS is shown here using an improved DCS/DOS device.

An illustrative study was approved by an Institutional Review Board of the Hospital of the University of Pennsylvania, and patients with AIS (acute ischemic stroke) (n=5) were recruited from the stroke unit at the Hospital of the University of Pennsylvania. After obtaining informed consent from patients, fiber optic probes were placed bilaterally at the temporal margin of the forehead, superior to the frontal sinuses and secured using medical grade adhesive tape (3M) and flexible cloth wrap. CBF was acquired continuously throughout the experiment using the DCS/DOS device. After a brief neurological exam, ~15 minutes of baseline CBF measurements were collected, following which 500 cc of 0.9% NaCl was intravenously administered for 30 mins. The experiment concluded with 15 minutes of post-intervention measurements.

Figure 6:
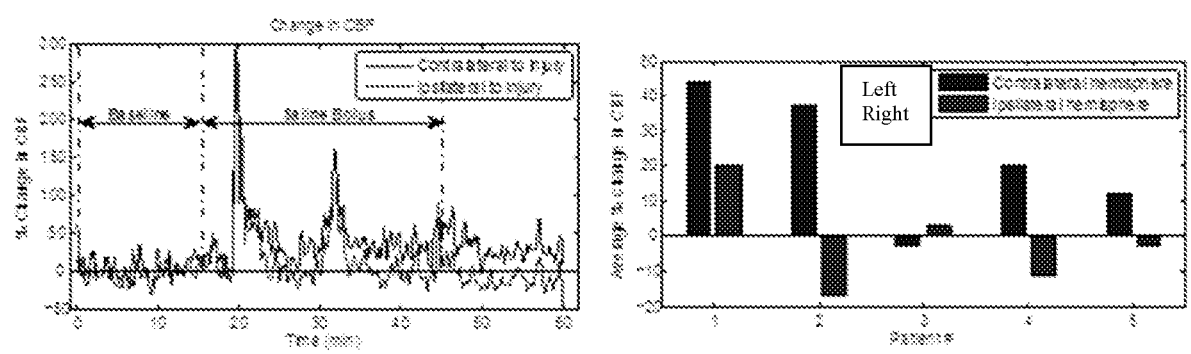
FIG. 6: (left) Relative change in CBF during intravenous administration of normal saline to a patient with a large left sided stroke. The time courses have been averaged with a N=5 moving average window (right) Summary of average change in CBF in all patients due to intravenous administration of normal saline. Contralateral hemisphere data are the left bar at each patent #, and ipsilateral hemispherical data are the right bar at each patient #.

Preliminary results from this study were as follows. FIG. 6—left shows the time course of % change in CBF during the course of an intravenous injection of saline to a patient with a large left sided stroke. The hemisphere contra-lateral to the injury shows an ~40% increase in CBF, while the ipsi-lateral hemisphere shows a fairly small change in CBF. FIG. 6—right shows a summary of the average change in CBF in the contra- and ipsi-lateral hemispheres due to the saline bolus intervention in all patients. The hemispherical asymmetries are apparent from this summary, with some patients even showing a decrease in CBF in the ipsi-lateral hemisphere. On average the change in CBF in the contralateral hemisphere was found to be 22%, while the change in CBF in the ipsilateral side is −1.5%.

Without being bound to any particular theory, one explanation for the heterogeneous results in FIG. 6—right is the vast differences in the extent of injury. For example, patient 1 had a severe stroke, while patients 3,4,5 had very mild symptoms. Again without being bound to any particular theory, it is possible that injury severity and stroke type have a significant effect on the CBF response to the saline bolus intervention. Thus, it was demonstrated that DCS can be used to monitor CBF changes during stroke intervention in patients with acute injury. Preliminary results show that an intravenous administration of normal saline causes an increase in CBF in the hemisphere contralateral to the injury.

As will be known to those of ordinary skill in the art, non-invasive diffuse optical measurements of tissue (e.g., cerebral) hemodynamics depend on stable positioning of light sources/detectors. However, it is challenging for subjects to remain perfectly still (e.g., infants and children), and some paradigms such as HOB positioning involve deliberate motion. Motional artifacts are important for photon correlation (DCS) measurements, because the resultant apparent movement of static scatterers in tissue can cause additional signal decorrelation. Additionally, motional artifacts may lead to positional uncertainties, light leakage, and signal corruption that affect both DCS & DOS/NIRS. Experiments suggest that motion artifacts may also be considered in cerebral measurements as well as in measurements of other parts of a patient's anatomy.

Accelerometers (e.g., motion sensors) may be integrated into the probes to continuously track the change in position of the patient's anatomy under study (e.g., head). These devices measure acceleration along three orthogonal axes. Optical measurements made in a clinical setting are susceptible to artifacts arising from sudden motion by the subject.

Additionally, restless subjects may touch or adjust the probes, affecting both DOS and DCS measurements. Such motion artifacts are a significant source of experimental noise in clinical measurements. For blood flow measurements using DCS, this is especially significant, as the technique is sensitive to all motion, not just that of blood. Although correlation decays can be separated out to some extent based on the time scale of these artifacts, motion artifacts remain a significant challenge during episodic occurrences like seizures or stammers, and in pediatric subjects. There is thus a necessity to develop techniques and methods to remove the effect of motion artifacts. Thus, described herein are devices that integrate an accelerometer into a probe that permits continuous recording of probe motion and thence automated detection of motion artifacts.

To understand patient motion, and its relation to measurements, one may will track correlations between the time courses of CBF and net acceleration in a subject population. Time intervals wherein flow and motion are highly correlated may be identified as periods of "significant motion" using a threshold identified from calibration test studies. This filter may identify time-windows with potentially large 'artificial' motion, may provide real-time feedback to the clinician if significant movement is occurring, and may help select data with artifacts (in real-time and retrospectively).

Traditionally, DCS and DOS fibers have been physically separated into separate fiber optic bundles. The disclosed technology may, in some embodiments, co-locate single mode DCS detector fibers with multimode DOS detector fibers into a single bundle with a single distal (skin) end and two proximal (detector) sub-bundles. Furthermore, one may also secure source fibers for DOS and DCS onto a single prism to couple light into the skin. Together, these improvements increase the overlap in the tissue volume probed by the two techniques.

Probes may also be built to: (1) improve physical and optical coupling through a range of head curvatures, (2) monitor pressure and motion, and (3) permit uniform pressure adjustment. One design terminates fibers with a prism (e.g., Thorlabs, PS905). A detection fiber optic bundle may include multi-mode fibers (44.6 µm-core/0.55NA) for DOS/NIRS and single mode fibers (5 µm-MFD/0.13NA) for DCS, thereby facilitating co-localized blood flow and oxygenation measurements. Coupling of light through prisms reduces mechanical stress and increases light throughput at the skin-probe interface. With prism-coupled single-mode detection fibers, one may observe ~3× increases in SNR, which in turn enables increased source-detector separation distances that probe deeper into cortical tissues and improved temporal resolution.

Probes may conform to the anatomy of the patient, e.g., the varied head or chest curvatures of neonates to adults in the patient populations. One may manufacture a library of customized fiber optic probes with curvatures corresponding to head circumferences ranging from 25 cm (premature babies) to 60 cm (adult) circumference, and one may use 3D printing (e.g., NextFab Studios, LLC) to produce the molds that shape the probes. The process may include precision insets for the prism-couplers. A probe library may also be constructed for other parts of a patient's anatomy, e.g., to conform to a patient's chest or other muscles.

To acquire data at different probe pressures, one may introduce flexible pressure sensors (e.g., Tactilus Free Form, Sensor Products Inc.) into the fiber optic probe (FIG. 3). Medical-grade double-sided tape ensures proper probe contact and reduces skin-probe movement. To facilitate real-time motion sensing, small, low power accelerometers (e.g., Analog Devices ADXL335) may be embedded into the fiber optic probe during manufacture; the sensor and associated electrical connections will be held in place above the prism-coupled fibers and elastomer will be poured around it. Signals from the pressure and motion sensors are logged onto a computer, and integrated into existing custom clinical instrument control software.

A schematic and photograph of an exemplary probe support and pressure adjustment system adapted for cerebral applications is shown in FIG. 3. The probe on each hemisphere may be held onto the head by several techniques, e.g., (1) a soft elastic strap wrapped around the head and over the probe; (2) or a pliable neoprene sheet, with an adjustable strap. The elastic/adjustable straps wrap around the probe and head to set up a secure configuration. A hand inflatable air balloon (e.g., American Diag. Corp, 875N) may be inserted between the probe and elastic strap to permit systematic increase/decrease of probe pressure, while monitoring pressure via the embedded sensors. Pressure adjustments may also be mechanized under computer control.

Thus, the present disclosure provides devices, comprising: a first illumination source-detector pair, the source and detector being separated by a first distance (a); a second illumination source-detector pair, the source and detector being separated by a second distance (b); and an element configured to apply (or measure, or both) a pressure between the device and the subject's body. The devices may include additional source-detector pairs at the same or at additional distances. A device may also include an element (e.g., an accelerometer) configured to measure acceleration or motion of the tissue being studied, the device being used, or both.

In some embodiments, at least one of the first and second source-detector pairs comprises optical fiber. An illumination source, an illumination detector, or both may be disposed within a bundle of optical fibers.

A device may further include an illumination element in electrical or optical communication with the first, second, or both illumination source-detector probes. Such elements include a LASER (Light Amplification through Stimulated Emission of Radiation), a lamp, a light emitting diode (LED), or any combination thereof.

The first illumination source, the first illumination detector, the second illumination source, the second illumination detector, or any combination thereof may be in optical communication with a prism. An illumination detector may be in optical communication with a prism.

As described elsewhere herein, separations (a) and (b) may differ from one another. The first illumination source, the first illumination detector, the second illumination source, the second illumination detector, or any combination thereof, may be characterized as being conformable to a patient's anatomy, e.g., by use of a flexible material such as a plastic or mesh.

A device may also include an accelerometer. A user may use the accelerometer to identify periods when the patient may have been moving, which in turn may be used to discard or discount data gathered during periods of motion.

A device may include a sensing element configured to measure pressure between a portion of the device and the patient's body (e.g., head). The element may be a balloon, a hydraulic element, a servo, a motor, or any combination thereof. A device may also include, e.g., a photon counting avalanche diode, a photomultiplier tube (PMT), a photo diodes (PD), an avalanche photodiode (APD), a charge coupled device (CCD), a complementary metal oxide semiconductor (CMOS), or any combination thereof in electronic communication, optical communication, or both, with at least one of the first or second illumination detectors. A device may also include an element configured to compute intensity correlation functions from photon counts, the device being in electronic communication, optical communication, or both with a illumination detector probe.

A user may use the disclosed devices to measure a motion of moving scattering particles in a subject's tissue (e.g., blood components). A user may further isolate tissue blood flow signals from collected illumination. A user may also use the disclosed devices to apply a pressure to a subject's body. A user may utilize the disclosed devices to separate superficial (scalp) and underlying (cerebral) blood flow. A user may utilize the disclosed devices to conduct long-term (hours-weeks) monitoring of tissue hemodynamics in a clinical or outpatient setting.

Figure 16:
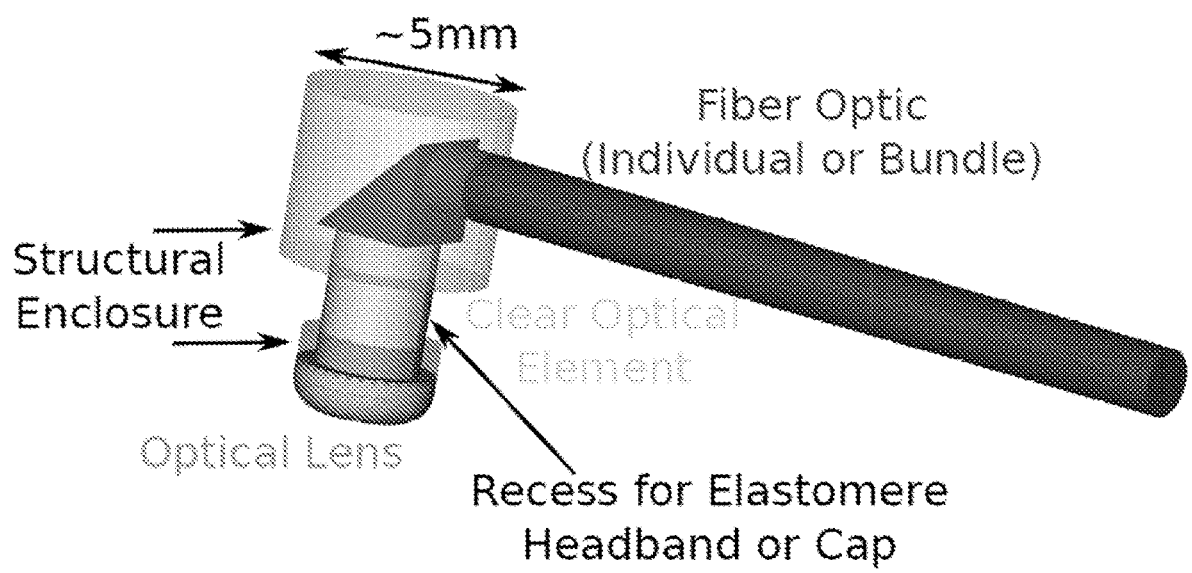
FIG. 16 provides an exemplary device according to the present disclosure. An optical fiber or fiber bundle and prism are optically coupled to an optical element (e.g., formed from additive manufacturing techniques) and an optical-skin interface. Structural elements surround the junctions.
Figure 17:
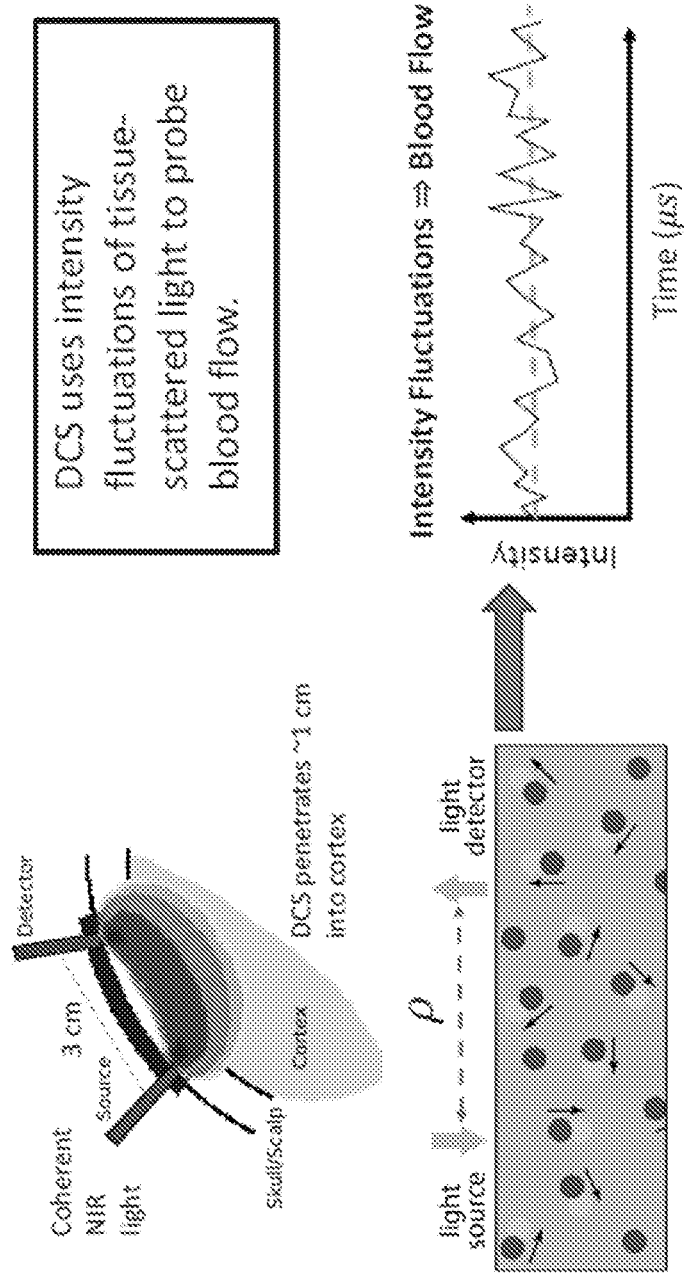
FIG. 17 provides an illustration of basic DCS measurement. Moving red blood cells (dark disks at time t, lighter disks at time t+τ) within the sampled "banana shaped" tissue volume induce intensity fluctuations. The faster the motion, the faster the fluctuations.
Figure 18:
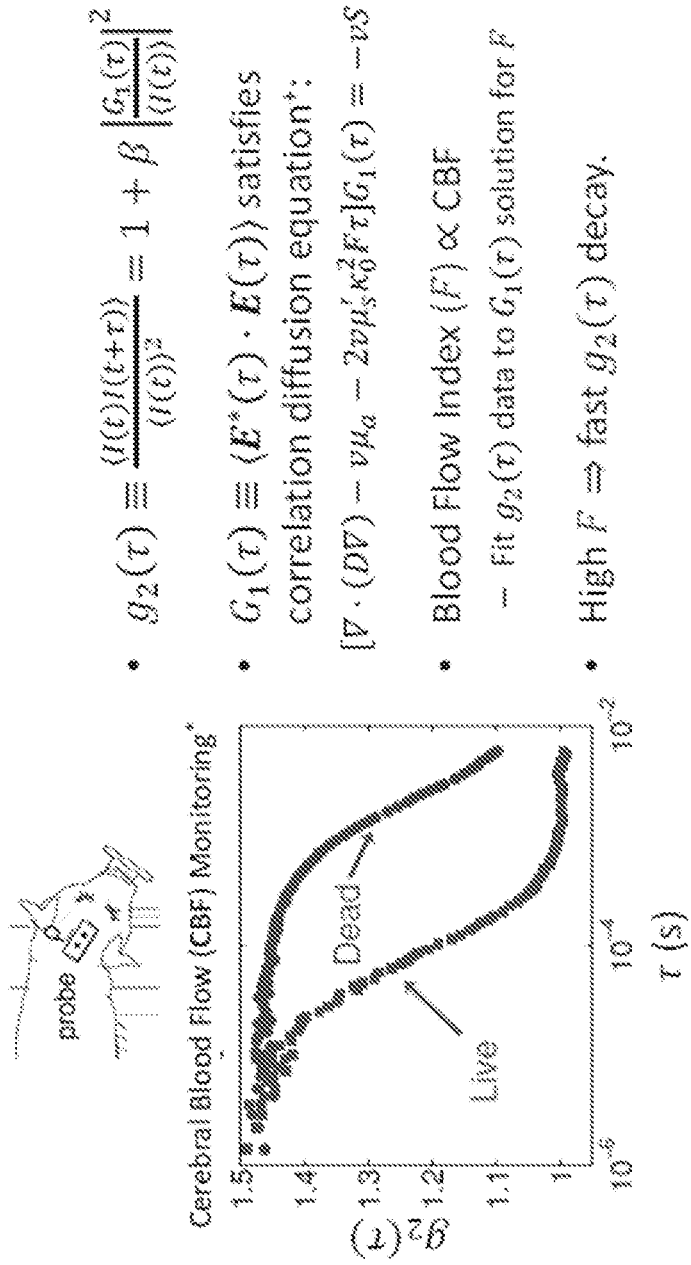
FIG. 18 provides an overview of intensity fluctuations characterized by the autocorrelation function. Intensity fluctuations are characterized by an intensity autocorrelation function, $g_2$. The decay of $g_2$ over delay-time $\tau$ is related to tissue blood flow. Quantitatively, the electric field (E) auto-correlation function, $G_1$, satisfies a correlation diffusion equation. The solution to the correlation diffusion equation depends on a blood flow index, F, that is directly proportional to tissue blood flow. The correlation diffusion approach to flow monitoring is to fit the measured intensity autocorrelation function to the electric field autocorrelation solution in order to extract the blood flow index, F.
Figure 19:
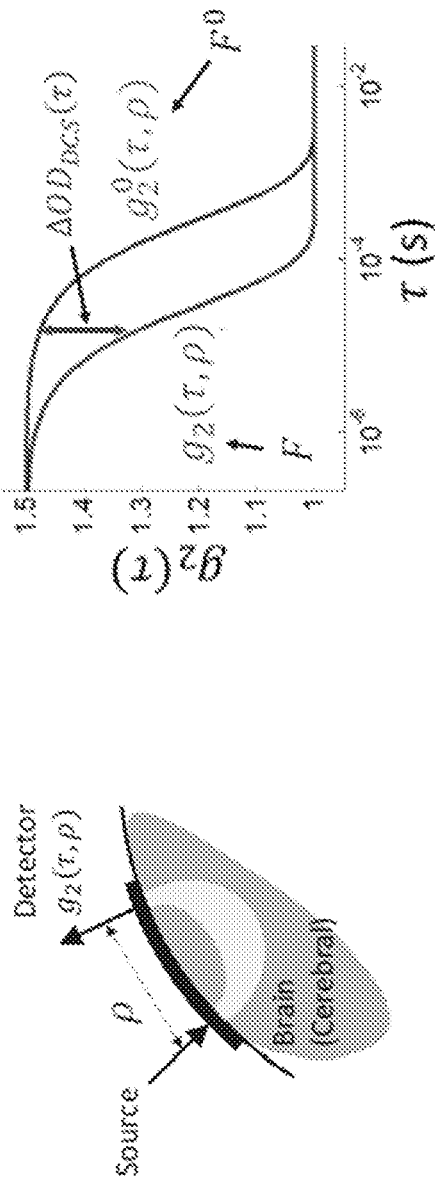
FIG. 19 illustrates the Modified Beer-Lambert Law for flow. In analogy to the NIRS Modified Beer-Lambert law, the Modified Beer-Lambert law for flow relates changes in a DCS optical density, $OD_{DCS}$, at delay time $\tau$ to the blood flow change, $\Delta F$. The multiplicative weighting factor $d_F$ is the DCS analogue of the differential pathlength, and is evaluated through numerically solving the flow derivative of the baseline DCS optical density. The Modified Beer-lambert law for flow is a system of equations, i.e., one equation for each delay-time, that can be rapidly solved for flow in a least squares sense.
Figure 20:
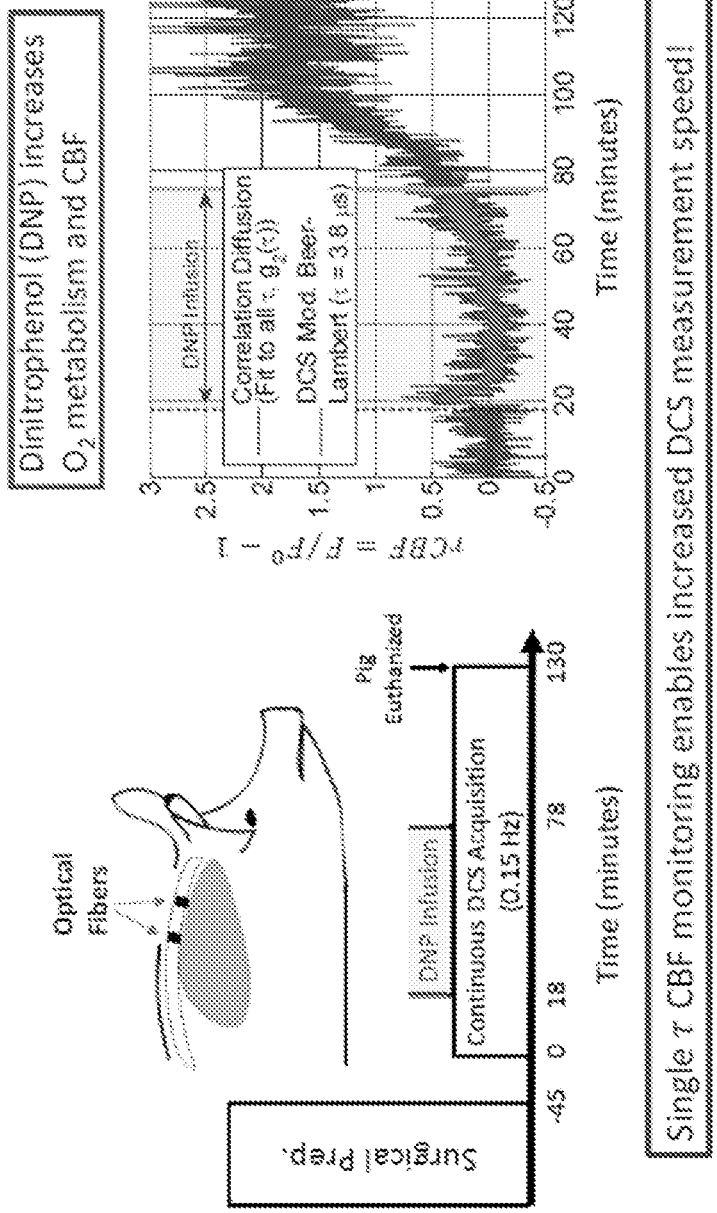
FIG. 20 illustrates a validation of the DCS Modified Beer-Lambert Law. The DCS Modified Beer-Lambert law for flow was validated on a pig. The pig was given the drug dinitrophenol (DNP), which induced a big increase in cerebral flow. This increase was then calculated with the standard correlation diffusion approach and with the DCS Modified Beer-Lambert law. There is good agreement between the two techniques. Since the Modified Beer-Lambert law only needs one delay-time instead of many delay-times, it is theoretically possible to measure blood flow with a higher measurement speed using the DCS Modified Beer-Lambert law approach.
Figure 21:
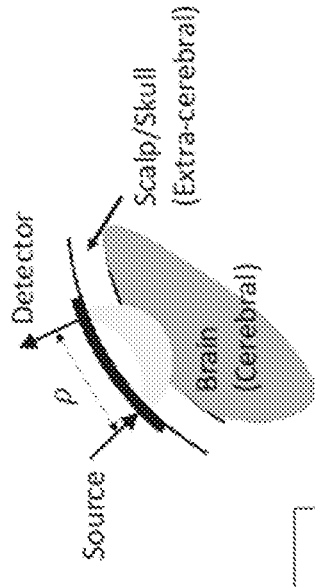
FIG. 21 illustrates a multi-layer model of the head. Cerebral tissue is commonly modelled as homogeneous, but in reality it is layered. The presence of a superficial layer strongly influences the measured signal, $g_2$. Thus, flow changes in the superficial layer will induce signal changes, which contaminate the measurement of cerebral blood flow.
Figure 21:
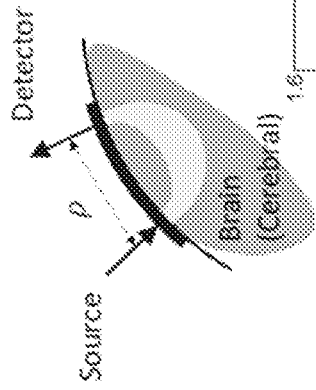
Figure 21:
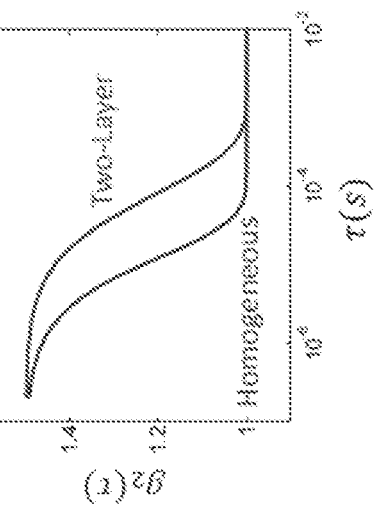
Figure 22:
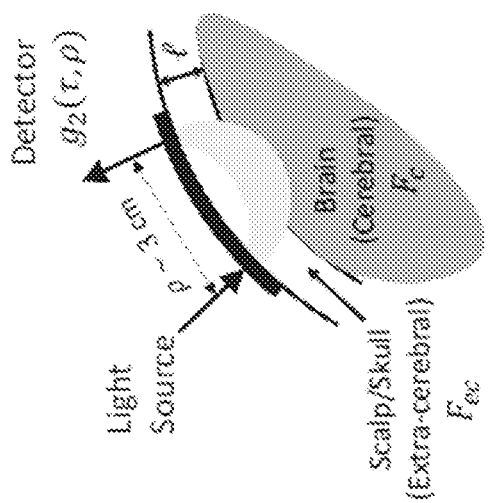
FIG. 22 presents a 2-layered Modified Beer-Lambert law for flow. A two-layer Modified Beer-Lambert law for flow can be used to reduce extra-cerebral contamination in cerebral monitoring, which relates the change in DCS signal to changes in cerebral flow ($\Delta F_c$) and changes in extra-cerebral flow ($\Delta F_{ec}$). The two-layer model consists of a homogeneous cerebral layer below a homogeneous extra-cerebral superficial tissue layer of thickness l. The weighting factors $d_c$ and $d_{ec}$ are DCS analogues of the NIRS partial pathlengths, and they are evaluated from taking the appropriate derivative of the baseline DCS optical density.
Figure 23:
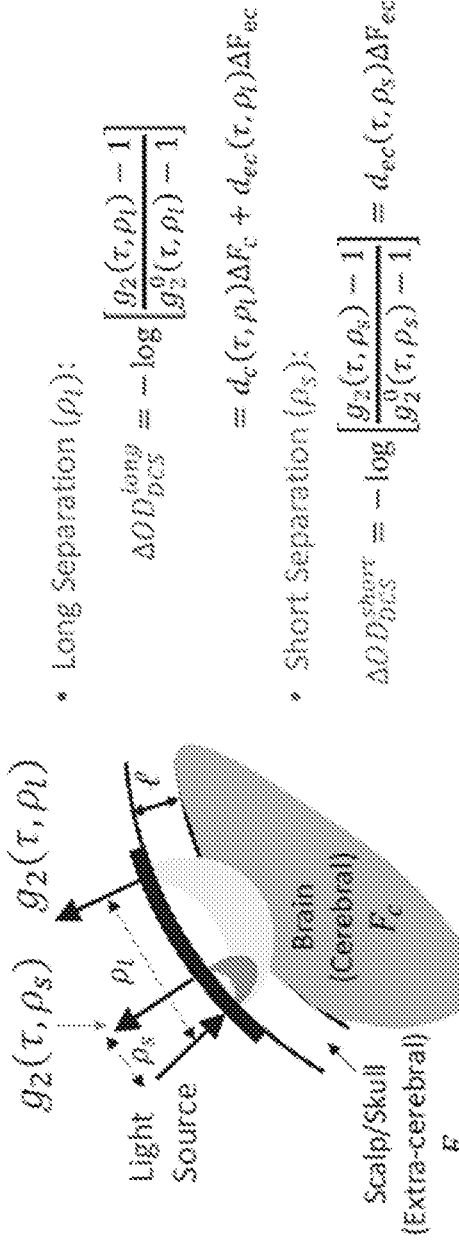
FIG. 23 presents a 2-layered, 2-separation distance Modified Beer-Lambert Law for flow. To constrain the two-layer model, two source-detector separations probe the head. One separation is short, and consequentially only samples the extra-cerebral layer. There is a two-layer DCS Modified Beer-Lambert law for each separation. This system of two equations is solved for the cerebral flow change.
Figure 24:
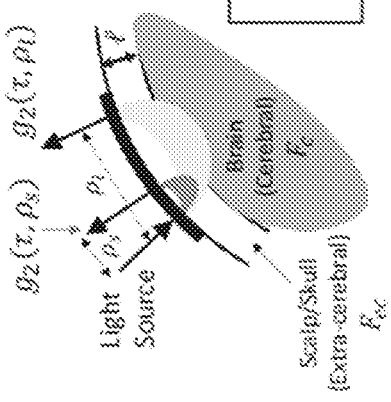
FIG. 24 presents a 2-layered, 2-separation distance Modified Beer-Lambert Law for flow. To solve for the cerebral flow change, knowledge of the ratio of extra-cerebral weighting factors and knowledge of the long-separation cerebral weighting factor are required. Probe pressure modulation permits the measurement of these parameters.
Figure 25:
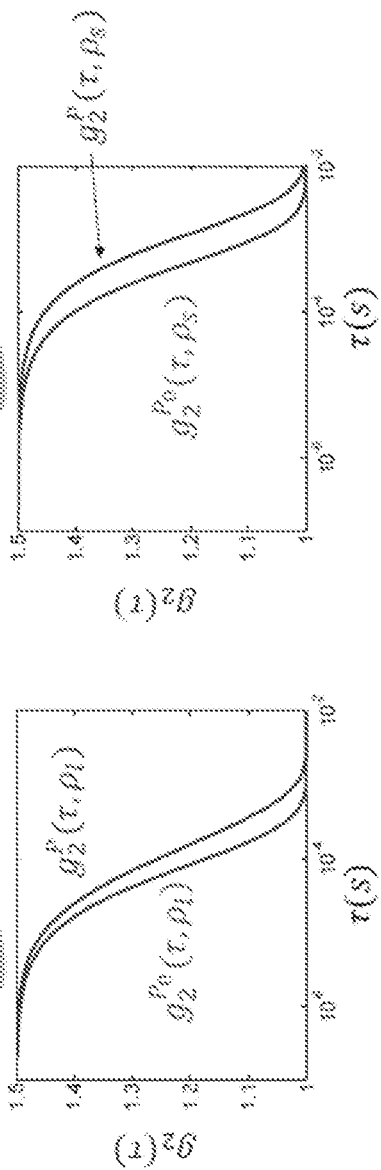
FIG. 25 presents probe pressure modulation calibration of DCS. Changing the probe pressure against the head induces changes in signal at both the long and short separations. It is assumed that these signal changes arise entirely from extra-cerebral contamination, because changing the probe pressure should not affect cerebral flow.
Figure 26:
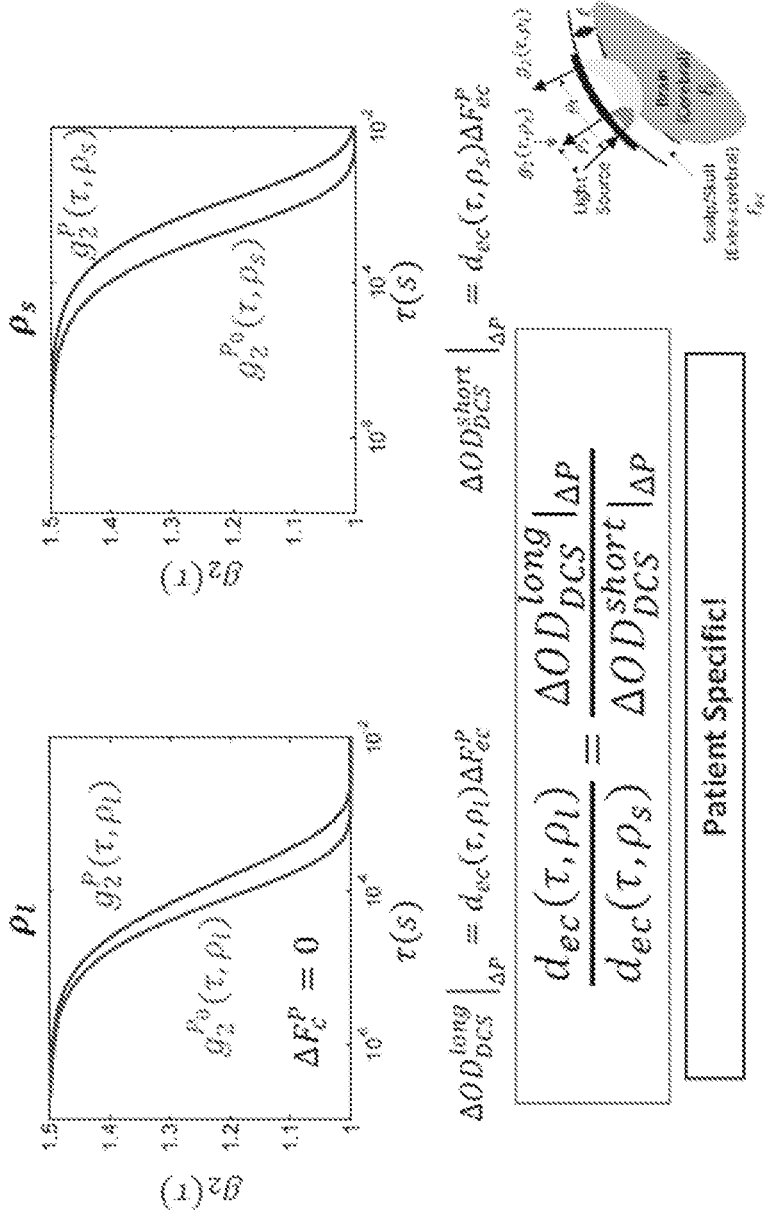
FIG. 26 illustrates correlation functions measured at 2 pressures and 2 separation distances. Dividing the long and short separation DCS Modified Beer-Lambert laws for the pressure-induced signal change enables direct measurement of the ratio $d_{ec}(\tau,\rho_l)/d_{ec}(\tau,\rho_s)$. Thus, through acquiring long and short separation measurements at two pressures, this key parameter for calculating cerebral flow can be measured in a patient-specific manner.
Figure 27:
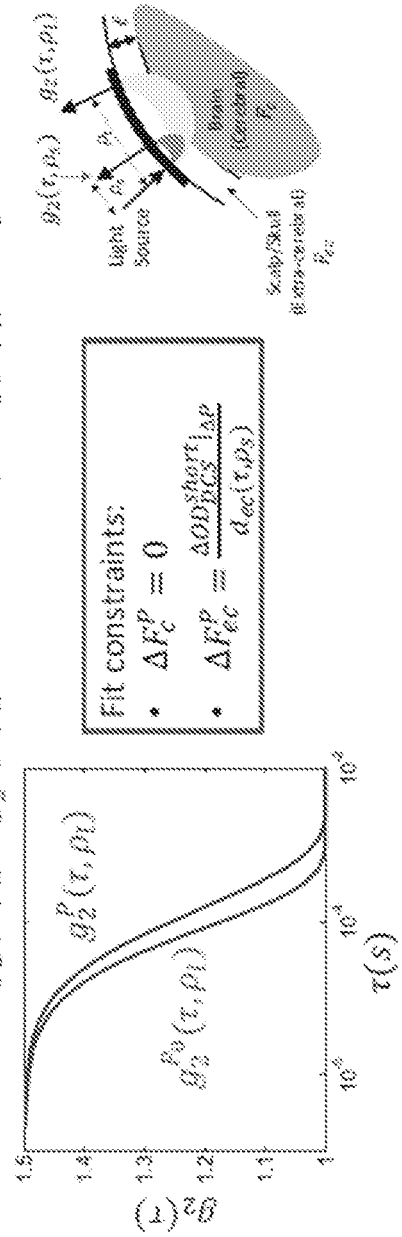
FIG. 27 cerebral blood flow with probe pressure calibration. To calculate the remaining unknown, $d_c$, the numerical derivative of the logarithm of the two-layer correlation diffusion solution ($G_1$), needs to be evaluated. Evaluation requires knowledge of the baseline cerebral flow and layer-thickness. These can be determined by fitting the two long-separation signals acquired at two probe pressures to the two-layer correlation diffusion model. Constraints in this fit are that the pressure-induced cerebral flow change is zero, and that the pressure-induced extra-cerebral flow change is determined from the short separation measurements via semi-infinite homogeneous techniques.
Figure 28:
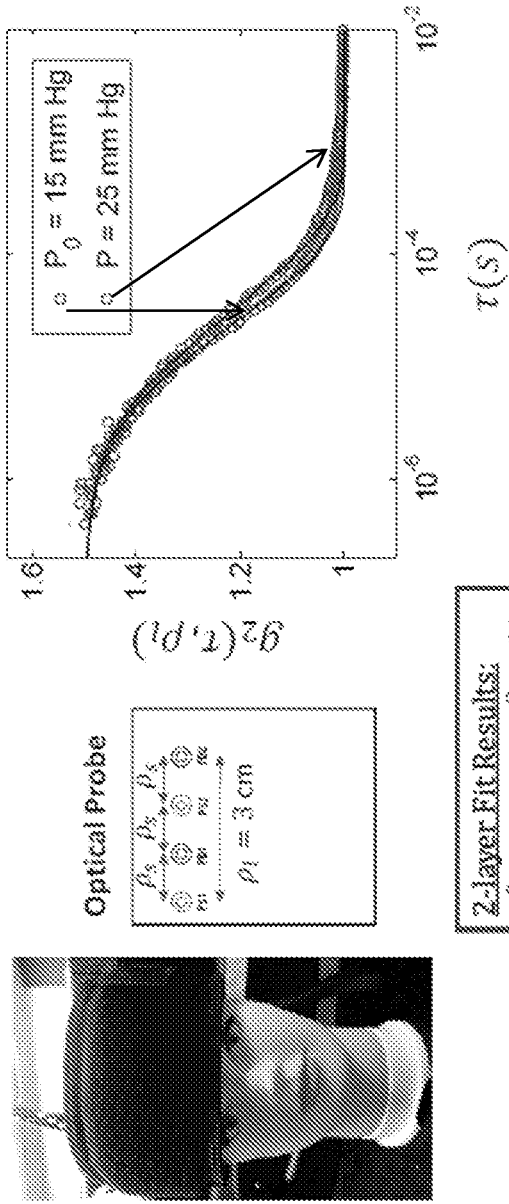
FIG. 28 illustrates DCS pressure calibration on an adult subject. Results of two-layer fit for cerebral flow and the layer thickness on an exemplar subject. A blood pressure cuff wrapped around the head was used to adjust the pressure.
Figure 29:
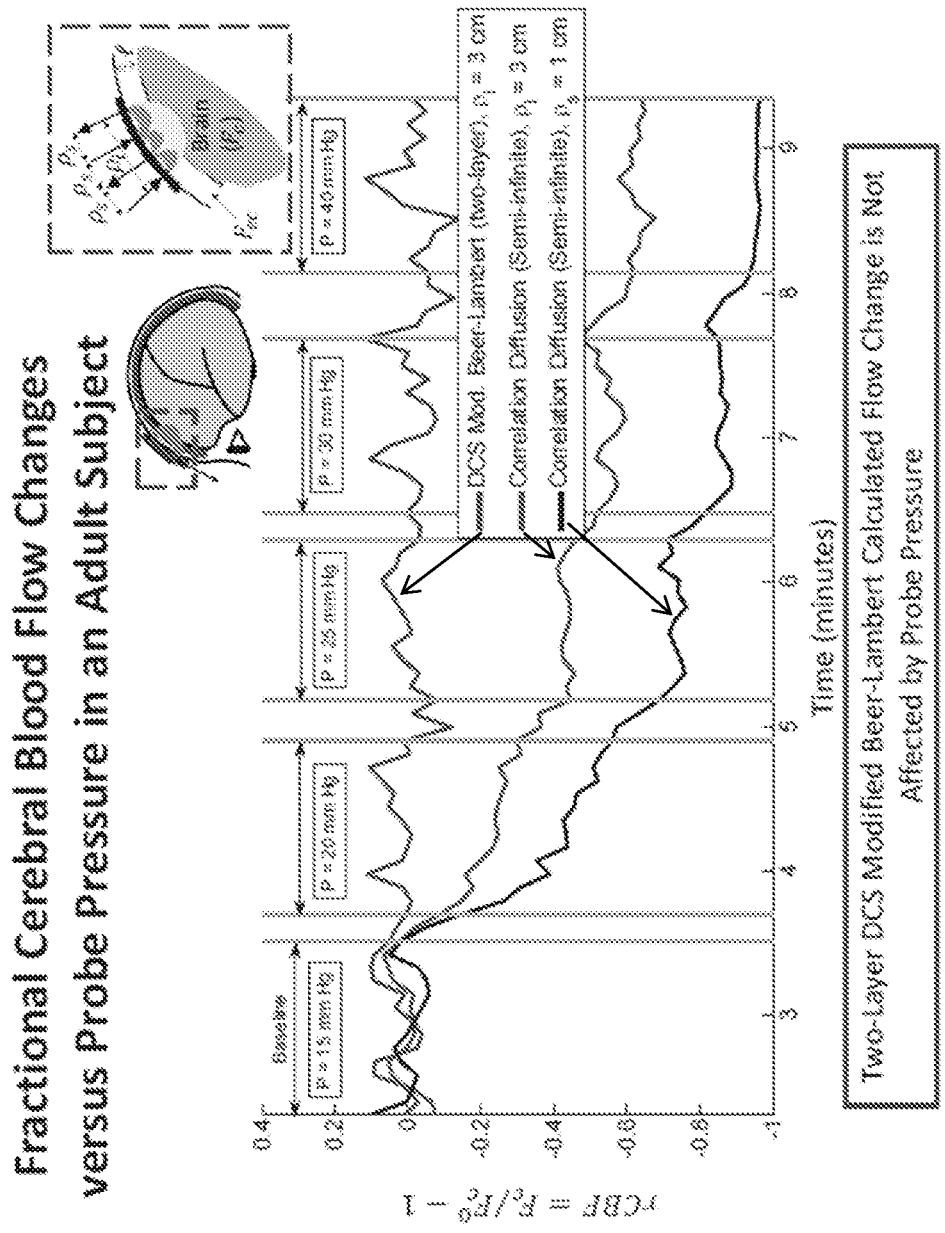
FIG. 29 illustrates cerebral blood flow changes versus pressure in an adult subject. The fractional cerebral blood flow change over multiple probe pressures against the head, as computed with the two-layer DCS Modified Beer-Lambert law and as computed with the semi-infinite homogeneous model at the long and short separations. The short separation semi-infinite calculation is the extra-cerebral fractional flow change from increasing probe pressures. As the probe pressure approaches venous pressure, the extra-cerebral flow goes to zero. The long separation homogeneous calculation of cerebral flow is substantially contaminated by this extra-cerebral change, as evident from the large computed decrease in cerebral flow. However, the two-layer DCS Modified Beer-Lambert law calculation of cerebral flow is not sensitive to probe pressure variation, as should be the case. Thus, the two-layer DCS Modified Beer-Lambert law successfully removed the extra-cerebral contamination from the long separation signal.
Figure 30:
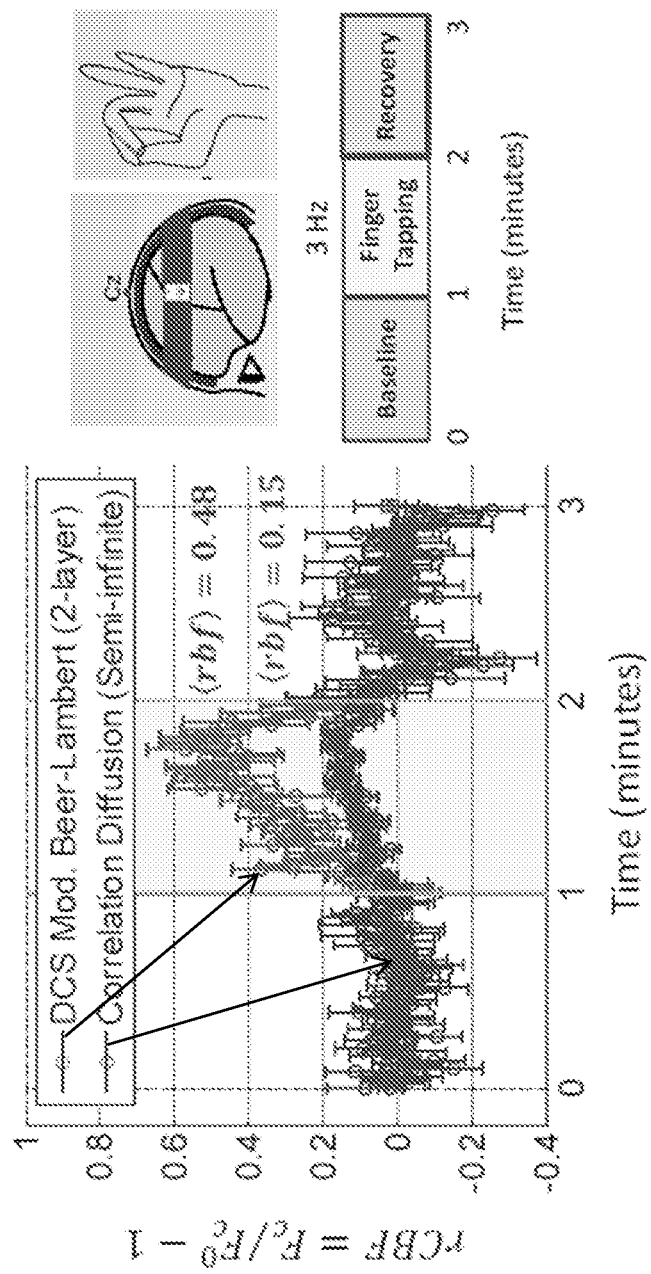
FIG. 30 presents measured CBF response to finger tapping in an adult subject.

FIG. 16 provides an exemplary device. As shown in that figure, a probe may include a housing that surrounds a set of optical components. In one embodiment, the housing may include two larger cylinders concentric with a smaller cylinder. This shape permits the device (as a rigid or semi-rigid body) to be integrated into a sheet or band (e.g., a rubber cap) to hold the probe close to the subject's head. In one exemplary embodiment, the device includes a recess (shown) or protrusion (not shown) engages with a hole or other feature of a sheet, cap, or band so as to maintain the device in place.

Several components may be within the housing. Such components may be, e.g., a fiber optic, a prism or mirror, a short optical component, and a lens or other optical component that interfaces with the skin. The interfacing component may have rounded edges so as to interface more comfortably with the skin.

Optical components may be physically fused together. Such components may also have optical coupling gel (Cargille and Thorlabs are considered suitable suppliers of such gels) between joints to provide freedom to rotate and thus reduce breakage. Optical coupling gel may also be used at the skin-device interface. In particular, this interface may utilize scattering optical coupling gel in order to minimize the number of diffuse-non-diffuse boundaries. The optical components and plastic housing may, in some embodiments, be assembled and/or created with additive manufacturing in their final position.

The fiber optic of the disclosed devices may comprise a single fiber, a bundle of similar fibers, or a bundle of dissimilar fibers. As described elsewhere herein, one may include single mode fibers for diffuse correlation spectroscopy measurements along with multimode fibers for diffuse optical spectroscopy measurements.

FIG. 16 is one exemplary embodiment of such a device. As shown in that figure, a device may include an optical lens that is in optical communication with a fiber optic. As shown, the fiber optic may be a an individual fiber or even a bundle of similar or dissimilar fibers. In one embodiment, the housing may include two larger cylinders concentric with a smaller cylinder. This shape permits the device (as a rigid or semi-rigid body) to be integrated into a sheet or band (e.g., a rubber cap) to hold the probe close to the subject's head. In one exemplary embodiment, the device includes a recess (shown) or protrusion (not shown) engages with a hole or other feature of a sheet, cap, or band so as to maintain the device in place.

The device suitably includes a lens, as shown. The lens may be rounded or otherwise featured so as to more comfortable engage with the subject. The device may also include a feature (e.g., rounded projection) between the lens and the subject. An optical element (e.g, lens, prism, mirror, fiber, and the like) may be present within the device so as to place various components into optical communication with one another.

The structural enclosure suitably contains various optical components of the devices. The enclosure may be cylindrical as shown in FIG. 16, but may be of any configuration needed. The enclosure may have a cross-section in the range of from about 1 mm to about 50 mm, or in the range of from about 5 mm to about 25 mm. The devices may include a spring, elastomer, or other element configured to maintain pressure between the device and a subject.

Additional Disclosure, Simulations, and In Vivo Results

As described elsewhere herein, the Modified Beer-Lambert law for DOS/NIRS is readily derived from the first order Taylor expansion of the optical density: $OD \approx OD^0 + (\partial OD^0/\partial \mu_a)\Delta\mu_a + (\partial OD^0/\partial \mu'_s)\Delta\mu'_s$, wherein the partial derivatives are evaluated in the "baseline" state ($\mu_a = \mu_a^0$, $\mu'_s = \mu'^0_s$), $OD^0 \equiv -\log[I^0/I_s]$ is the baseline optical density, and the differential changes in absorption and scattering are denoted by $\Delta\mu_a \equiv \mu_a(t) - \mu_a^0$ and $\Delta\mu'_s \equiv \mu'_s(t) - \mu'^0_s$, respectively. Note that the superscript "0" indicates baseline. Within this approximation, the change in optical density is $$\Delta OD = -\log\left(\frac{I(t)}{I^0}\right) \approx \langle L \rangle \Delta\mu_a(t) + \left(\frac{\mu_a^0}{\mu'^0_s}\right)\langle L \rangle \Delta\mu'_s(t) \approx \langle L \rangle \Delta\mu_a(t). \quad (1)$$

Here, $\langle L \rangle \equiv \partial OD^0/\partial \Xi_a$ is the so-called differential pathlength factor, which is approximately the mean pathlength that diffusing photons travel from source to detector (i.e., through the medium). While the traditional Beer-Lambert law relates absolute optical densities to absolute absorption coefficients, the Modified Beer-Lambert law (Eq. (1) in this section of the disclosure) relates differential changes in the optical density to differential changes in the absorption coefficient.

The method disclosed here provides a Modified Beer-Lambert law for measurement of blood flow based on the DCS/DOS technique. The methods relate measured changes in a "DCS optical density" to changes in tissue blood flow, tissue scattering, and tissue absorption. Because the diffusion equation for the DCS signal, more specifically the so-called correlation diffusion equation, is sensitive to the movement of red blood cells in tissue microvasculature, the disclosed methods differ from previous efforts. This disclosure provides exemplary results for measurement of flow changes in any geometry, including specific expressions for two commonly used approximations for tissue models: homogeneous semi-infinite turbid media and two-layer turbid media. The disclosed approach is demonstrated by reference to simulations and an in vivo experiment. The disclosed methods will lead to improvements in characterization of cerebral flow and metabolism, with concomitant clinical impact.

Diffuse Correlation Spectroscopy

As mentioned elsewhere herein, diffuse correlation spectroscopy (DCS) uses NIR light to noninvasively measure tissue blood flow. The DCS blood flow index has been successfully validated against a plethora of 'gold-standard' techniques.

DCS detects tissue blood flow using speckle correlation techniques. It measures the temporal intensity fluctuations of coherent NIR light that has scattered from moving particles (red blood cells) in tissue (FIG. 8A). These temporal fluctuations (FIG. 8B) are quantified by computing the normalized intensity temporal auto-correlation function at multiple delay-times, i.e., one may compute $g_2(\tau) \equiv \langle I(t)I(t+\tau)\rangle/\langle I(t)\rangle^2$, where $I(t)$ is the intensity of the detected light, and the angular brackets, $\langle \ \rangle$, represent time-averages. Formally, the transport of temporal field fluctuations through turbid media is modelled by the so-called correlation diffusion equation, and the decay of the detected autocorrelation function determines a tissue blood flow index (FIG. 8C).

The correlation diffusion equation models the transport of the electric field auto-correlation function, $G_1(\tau) \equiv \langle E^*(t) \cdot E(t+\tau) \rangle$, and it can be solved analytically or numerically for tissue geometries of interest. The normalized electric field auto-correlation function, $g_1(\tau) = G_1(\tau)/G_1(\tau=0)$, is related to the measured (normalized) intensity auto-correlation function via the Siegert relation: $g_2(\tau) = 1 + \beta|g_1(\tau)|^2$, where $\beta$ is a constant determined primarily by the collection optics of the experiment.

As one example, for the simple case of point illumination and detection of homogenous semi-infinite turbid media (FIG. 8A) with tissue absorption coefficient tissue reduced scattering coefficient $\mu'_s$, and tissue blood flow index F, the solution to the correlation diffusion equation is:

$$G_1(\tau) = \frac{3}{4\pi \ell_{tr}} \left[ \frac{\exp(-K(\tau)r_1)}{r_1} - \frac{\exp(-K(\tau)r_b)}{r_b} \right]. \quad (2)$$

Here, $K(\tau) = [3\mu_a(\mu_a+\mu'_s)(1+2\mu'_s k_0^2 F\tau/\mu_a)]^{1/2}$, $r_1 = (l_{tr}^2+\rho^2)^{1/2}$, and $r_b = [(2z_b+l_{tr})^2+\rho^2]^{1/2}$, wherein $\rho$ is the source detector separation and $l_{tr} = 1/(\mu_a+\mu'_s)$ is the photon transport mean-free path through tissue. Further, $k_0 = 2\pi n/\lambda$ is the magnitude of the light wave vector in the medium, and $z_b = 2l_{tr}(1+R_{eff})/(3(1-R_{eff}))$, where $R_{eff}$ the effective reflection coefficient to account for the mismatch between the index of refraction of tissue (n) and the index of refraction of the non-scattering medium bounding tissue ($n_{out}$), e.g., air.

One approach for blood flow monitoring with DCS in this geometry is to derive $g_1(\tau)$ from measurements of $g_2(\tau)$ via the Siegert relation. Then, the semi-infinite correlation diffusion solution (Eq. (2)) is fit using a nonlinear minimization algorithm to $g_1(\tau)$ in order to obtain an estimate of the blood flow index.

Modified Beer-Lambert Law for Flow

Here is provided a "Modified Beer-Lambert law" for tissue blood flow based on the DCS measurement. The first step in this process is to define a DCS optical density (analogous to the DOS/NIRS OD). For source-detector separation $\rho$ and delay-time $\tau$ we define the DCS optical density as: $OD_{DCS}(\tau,\rho) \equiv -\log(g_2(\tau,\rho)-1)$. In addition to delay time and source-detector separation, the DCS optical density also implicitly depends on tissue absorption, scattering, and blood flow (e.g, Eq. (2) in this section).

DCS Modified Beer-Lambert Law for Homogeneous Tissue

One may begin by deriving a general expression for homogeneous tissue, characterized by a blood flow index, F, an absorption coefficient, $\mu_a$, and a reduced scattering coefficient, $\mu'_s$. The DCS Modified Beer-Lambert law is derived by truncating the Taylor series expansion of the DCS optical density to first order in F, $\mu_a$, and $\mu'_s$, i.e., $$OD_{DCS}(\tau,\rho) \approx \quad (3)$$
$$OD_{DCS}^0(\tau,\rho) + \frac{\partial OD_{DCS}^0}{\partial F}\Delta F + \frac{\partial OD_{DCS}^0}{\partial \mu_a}\Delta\mu_a + \frac{\partial OD_{DCS}^0}{\partial \mu'_s}\Delta\mu'_s.$$

Here, $OD_{DCS}^0(\tau,\rho) \equiv -\log(g_2^0(\tau,\rho)-1)$ is the "baseline" (i.e., time t=0) DCS optical density with a baseline blood flow index $F^0$ and with baseline optical properties and $\mu_a^0$ and $\mu'_s{}^0$. Correspondingly, $OD_{DCS}(\tau,\rho) \equiv -\log(g_2(\tau,\rho)-1)$ is the DCS optical density for the intensity auto-correlation function in the "perturbed" state (i.e., time t) with blood flow index F and with optical properties $\mu_a$ and $\mu'_s$. Hence, the differential changes from baseline of tissue blood flow, absorption, and scattering are $\Delta F = F - F^0$, $\Delta\mu_a = \mu_a - \mu_a^0$, and $\Delta\mu'_s = \mu'_s - \mu'_s{}^0$, respectively.

Comparing Eq. (3) from this section with Eq. (1) from this section, the DCS analogues of the differential pathlength are $d_F(\tau,\rho) \equiv \partial OD_{DCS}^0/\partial F$, $d_a(\tau,\rho) \equiv \partial OD_{DCS}^0/\partial \mu_a$, and $d_s(\tau,\rho) \equiv \partial OD_{DCS}^0/\partial \mu'_s$, which can be estimated analytically or numerically with the correlation diffusion model applied to the appropriate geometry (see Appendix 1 below). All three of these weighting factors depend on $\tau$ and $\rho$, on tissue geometry, and on the baseline parameters $F^0$, $\mu_a^0$, and $\mu'_s{}^0$. Rearranging Eq. (3) from this section, we arrive at the DCS Modified Beer-Lambert law for homogeneous tissue:

$$\Delta OD_{DCS}(\tau,\rho) \equiv -\log\left(\frac{g_2(\tau,\rho)-1}{g_2^0(\tau,\rho)-1}\right) \quad (4)$$
$$= d_F(\tau,\rho)\Delta F + d_a(\tau,\rho)\Delta\mu_a + d_s(\tau,\rho)\Delta\mu'_s.$$

Figure 9:
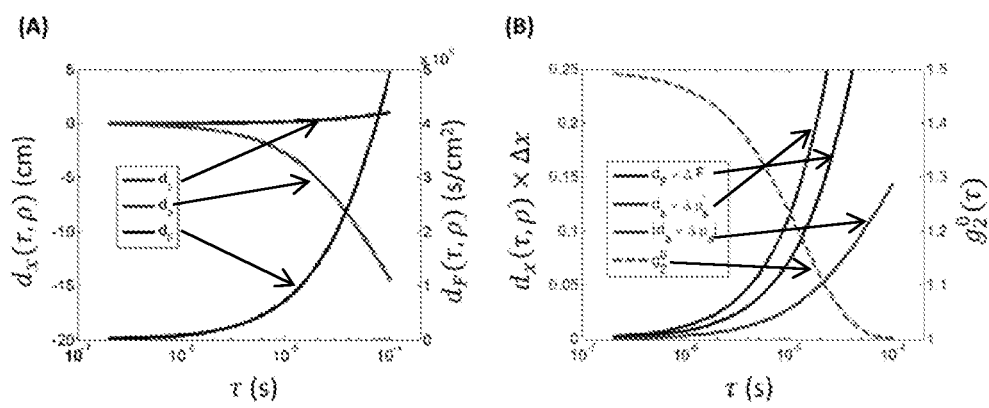
FIG. 9 (A) The semi-infinite multiplicative weighting factors (see Eq. (4)) for tissue scattering ($d_s$), for tissue absorption ($d_a$), and for tissue blood flow ($d_F$, right y-axis). They are plotted as a function of the correlation time, τ, for source-detector separation, ρ=3 cm, and optical wavelength, λ=785 nm, given a typical set of cerebral tissue properties, i.e., $\mu_a^0=0.1$ 1/cm, $\mu_s'^0=8$ 1/cm, $F^0=10^{-8}$ cm$^2$/s, n=1.4, $n_{out}=1$. (B) The semi-infinite DCS Modified Beer-Lambert components $d_F(\tau,\tau)\Delta F$, $d_s(\tau,\rho)\Delta\mu_s$, and $|d_a(\tau,p)\Delta\mu_{a,c}|$, plotted as a function of τ for a 10% increase in blood flow, tissue scattering, and tissue absorption, respectively. On the right y-axis is the intensity auto-correlation function, $g_2^0(\tau)$, for β=0.5. Given the same fractional change, the DCS signal is most sensitive to scattering changes, followed by flow changes, and least sensitive to absorption changes.

Without being bound to any single theory, if the blood flow and optical properties change only slightly, then the perturbation in the DCS optical density is small and the first order expansion (Eq. (3)) is a good approximation. Again without being bound to any single theory, larger tissue hemodynamic changes, $\Delta OD_{DCS}$ can still be small for short delay-times. In this limit, $d_F$, $d_a$, and $d_s$ are typically small (FIG. 9). Analytical and numerical computation of the weighting factors ($d_F$, $d_a$, $d_s$) is described in Appendix 1 below.

Eq. (4) is a general, non-limiting result that describes the change in DCS optical density for homogeneous tissue. For a given tissue/measurement geometry, the change in blood flow may be computed by evaluating the weighting factors for the geometry in question, and then substituting in for them in Eq. (4).

DCS Modified Beer-Lambert Law for Homogeneous Semi-Infinite Geometry

Figure 8:
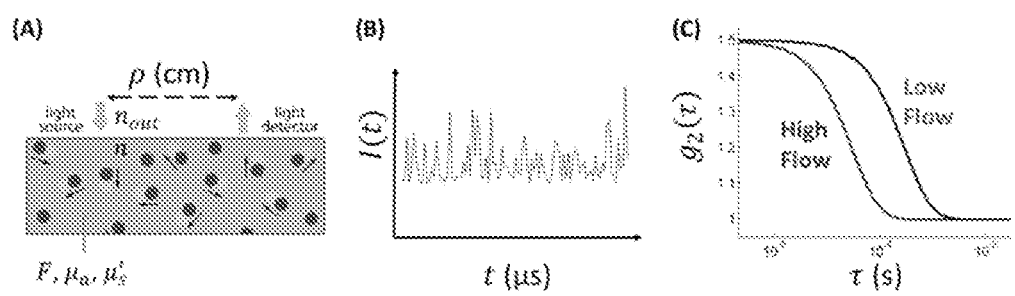
FIG. 8 (A) Schematic for blood flow monitoring in a homogeneous, semi-infinite turbid tissue. Blood cell motion (dark disks at time t, lighter disks at time t+τ) induces temporal fluctuations in the scattered light intensity, I(t), at the light detector (panel B). These intensity fluctuations are characterized by the normalized intensity auto-correlation function ($g_2(\tau)$). (C) The decay of the intensity auto-correlation function curves is related to tissue blood flow.

One may evaluate weighting factors in Eq. (4) for the special case of the homogeneous semi-infinite geometry (FIG. 8). From Eq. (2), the normalized electric field auto-correlation function is $$g_1(\tau,\rho) = \frac{\exp(-K(\tau)r_1)/r_1 - \exp(-K(\tau)r_b)/r_b}{\exp(-K_0 r_1)/r_1 - \exp(-K_0 r_b)/r_b}, \quad (5)$$

where $K(\tau)$, $r_1$, and $r_b$ are as defined in Section 2, and $K_0 = K(\tau=0) = [3\mu_a(\mu_a+\mu'_s)]^{1/2}$. The multiplicative weighting factors in the semi-infinite geometry can be computed from substituting Eq. (5) into Eqs. (11) and (12), e.g., $$d_F(\tau,\rho) = \quad (6)$$
$$\frac{6\mu'_s{}^0(\mu'_s{}^0 + \mu_a^0)k_0^2\tau}{K^0(\tau)} \left[ \frac{\exp(-K^0(\tau)r_1^0) - \exp(-K^0(\tau)r_b^0)}{\exp(-K^0(\tau)r_1^0)/r_1^0 - \exp(-K^0(\tau)r_b^0)/r_b^0} \right].$$

In FIG. 9, $d_F$, $d_a$, and $d_s$ for the semi-infinite geometry are plotted as a function of $\tau$ using typical tissue properties. The three weighting factors are smaller in magnitude for shorter delay-times. The weighting factor for absorption is negative, i.e., an increase in absorption shifts the intensity autocorrelation function to the right (compared to baseline), and vice versa for increases in flow and scattering.

Because the weighting factors are smaller at shorter delay-times (FIG. 9), the DCS optical density perturbation will also be smaller, which in turn means higher accuracy in the DCS Modified Beer-Lambert law (Eq. (4)). In the semi-infinite geometry, the delay-times used for Eq. (4) should satisfy the limits $2\mu'_s k_0^2 F\tau/\mu_a \square 1$ and $2\mu'_s{}^0 k_0^2 F^0\tau/\mu_a{}^0 \square 1$ for the most quantitatively accurate results (see Appendix 2 below). One exemplary, non-limiting "rule of thumb" for accurately using Eq. (4) is to utilize data wherein $g_1^0(\tau) > 0.5$.

FIG. 9B shows that for the same fractional changes (10%) in flow, scattering, and absorption, the change in DCS optical density is greatest due to scattering, followed by flow; changes in absorption had the least influence on the DCS signal. In practice, concurrent frequency-domain or time-domain NIRS/DOS may be employed to directly measure tissue absorption and scattering and account for their effects (i.e., if these parameters change). Note however, tissue scattering changes that accompany hemodynamic concentration variation are often negligible, since the origin of tissue scattering is predominantly from interfaces between cells and the extracellular space or between cellular cytoplasm and cellular organelles.

DCS Modified Beer-Lambert Law for Heterogeneous Geometries

Tissue may be approximated to be optically homogeneous for hemodynamic monitoring; this approach has the advantage of simplicity. Considering tissue as heterogeneous, the tissue contains multiple compartments with different optical properties due to blood vessels, fat, and bone. These regions can be modeled as "layers" below the tissue surface such as scalp, skull and cortex.

Under these conditions, one may use a Taylor series expansion of the DCS optical density to derive the DCS Modified Beer-Lambert law for heterogeneous media. Assuming for purposes of explanation that the heterogeneous tissue can be discretized into N homogeneous regions, the first-order Taylor series expansion is $$OD_{DCS}(\tau, \rho) \approx OD_{DCS}^0(\tau, \rho) + \qquad (7)$$

$$\sum_{k=1}^{N}\left[\frac{\partial OD_{DCS}^0}{\partial F_k}\Delta F_k + \frac{\partial OD_{DCS}^0}{\partial \mu_{a,k}}\Delta \mu_{a,k} + \frac{\partial OD_{DCS}^0}{\partial \mu'_{s,k}}\Delta \mu'_{s,k}\right].$$

Here, $F_k$, $\mu_{a,k}$, and $\mu'_{s,k}$ denote the blood flow index, tissue absorption, and tissue scattering for the $k^{th}$ homogeneous region in the tissue, respectively, and $\Delta F_k \equiv F_k - F_k^0$, $\Delta\mu_{a,k} \equiv \mu_{a,k} - \mu_{a,k}^0$, and $\Delta\mu'_{s,k} \equiv \mu'_{s,k} - \mu'_{s,k}^0$ denote the changes in these parameters from baseline. Rearranging Eq. (7), the DCS Modified Beer-Lambert law for heterogeneous media is:

$$-\log\left(\frac{g_2(\tau, \rho) - 1}{g_2^0(\tau, \rho) - 1}\right) \approx \qquad (8)$$

$$\sum_{k=1}^{N}[d_{F,k}(\tau, \rho)\Delta F_k + d_{a,k}(\tau, \rho)\Delta\mu_{a,k} + d_{s,k}(\tau, \rho)\Delta\mu'_{s,k}],$$

where $\{d_{F,k} \equiv \partial OD_{DCS}^0/\partial F_k,\ d_{a,k} \equiv \partial OD_{DCS}^0/\partial \mu_{a,k},\ d_{s,k} \equiv \partial OD_{DCS}^0/\partial \mu'_{s,k}\}$ are DCS analogues of the partial pathlengths from DOS/NIRS. These multiplicative weighting factors depend on tissue geometry, on the baseline tissue properties, i.e., $\{F_k^0, \mu_{a,k}^0, \mu'_{s,k}^0\}$ and on $\tau$ and $\rho$. They account for the relative importance of the various regional hemodynamic changes in the DCS optical density perturbation, and they can be estimated in the same manner as described in Appendix 1 herein.

Modified Beer-Lambert Law for Two-Layer Media

Figure 10:
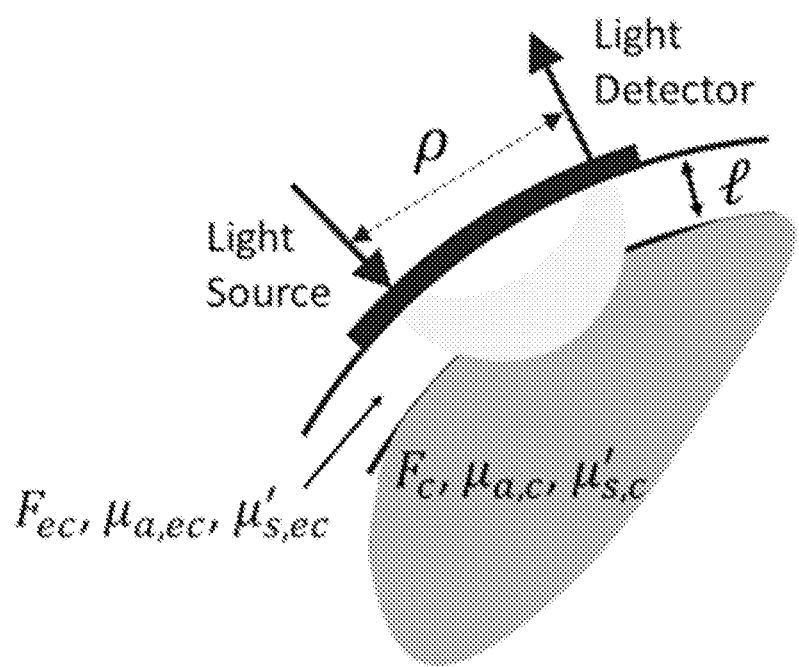
FIG. 10: An exemplary two-layer tissue geometry.

The simplest heterogeneous model for tissue is the two-layer geometry, which is an important special case (FIG. 10). For cerebral applications, the two-layer geometry is comprised of a semi-infinite bottom layer (i.e., corresponding to the cortical regions of the brain) with a distinct blood flow index, absorption coefficient, and scattering coefficient of $F_c$, $\mu_{a,c}$, and $\mu'_{s,c}$, respectively, and a superficial top layer (i.e., corresponding to extra-cerebral scalp and skull tissue) with thickness, and distinct tissue properties denoted by $F_{ec}$, $\mu_{a,ec}$, and $\mu'_{s,ec}$.

The two-layer DCS Modified Beer-Lambert law is the special case of Eq. (8) for N=2 homogeneous regions, i.e., $$\Delta OD_{DCS}(\tau, \rho) = -\log\left(\frac{g_2(\tau, \rho) - 1}{g_2^0(\tau, \rho) - 1}\right) \qquad (9)$$

$$\approx d_{F,c}(\tau, \rho)\Delta F_c + d_{F,ec}(\tau, \rho)\Delta F_{ec} + d_{a,c}(\tau, \rho)\Delta\mu_{a,c} +$$

$$d_{a,ec}(\tau, \rho)\Delta\mu_{a,ec} + d_{s,c}(\tau, \rho)\Delta\mu'_{s,c} + d_{s,ec}(\tau, \rho)\Delta\mu'_{s,ec}.$$

Figure 11:
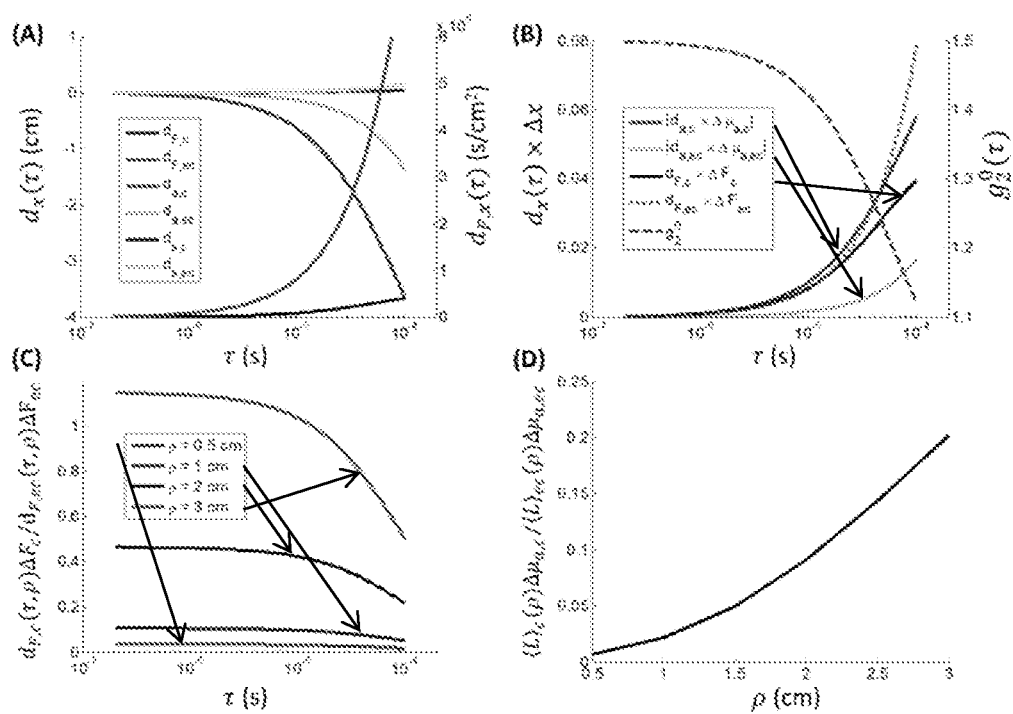
FIG. 11: (A) The two-layer multiplicative weighting factors (see Eq. (9)) for $d_{F,c}$ and $d_{F,ec}$ (right y-axis); and for $d_{a,c}$, $d_{a,ec}$, $d_{s,c}$, and $d_{s,ec}$. The lines are in ascending dx(t) values at $t=10^{-5}$, i.e., $d_{F,c}$ at the bottom, $d_{F,ec}$; $d_{a,c}$, $d_{a,ec}$, $d_{s,c}$, $d_{s,ec}$. They are plotted as a function of the correlation time, τ, for source-detector separation, ρ=3 cm, and optical wavelength, λ=785 nm, given a set of typical extra-cerebral and cerebral tissue properties, i.e., $\mu_{a,ec}^0=0.16$, $\mu_{a,c}^0=0.12$, $\mu'_{s,c}^0=6$, $\mu'_{s,ec}^0=10$ 1/cm; $F_c^0=10^{-8}$, $F_{ec}^0=10^{-9}$ cm$^2$/s; $_{l=1}$ cm, n=1.4, and $n_{out}=1$. (B) The two-layer DCS Modified Beer-Lambert components $d_{F,c}\Delta F_c$, $d_{F,ec}\Delta F_{ec}$, $|d_{a,c}\Delta\mu_{a,c}|$, and $|d_{a,ec}\Delta\mu_{a,ec}|$, plotted as a function of $\tau$ for a 10% increase in each parameter. On the right y-axis is the intensity auto-correlation function, $g_2^0(\tau)$, for $\beta=0.5$. Notice that at shorter delay-times for $\rho=3$ cm, the change in DCS optical density is about equally sensitive to changes in cerebral blood flow, extra-cerebral blood flow, and cerebral absorption. The change in DCS optical density is less sensitive to changes in extra-cerebral absorption. (C) The ratio of the cerebral (c) and extra-cerebral (ec) flow components in the DCS optical density perturbation, $\Delta OD_{DCS}(\tau)$ (Eq. (9)), for 4 separations, $\rho=0.5$, 1, 2, and 3 cm. They are plotted as a function of $\tau$ for a 10% increase in cerebral and extra-cerebral blood flow. For the shorter separations of 0.5 and 1 cm, the ratio is substantially less than one, indicating that the DCS optical density is predominantly sensitive to the extra-cerebral layer. At the 3 cm separation, the DCS optical density is slightly more sensitive to cerebral blood flow than extra-cerebral blood flow at the short delay-times, i.e., the ratio is greater than one. However, at longer delay-times, the ratio decreases, and the DCS optical density becomes more sensitive to extra-cerebral blood flow. (D) The ratio of the cerebral and extra-cerebral absorption components in the two-layer Modified Beer-Lambert law for NIRS, plotted as a function of $\rho$ for a 10% increase in cerebral and extra-cerebral absorption. $\langle L\rangle_c$ and $\langle L\rangle_{ec}$ are the cerebral and extra-cerebral partial pathlengths. One may see from panels (B) and (C) that the DCS optical density is more sensitive to the cerebral layer than the NIRS optical density is.

Again, the multiplicative weighting factors $d_{F,i} \equiv \partial OD_{DCS}^0/\partial F_i$, $d_{a,i} \equiv \partial OD_{DCS}^0/\partial \mu_{a,i}$, and $d_{s,i} \equiv \partial OD_{DCS}^0/\partial \mu'_{s,i}$ (with subscript i denoting c (cerebral) or ec (extra-cerebral)), indicate the relative sensitivity of the DCS optical density to cerebral versus extra-cerebral hemodynamic changes. The parameters depend on delay-time $\tau$, source-detector separation $\rho$, extra-cerebral layer thickness l, and baseline tissue properties $F_c^0$, $F_{ec}^0$, $\mu_{a,c}^0$, $\mu_{a,ec}^0$, $\mu'_{s,c}^0$, and $\mu'_{s,ec}^0$. They can be computed by numerically taking the appropriate derivatives of the two-layer solution to the correlation diffusion equation:

$$g_1(\tau) = G_1(\tau)/G_1(0),$$

$$G_1(\tau) = \frac{1}{2\pi}\int_0^\infty \tilde{G}_1(\tau)sJ_0(s\rho)ds,$$

$$\tilde{G}_1(\tau) =$$

$$\frac{\sinh(\kappa_{ec}(z_b + z_0))}{D_{ec}\kappa_{ec}}\frac{D_{ec}\kappa_{ec}\cosh[\kappa_{ec}\ell] + D_c\kappa_c\sinh[\kappa_{ec}\ell]}{D_{ec}\kappa_{ec}\cosh[\kappa_{ec}(\ell + z_b)] + D_c\kappa_c\sinh[\kappa_{ec}(\ell + z_b)]} -$$

$$\frac{\sinh[\kappa_{ec}z_0]}{D_{ec}\kappa_{ec}},$$

where $D_i = 1/[3(\mu'_{s,i} + \mu_{a,i})]$, $\kappa_i^2 = (D_i s^2 + \mu_{a,i}k_0^2 F_i\tau)/D_i$, $z_b = D_{ec}(1+R_{eff})/(1-R_{eff})$, $z_0 = 3D_{ec}$, and $R_{eff}$ and $k_0$ are defined as set forth elsewhere herein. For illustration purposes, this solution assumes that the top and bottom layers are (refractive) index-matched. The two-layer weighting factors for a typical set of extra-cerebral/cerebral tissue properties are plotted in FIG. 11. Importantly, for a source-detector separation $\rho=3$ cm, the change in the DCS optical density is more sensitive to changes in flow and absorption in the cerebral layer rather than in the extra-cerebral layer (except for very long delay-times). This sensitivity is especially prominent at the shorter delay-times (FIGS. 11B, 11C). These differences may arise because of the difference in magnitude of cerebral versus extra-cerebral flow (e.g., cerebral flow is approximately 10 times faster than extra-cerebral flow).

The increase in the influence of the extra-cerebral layer at longer delay times (FIG. 11C) may be explained by consideration of the pathlengths of light and their association with short versus long correlation decay times τ. Briefly, in the auto-correlation decay function, long light paths contribute rapid decays to the signal (short τ) and short light paths contribute slow decays to the signal (large τ). At short source-detector separations, e.g., ρ=0.5 cm, which mostly sample the superficial layer, the DCS optical density perturbation is predominantly sensitive to the superficial layer (FIG. 11C). In agreement with Selb et al, a comparison of FIGS. 11C and 11D reveals that the DCS optical density is more sensitive to cerebral changes than the DOS/NIRS optics density. Again, this is largely because cerebral blood flow is much greater than extra-cerebral blood flow, and because DCS is effectively a time resolved technique that permits separation of long light paths (shorter delay-times) from short light paths (longer delay-times).

Validation with Simulated Data

Figure 12:
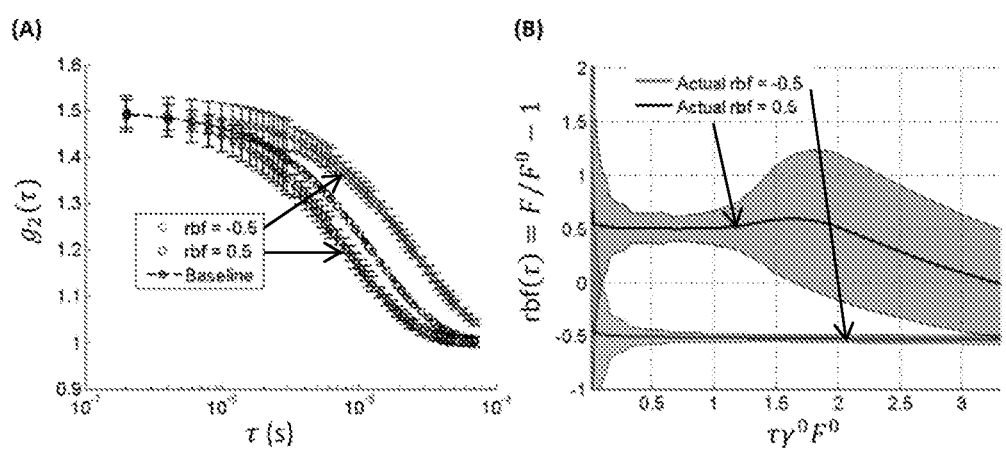
FIG. 12: (A) Simulated semi-infinite intensity auto-correlation curves (mean±SD across N=10 k curves) plotted as a function of the delay-time $\tau$ for a −50% and 50% change in flow while tissue optical properties were held constant. The source-detector separation, light wavelength, and baseline tissue properties are $\rho=3$ cm, $\lambda=785$ nm, and $\mu_a^0=0.1$ 1/cm, $\mu'_s^0=8$ 1/cm, $F^0=10^{-8}$ cm$^2$/s, n=1.4, $n_{out}=1$, respectively. The simulated DCS data were generated from applying a correlation noise model to the semi-infinite solution of the correlation diffusion equation (Eq. (5)). The correlation noise model was evaluated at a baseline DCS intensity of 50 k photons a second and an averaging time of 2.5 seconds. (B) Fractional blood flow changes (mean±SD) estimated by applying the semi-infinite DCS Modified Beer-Lambert law, i.e., rbf$(\tau)=\Delta OD_{DCS}(\tau)/(d_F(\tau)F^0)$ (Eq. (4)), to the simulated data. To appreciate the simulated results more generally, these fractional blood flow changes are plotted against the dimensionless delay-time $\tau\gamma^0 F^0$. $(\gamma^0 F^0)^{-1}$, wherein $\gamma\equiv K_0(\mu'_s/\mu_a)(k_0)^2 r_1$ (see Eq. (17)), is approximately the characteristic decay time of the baseline electric field auto-correlation function (see Appendix 2).

The semi-infinite DCS Modified Beer-Lambert law (Eq. (4)) was tested using simulated data (FIG. 12). The simulated DCS data was generated from semi-infinite analytical solutions of the correlation diffusion equation (Eq. (5)) with added noise. Baseline tissue blood flow and optical properties in the simulated data were chosen to be representative of the head, and perturbations from baseline were induced by varying blood flow (F) from +50% to −50%, with constant tissue optical properties. FIG. 12A shows the simulated intensity auto-correlation functions for these baseline and perturbed conditions, plotted as a function of delay-time. The DCS Modified Beer-Lambert law (Eq. (4)) was applied to this simulated data set to calculate the flow change as a function of delay-time (FIG. 12B). There is good agreement between the calculated and actual flow changes for a wide range of delay-times.

To quantify this range of delay-times for which the DCS Modified Beer-Lambert law can be accurately employed, the semi-infinite DCS Modified Beer-Lambert law is expected to be accurate in the limit $2\mu'_s k_0^2 F\tau/\mu_a \Box 1$ (Appendix 2 below). Modeling shows that it will remain fairly accurate even when $2\mu'_s k_0^2 F\tau/\mu_a \sim 1$. To appreciate the simulation results more generally, we introduce the dimensionless delay-time, $\tau\gamma^0 F^0$, which depends on baseline blood flow ($F^0$), correlation time-delay (τ), and $\gamma^0 \equiv K_0^0(\mu'^0_s/\mu_a^0)k_0^2 r_1^0$ (Eq. (17)); when this dimensionless delay-time is ~1, the baseline field correlation function has decayed by ~1/e. In terms of this dimensionless delay-time, the limit $2\mu'_s k_0^2 F\tau/\mu_a \Box 1$ corresponds to the baseline condition $\tau\gamma^0 F^0 \Box \alpha$, where $\alpha \equiv \gamma^0 \mu_a^0 (2\mu'^0_s k_0^2)$. For the "typical" conditions chosen for FIG. 12, α=2.34.

FIG. 12B indicates the difference (error) between the calculated DCS Modified Beer-Lambert flow change (estimated for each dimensionless delay-time) and the true flow change (simulated value). This error is relatively small, even for dimensionless delay-times approaching α=2.34. Once the auto-correlation curves are close to fully decayed, the DCS Modified Beer-Lambert law is predominantly sensitive to correlation noise instead of flow changes. For a perturbed state from baseline (e.g., rbf=50%), the limit $2\mu'_s k_0^2 F\tau/\mu_a \Box 1$ corresponds to $\tau\gamma^0 F^0 \Box \alpha(F^0/F)$ (assuming constant optical properties). The greater F is, the smaller the upper limit on the dimensionless delay-time time will be.

Noise Consideration

At very short delay-times, there is little difference between the intensity auto-correlation curves at different blood flows (FIG. 12A). Consequentially, the changes to the DCS optical density in this limit are heavily influenced by correlation noise. Hence the flow calculations at the very short delay-times in FIG. 12B are noisy. In general, from applying error propagation rules to Eq. (4), the noise in the calculated flow change as a function of τ for constant tissue optical properties is $$\delta(rbf(\tau)) - \frac{1}{d_F(\tau)F_0}\delta(\Delta OD_{DCS}(\tau)) = \frac{1}{d_F(\tau)F_0}\frac{\delta(g_2(\tau)-1)}{|g_2(\tau)-1|}. \quad (10)$$

A correlation noise model can be used to accurately model $\delta(g_2(\tau)-1)$. As τ increases, the correlation noise decreases and $d_F(\tau)F_0$ increases (FIG. 9A). Both of these trends reduce the noise in rbf. However, when $|g_2(\tau)-1|$ goes to zero as τ increases, a concurrent increase in noise is expected. From FIG. 12B, the noise in rbf falls with increasing delay-time and then levels off around $\tau\gamma^0 F^0 \approx 0.3$; the noise then remains constant for a large range of delay-times.

Figure 13:
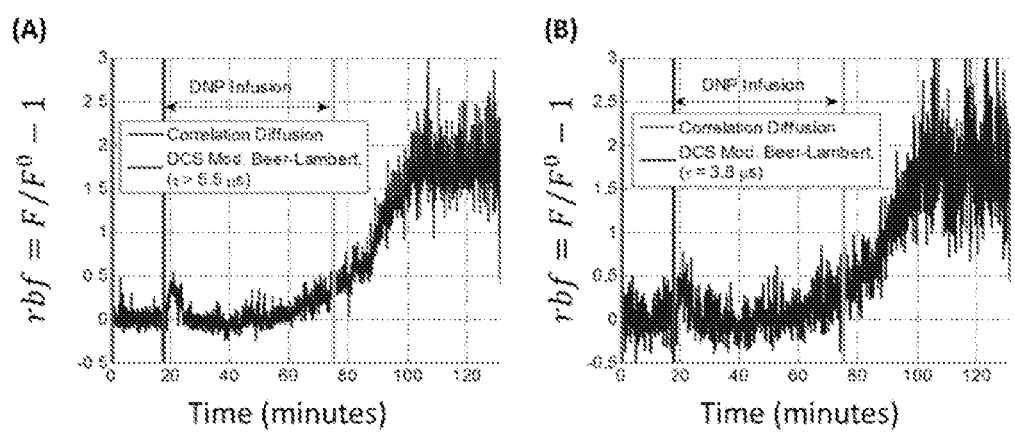
FIG. 13: Temporal fractional cerebral blood flow changes induced by injection of the drug dinitrophenol (DNP) in a juvenile pig. The baseline flow is $F^0=5.34\times10^{-8}$ cm$^2$/s, which is the average blood flow index over the 18 minute time interval between the vertical red lines. Cerebral blood flow changes were calculated from nonlinear fits to the semi-infinite correlation diffusion solution (Eq. (5)) and from the semi-infinite DCS Modified Beer-Lambert law (Eq. (4)) using (A) multiple delay-times, i.e., $\tau>5.5$ μs, which corresponds to $g_2^0(\tau)>1.25$, and (B) a single delay-time, i.e., $\tau=3.8$ μs, which corresponds to $g_2^0(\tau)=1.3$. Measured tissue absorption changes (FIG. 7B) were incorporated in both the correlation diffusion fit and the DCS Modified Beer-Lambert law. Tissue scattering was assumed to remain constant at $\mu'_s=8$ cm$^{-1}$.
Figure 14:
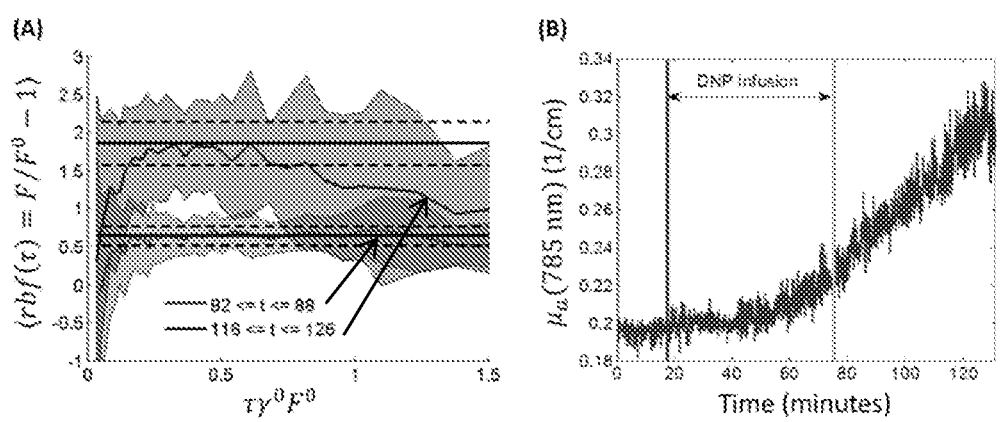
FIG. 14: (A) Fractional cerebral blood flow changes (Mean±SD; averaged across indicated time intervals in the legend) as a function of the dimensionless delay-time $\tau\gamma^0 F^0$ (see FIG. 5 caption) in a juvenile pig. (B) The pig's cerebral absorption over time, which was calculated from applying the semi-infinite Modified Beer-Lambert law (Eq. (1)) to the measured NIRS intensity changes from baseline. The cerebral blood flow changes in panel (A) were obtained from applying the semi-infinite DCS Modified Beer-Lambert law to the measured intensity auto-correlation curves and the measured cerebral absorption changes. The horizontal solid and dashed black lines in panel (A) indicate the fractional blood flow changes (Mean±SD) obtained from fits to the non-linear semi-infinite correlation diffusion solution.

As one would expect, the flow change computed with a single τ in the DCS Modified Beer-Lambert law is more sensitive to correlation noise than the flow change extracted from nonlinear fits to the semi-infinite correlation diffusion solution across many delay-times (see FIGS. 13, 14). To reduce sensitivity to noise, multiple delay-times can also be used for the DCS Modified Beer-Lambert law. Eq. (4) then becomes a system of linear equations; one equation for each delay-time, which can very rapidly be solved for the flow change.

In Vivo Validation

The semi-infinite DCS Modified Beer-Lambert law was also validated in vivo on a juvenile pig (FIGS. 13-14). The scalp of the juvenile pig was reflected and 2.5-mm burr holes were drilled through the skull down to the dura. Optical fibers were inserted into the holes to form one DCS source-detector pair to measure cerebral blood flow and one NIRS source-detector pair to measure cerebral tissue absorption. The source-detector separations of both pairs were approximately 1.5 cm, and the baseline cerebral optical properties of the pig were assumed to be $\mu_a^0$(785 nm)=0.2 cm$^{-1}$ and $\mu'^0_s$ (785 nm)=8 cm$^{-1}$. In this measurement, the semi-infinite geometry is a good approximation of the tissue geometry because the optical fibers are very close to the brain.

A 200% increase in cerebral blood flow was induced in the pig via venous infusion of 9 mg/kg of the drug dinitrophenol (DNP). DNP is a proton transporter across cell membranes, which disrupts the mitochondrial proton gradient. In an effort to restore the proton gradient, cells heavily stimulate cerebral oxygen metabolism, which in turn leads to a large increase in cerebral blood flow.

The calculated temporal cerebral blood flow changes in the pig from DNP using the DCS Modified Beer-Lambert law are in good agreement with the calculated changes from nonlinear fits to the semi-infinite solution of the correlation diffusion equation (FIG. 13). Measured cerebral absorption changes (FIG. 14B) were incorporated in the blood flow calculations. Note that when using multiple delay-times in the DCS Modified Beer-Lambert law, the noise in temporal blood flow estimates is comparable to the nonlinear diffusion fit (FIG. 13A). For single z blood flow monitoring, the temporal blood flow noise is larger, but the average blood flow changes are the same (FIG. 13B), which demonstrates the feasibility of accurate single τ blood flow monitoring with DCS. In FIG. 13B, $\tau\gamma^0 F^0$=0.33 (corresponding to $g_2^0(\tau)$=1.30) was used for single delay-time monitoring.

The estimated cerebral blood flow changes in the pig from the DCS Modified Beer-Lambert law are also plotted as a function of dimensionless delay-time in FIG. 14A for two quasi steady-state temporal intervals. During these temporal flow intervals, the blood flow changes were also determined from nonlinear fits to the semi-infinite correlation diffusion solution. The average blood flow changes from the nonlinear fit estimates are 185% and 64% (solid black lines). The horizontal dashed lines in FIG. 14A indicate the noise in the nonlinear fit estimates of blood flow (constant because the nonlinear correlation diffusion fit uses all delay-times). Interestingly, although estimates of blood flow changes obtained from the DCS Modified Beer-Lambert law are noisy, the average value of these estimates are within the noise of the nonlinear correlation diffusion fit estimates for the delay-time interval $0.16 < \tau \gamma^o F^o < 0.82$, which corresponds to the baseline intensity auto-correlation function range $1.15 < g_2^o(\tau) < 1.40$.

Discussion

This disclosure extends a new approach to DCS measurement and demonstrates the accuracy of this extension in both simulations (FIG. 12) and in vivo data (FIGS. 13, 14). As with the Modified Beer-Lambert approach, the DCS Modified Beer-Lambert approach has advantages compared to the traditional approach of fitting intensity auto-correlation data to nonlinear solutions of the correlation diffusion equation.

Real-Time Estimates of Blood Flow Changes

The DCS Modified Beer-Lambert law is a linear equation relating changes in blood flow to changes in signal for any tissue geometry. Although the correlation diffusion solution in the semi-infinite geometry is closed form, the correlation diffusion solutions in more intricate geometries (e.g., curved, layered) are vastly more complex, and consequentially quite time-consuming when fitting data. With the DCS Modified Beer-Lambert approach, the correlation diffusion solutions are needed only once, in order to evaluate the multiplicative weighting factors at the "baseline" tissue state, e.g., Eq. (13). Then, blood flow changes from baseline are rapidly determined by solving a linear equation (Eq. (4) or (8)). Consequentially, the DCS Modified Beer-Lambert law is well suited for real-time blood flow monitoring, especially in tissue geometries that are not semi-infinite.

Blood Flow Monitoring in Tissues Wherein Light Propagation is Non-Diffusive

Diffusive light transport is not required for using the DCS Modified Beer-Lambert approach. In blood flow monitoring applications wherein the photon diffusion model is not valid, the multiplicative weighting factors can be evaluated using solutions to the correlation transport equation instead of the correlation diffusion equation (see Appendix 1). For the tissue geometry of interest, the correlation transport equation can be solved numerically with Monte Carlo techniques. Thus, the DCS Modified Beer-Lambert approach facilitates accurate blood flow monitoring for the small source-detector separations typical of endoscopic probes or speckle correlation based imaging methods, for complex tissues that contain "non-diffusing" domains such as (arguably) cerebral spinal fluid inside the head, and for tissues that contain very high concentrations of blood, as in the liver. In all three of these examples, the assumptions underlying the photon diffusion model are violated, and therefore the photon diffusion model is not expected to be accurate. Another potential application of the non-diffusive DCS Modified Beer-Lambert approach is blood flow monitoring with visible light.

Improved Depth Sensitivity

The DCS Modified Beer-Lambert law permits blood flow monitoring with intensity auto-correlation measurements at a single delay-time, in contrast to the traditional correlation diffusion approach wherein blood flow estimates are obtained by acquiring and fitting a full intensity auto-correlation curve consisting of many delay-times. It has been well established that the auto-correlation function decay times of long light paths are relatively short, while the decay times of short paths are relatively long. Thus, the auto-correlation function at shorter delay-times will inherently be more sensitive to deeper tissues (FIG. 11), which in turn means that the sensitivity of the DCS measurement to blood flow at deeper tissue depths is improved by using short delay-times in the DCS Modified Beer-Lambert law. Conversely, using long delay-times improves the sensitivity of the DCS measurement to tissue blood flow at shallow depths. This same effect can be achieved by fitting different parts of the intensity auto-correlation curve to the correlation diffusion model. In practice, these correlation diffusion fits still require several delay-times spanning a significant portion of the auto-correlation curve. By using one delay-time, the experimenter has finer control of the measurement depth sensitivity.

Fast DCS Measurement Speed

Importantly, the DCS Modified Beer-Lambert law offers new routes for increased DCS measurement speed and for simpler instrumentation. Underlying these advantages is again the aspect of blood flow monitoring with a single delay-time. We and others have used multiple-tau hardware correlators to measure the intensity auto-correlation function at delay-times spanning several orders of magnitude from ~100 ns to ~10 ms. Achieving sufficient SNR for deep tissue DCS measurements (e.g., as in the brain) typically requires averaging many (N>100) of these 10-ms auto-correlation curves. The single delay-time cerebral blood flow monitoring in the pig shown in FIG. 13B was done at $\tau=3.8$ μs. Thus, in this example, ~250 blood flow measurements can be acquired in 1 ms, which can then be temporally averaged to reduce noise. In 10 ms, which is roughly the time required to measure a single auto-correlation curve with a multiple $\tau$ correlator, ~2500 blood flow measurements can be acquired and averaged. Therefore, even though single $\tau$ blood flow monitoring with the DCS Modified Beer-Lambert law is more sensitive to correlation noise than multiple $\tau$ monitoring (FIGS. 13-14), the substantial improvement in the blood flow sampling rate with single $\tau$ monitoring means that enough averaging can be employed to compensate for this additional noise while still maintaining high DCS measurement speeds. Blood flow measurements at high acquisition rates are advantageous in several applications, including schemes to filter out motion artifacts in exercising muscle. Single $\tau$ monitoring also makes it possible to use single $\tau$ hardware correlators, which are cheaper than multiple $\tau$ hardware correlators. Alternatively, software correlators for a single delay-time can be implemented.

Filtering Out Contamination from Superficial Tissues in Deep Tissue Flow Monitoring Paradigms developed with the Modified Beer-Lambert law to filter out contamination from superficial tissues in blood oxygenation measurements of the tissue of interest (e.g., the brain) can be used in the DCS Modified Beer-Lambert formulation for blood flow monitoring.

One scheme for filtering out superficial tissue contamination in the DCS signal is to use two source-detector separations, one of which is long and the other short. Detected light from the long separation travels through both layers of tissue, but detected light at the short separation is predominantly confined to the superficial layer. The two source-detector separation DCS Modified Beer-Lambert law can be employed to isolate the deep tissue blood flow component in the DCS signal from the superficial blood flow component by acquiring "initial/baseline" measurements wherein only superficial blood flow is changing. In cerebral monitoring, one way to change superficial blood flow without affecting cerebral blood flow is to vary the pressure of the optical probe against the head. Thus, initial measurements acquired during probe pressure modulation can be used to derive the patient-specific weighting factors in the two source-detector separation DCS Modified Beer-Lambert law. These weighting factors are then used to filter out superficial contamination in subsequent cerebral blood flow monitoring.

Low Sensitivity of Blood Flow Monitoring to "Baseline" Tissue Properties

Figure 15:
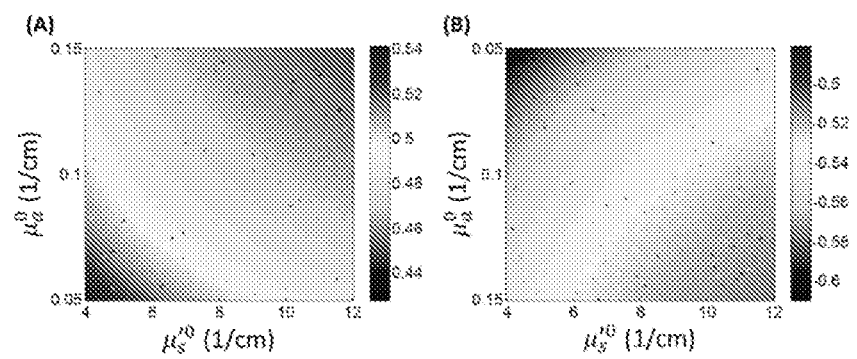
FIG. 15: Fractional blood flow changes (i.e., $F/F^0-1$) computed from applying the semi-infinite DCS Modified Beer-Lambert law (Eq. (4)) with assumed baseline optical properties of $\mu_a^0$ (vertical axis) and $\mu'_s^0$ (horizontal axis) to semi-infinite simulated data with noise. The actual blood flow and absorption changes are (A) 50% and 15%, and (B) −50% and −15%, respectively. Tissue scattering was constant, and the actual baseline properties (including simulated noise parameters) are identical to those in FIG. 5, e.g., $\mu_a^0=0.1$, $\mu'_s^0=8$ cm$^{-1}$. The Modified Beer-Lambert law was used to calculate the absorption change from the simulated light intensity change, wherein the assumed baseline optical properties were used to compute the differential pathlength. The baseline flow index, $F^0$, was extracted from a nonlinear fit of the simulated baseline auto-correlation data to the semi-infinite correlation diffusion solution given the assumed baseline optical properties. Errors in the assumed baseline optical properties only have small effects on the computed fractional flow change.

Implementing the DCS Modified Beer-Lambert law requires knowledge of the baseline tissue properties to evaluate the multiplicative weighting factors. These baseline tissue properties can either be assumed from the literature (e.g.,) or measured with time-domain or frequency-domain NIRS. For typical tissue measurements, the sensitivity in the computed fractional blood flow change to assumed baseline optical properties is small (FIG. 15). Thus, for many applications, errors in the assumed baseline optical properties has little effect on calculated changes in blood flow.

Appendix 1

The multiplicative weighting factors $d_F$, $d_a$, and $d_s$ in Eq. (4) can be estimated by taking the appropriate derivative of the solutions to the correlation diffusion equation applied to the appropriate geometry (e.g., semi-infinite homogeneous, etc.). First, using the Siegert relation, we have:

$$d_F(\tau, \rho) \equiv \frac{\partial}{\partial F}[-\log(g_2^0(\tau, \rho) - 1)] \qquad (11)$$

$$= \frac{\partial}{\partial F}[-\log(\beta[g_1^0(\tau, \rho)]^2)]$$

$$= \frac{\partial}{\partial F}[-\log(\beta) - \log([g_1^0(\tau, \rho)]^2)]$$

$$= 2\frac{\partial}{\partial F}[-\log(g_1^0(\tau, \rho))].$$

Similarly, $$d_a(\tau, \rho) = 2\frac{\partial}{\partial \mu_a}[-\log(g_1^0(\tau, \rho))], \qquad (12)$$

$$d_s(\tau, \rho) = 2\frac{\partial}{\partial \mu_s'}[-\log(g_1^0(\tau, \rho))].$$

Here, $g_1(\tau,\rho)$ is the solution to the correlation diffusion equation for the geometry of interest, and the derivatives of the solution are evaluated at baseline conditions. In conditions where an analytical solution for the correlation diffusion equation does not exist, the multiplicative weighting factors can be computed numerically:

$$d_F(\tau, \rho) = \frac{2}{\Delta F}\log\left(\frac{g_1(\tau, \rho, (F^0 - \Delta F)/2, \mu_a^0, \mu_s'^0)}{g_1(\tau, \rho, (F^0 + \Delta F)/2, \mu_a^0, \mu_s'^0)}\right), \qquad (13)$$

$$d_a(\tau, \rho) = \frac{2}{\Delta \mu_a}\log\left(\frac{g_1(\tau, \rho, F^0, (\mu_a^0 - \Delta\mu_a)/2, \mu_s'^0)}{g_1(\tau, \rho, F^0, (\mu_a^0 + \Delta\mu_a)/2, \mu_s'^0)}\right),$$

-continued $$d_s(\tau, \rho) = \frac{2}{\Delta \mu_s'}\log\left(\frac{g_1(\tau, \rho, F^0, \mu_a^0, (\mu_s'^0 - \Delta\mu_s')/2)}{g_1(\tau, \rho, F^0, \mu_a^0, (\mu_s'^0 + \Delta\mu_s')/2)}\right),$$

where $\Delta F/F^0 = \Delta\mu_a/\mu_a^0 = \Delta\mu_s'/\mu_s'^0 = 10^{-5}$. Equations (11), (12), and (13) are important intermediate results, which provide generalized expressions for the analytical and numerical computation of the multiplicative weighting factors in the DCS Modified Beer-Lambert law for any homogeneous geometry.

One non-limiting assumption in this approach is that the correlation diffusion equation accurately models the electric field auto-correlation function in tissue. This assumption is applicable to using large source-detector separations, $\rho \equiv 1/(\mu_a+\mu_s')$, to measure highly scattering media with isotropic dynamics. The DCS Modified Beer-Lambert law (Eq. (4)), however, can also be used for correlation transport conditions wherein the correlation diffusion equation breaks down. In this case, the derivatives in Eqs. (11) and (12) will have to be applied to the solutions of the so-called correlation transport equation, which can be solved numerically with Monte Carlo techniques.

Appendix 2

The semi-infinite solution to the correlation diffusion equation (Eq. (5)) is approximately exponential in the small delay-time limit, i.e., $g_1(\tau) \approx \exp(-\gamma F\tau)$, with $\gamma \equiv K_0(\mu_s'/\mu_a) k_0^2 r_1$. Normalizing the delay-time by the characteristic decay-time, i.e., $\tau_c = (\gamma F)^{-1}$, is a meaningful dimensionless way to express delay-times (FIGS. 12, 14), e.g., $g_1 \approx 0.4$ for $\tau\gamma F=1$. Further, the DCS Modified Beer-Lambert law (Eq. (4)) is a good approximation in the small delay-time limit because $-\log(g_2(\tau)-1) = -\log(\beta g_1^2) = 2\gamma\tau F - \log(\beta)$ is linear with respect to F.

To derive the small delay-time limit of the semi-infinite correlation diffusion solution, first note that if the source-detector separation, $\rho$, is much greater than the photon transport mean-free path through tissue, $l_{tr}$, then $$r_b \approx r_1(1 + x/r_1^2), \qquad (14)$$

$$\frac{1}{r_b} \approx \frac{1}{r_1}\left(1 - \frac{x}{r_1^2}\right),$$

where $x=2z_b(z_b+l_{tr})$. Substituting Eq. (14) into Eq. (2), we see that $$G_1(\tau) = \frac{3}{4\pi\ell_{tr}}\frac{\exp(-K(\tau)r_1)}{r_1}\left[1 - \exp(-K(\tau)x/r_1)\left(1 - \frac{x}{r_1^2}\right)\right]. \qquad (15)$$

In the limit $K(\tau)x/r_1 \square 1$, which is satisfied at small delay-times, Eq. (15) simplifies further to $$G_1(\tau) = \frac{x\exp(-K(\tau)r_1)}{r_1^2}\left(K(\tau)\frac{1}{r_1}\right). \qquad (16)$$

In the more stringent limit $2(\mu_s'/\mu_a)k_0^2 F\tau \square 1$, the electric field auto-correlation function in Eq. (16) is approximately exponential:

$$g_1(\tau) = \frac{G_1(\tau)}{G_1(0)} \approx \exp(-\gamma F\tau)\left(1 + \frac{\gamma F\tau}{r_1 K_0 + 1}\right) \approx \exp(-\gamma F\tau), \quad (17)$$

where $\gamma = K_0 k_0^2 r_1(\mu'_s/\mu_a)$ and $K_0 \equiv K(0) = [3\mu_a(\mu_a + \mu'_s)]^{1/2}$.

Appendix 3

All animal procedures were in accordance with applicable guidelines. One DCS source-detector pair and one NIRS/DOS source-detector pair were used for hemodynamic monitoring. The positions of these fibers, denoted as (lateral distance from the center of the eye, lateral distance from midline), are (10 mm, 15 mm), (21 mm, 5 mm), (26 mm, 5 mm), and (37 mm, 15 mm) for the DCS source, DCS detector, NIRS/DOS source, and NIRS/DOS detector, respectively. Thus, the source-detector separations for both the NIRS/DOS and DCS pairs are approximately 15 mm.

Upon completion of the surgical preparation, the ventilation of the pig was switched to a mixture of oxygen and nitrogen (3:7) with no isoflurane. Anesthesia was maintained instead with intravenous administration of ketamine (60 mg/kg/h). Throughout the rest of the study, arterial oxygen saturation and end-tidal $CO_2$ were continually monitored with blood gas samples from the femoral artery and with a capnograph, respectively. The ventilation rate was initially adjusted to maintain an end-tidal $CO_2$ between 40 and 50 mm Hg.

After inserting ninety-degree bend terminated optical fibers (Fiberoptic Systems, Simi Valley, Calif.) in the burr holes, a 5-pound sandbag weight was carefully placed on top of the fibers to secure them in place. Two 1-mm diameter multi-mode borosilicate fibers (Fiberoptic Systems) delivered source light to the cerebral tissue, and a third 1-mm diameter multi-mode fiber received diffusing light from the tissue for NIRS/DOS detection. For DCS detection, a 4×1 bundle of 780HP single-mode fibers (Fiberoptic Systems) was used. These fibers interfaced to a portable custom-built instrument designed for hemodynamic monitoring. In the DCS measurement, a continuous wave, long coherence length 785 nm laser (CrystaLaser Inc., Reno, Nev.) was employed to deliver source light, and the outputs from an array of 4 high sensitivity avalanche photodiodes (SPCM-AQ4C, Excelitas, Canada) operating in photon counting mode were connected to a multiple $\tau$ hardware correlator (Correlator.com, Bridgewater, N.J.). In the NIRS/DOS measurement, three lasers (690 nm 785 nm, 830 nm; OZ Optics, Canada) intensity modulated at 70 MHz were coupled to an optical switch, which sequentially cycled the source light between the three wavelengths. A heterodyne detection scheme using a photomultiplier tube (R928, Hamamatsu, Bridgewater, N.J.) was employed for NIRS/DOS detection. The data acquisition was interleaved between NIRS/DOS and DCS.

After ten minutes of "baseline" cerebral hemodynamic monitoring in the pig, the drug dinitrophenol (DNP, 9 mg/kg) was injected intravenously over an hour to dramatically increase cerebral blood flow and oxygen metabolism. The oxygen content in the ventilated gas was increased as needed to maintain the arterial oxygen saturation in the pig above 95%.

Probe Pressure Modulation Algorithm for Oxygenation Monitoring with DOS/NIRS

An analogous probe pressure modulation scheme to DCS can be used to calibrate continuous wave DOS/NIRS for monitoring of cerebral oxy-hemoglobin ($HbO_c$) and deoxyhemoglobin ($HbR_c$) concentrations. This scheme employs a two-layer Modified Beer-Lambert framework wherein tissue scattering is constant. It is often a reasonable approximation to assume that scattering effects on optical density changes are negligible when compared against absorption effects.

Following analogous steps to those outlined for flow monitoring, DOS/NIRS measurements of light intensity are made at a long source-detector separation, $I(\rho_l)$, and a short source-detector separation, $I(\rho_s)$. Using a two-layer model of the head, the DOS/NIRS two-layer Modified Beer-Lambert laws are $$\Delta OD^{long} \equiv -\log\left[\frac{I(\rho_l)}{I^0(\rho_l)}\right] = L_c(\rho_l)\Delta\mu_{a,c} + L_{ec}(\rho_l)\Delta\mu_{a,ec} \quad (1.1)$$

$$\Delta OD^{short} \equiv -\log\left[\frac{I(\rho_s)}{I^0(\rho_s)}\right] = L_{ec}(\rho_s)\Delta\mu_{a,ec} \quad (1.2)$$

The cerebral and extra-cerebral tissue absorption and scattering coefficients that give rise to the measured intensities $I(\rho_l)$ and $I(\rho_s)$ are $\mu_{a,c}$, $\mu_{a,ec}$, $\mu'_{s,c}$ and $\mu'_{s,ec}$, respectively. Similarly, at the baseline measured intensities $I^0(\rho_l)$ and $I^0(\rho_s)$, the baseline cerebral and extra-cerebral tissue absorption and scattering coefficients are $\mu_{a,c}^0$, $\mu_{a,ec}^0$, $\mu'^0_{s,c}$, and $\mu'^0_{s,ec}$, respectively. The differential changes of cerebral and extra-cerebral absorption from baseline are $\Delta\mu_{a,c} \equiv \mu_{a,c} - \mu_{a,c}^0$ and $\Delta\mu_{a,ec} \equiv \mu_{a,ec} - \mu_{a,ec}^0$. Finally, the partial pathlengths $L_c(\rho_l) \equiv \partial OD^{long,0}/\partial\mu_{a,c}$, $L_{ec}(\rho_l) \equiv \partial OD^{long,0}/\partial\mu_{a,ec}$, and $L_{ec}(\rho s) \equiv \partial OD^{short,0}/\partial\mu_{a,ec}$ are the mean pathlengths that the detected light travels through the cerebral (c) and extra-cerebral (ec) layers. It is assumed that detected light from the short separation does not sample the brain, and consequentially, $L_c(\rho_s) = 0$ and $L_{ec}(\rho_s)$ is approximately the semi-infinite differential pathlength.

Solving Eqs. (1.1) and (1.2) and for $\Delta\mu_{a,c}$, one may obtain $$\Delta\mu_{a,c} = \frac{1}{L_c(\rho_l)}\left[\Delta OD^{long} - \frac{L_{ec}(\rho_l)}{L_{ec}(\rho_s)}\Delta OD^{short}\right]. \quad (1.3)$$

The key advantage of using probe pressure modulation with DOS/NIRS is that it enables direct measurement of the ratio $L_{ec}(\rho_l)/L_{ec}(\rho_s)$.

The ratio $L_{ec}(\rho_l)/L_{ec}(\rho_s)$ can be directly measured from differential short and long separation optical density changes between perturbed and baseline states wherein only the extra-cerebral absorption is different. Probe pressure modulation is a simple way to induce controlled extra-cerebral absorption changes without affecting cerebral absorption. For relating a perturbed state at probe pressure P to the baseline state at probe pressure $P^0$, Eqs. (1.1) and (1.2) simplify to $$\Delta OD^{long,P} \equiv -\log\left[\frac{I^P(\rho_l)}{I^0(\rho_l)}\right] = L_{ec}(\rho_l)\Delta\mu_{a,ec}^P, \quad (1.4)$$

$$\Delta OD^{short,P} \equiv -\log\left[\frac{I^P(\rho_s)}{I^0(\rho_s)}\right] = L_{ec}(\rho_s)\Delta\mu_{a,ec}^P, \quad (1.5)$$

where $I^P(\rho_l)$ and $I^P(\rho_s)$ are the measured intensities at probe pressure P, and $\Delta\mu_{a,ec}^P \equiv \mu_{a,ec}^P - \mu_{a,ec}^0$ is the pressure-induced extra-cerebral absorption change.

Dividing by and then substituting the result into (1.3), we obtain $$\Delta \mu_{a,c} = \frac{1}{L_c(\rho_l)}\left[\Delta OD^{long} - \frac{\Delta OD^{long,P}}{\Delta OD^{short,P}}\Delta OD^{short}\right]. \quad (1.6)$$

Here, intensity measurements at long and short separations along with initial calibration measurements at two probe pressures determines $\Delta \mu_{a,c}$ within a multiplicative proportionality constant, $1/L_c(\rho_l)$. For accurately estimating the magnitude of the cerebral absorption change, $L_c(\rho_l)$ is calculated by numerically computing the derivative of the continuous wave two-layer photon diffusion Green's function, $\Phi(\rho_l)$, evaluated at the baseline tissue optical properties:

$$L_c(\rho_l) = -\frac{\partial}{\partial \mu_{a,c}}(-\log(\Phi(\rho_l))) \quad (1.7)$$

$$\approx \frac{1}{\Delta \mu_{a,c}} \log\left[\frac{\Phi(\rho_l, \mu_{a,c}^0 - \Delta \mu_{a,c}/2, \mu_{a,ec}^0, \mu_{s,c}'^0, \mu_{s,ec}'^0, l)}{\Phi(\rho_l, \mu_{a,c}^0 - \Delta \mu_{a,c}/2, \mu_{a,ec}^0, \mu_{s,c}'^0, \mu_{s,ec}'^0, l)}\right],$$

where $\Delta \mu_{a,c}/\mu_{a,c}^0 = 10^{-5}$. The Green's function $\Phi(\rho_l)$ can be evaluated using the analytical two-layer solution, or it can also be evaluated numerically using Monte Carlo techniques. The computation of $L_c(\rho_l)$ requires knowledge of $\mu_{a,c}^0$, $\mu_{a,ec}^0$, $\mu_{s,c}'^0$, $\mu_{s,ec}'^0$, and l. Ideally the extra-cerebral layer thickness is known a priori from anatomical information, and the tissue baseline optical properties are measured (e.g., with time-domain techniques). If a priori anatomical information and instrumentation for measuring baseline optical properties is not available, then the baseline optical properties need to be assumed. The extra-cerebral layer thickness can either also be assumed or estimated from the two-layer fit of DCS data at multiple probe pressures from the DCS pressure algorithm.

Cerebral absorption determined from (1.6) will not be affected by extra-cerebral absorption changes to the extent that the two-layer model accurately models the head.

Figure 31:
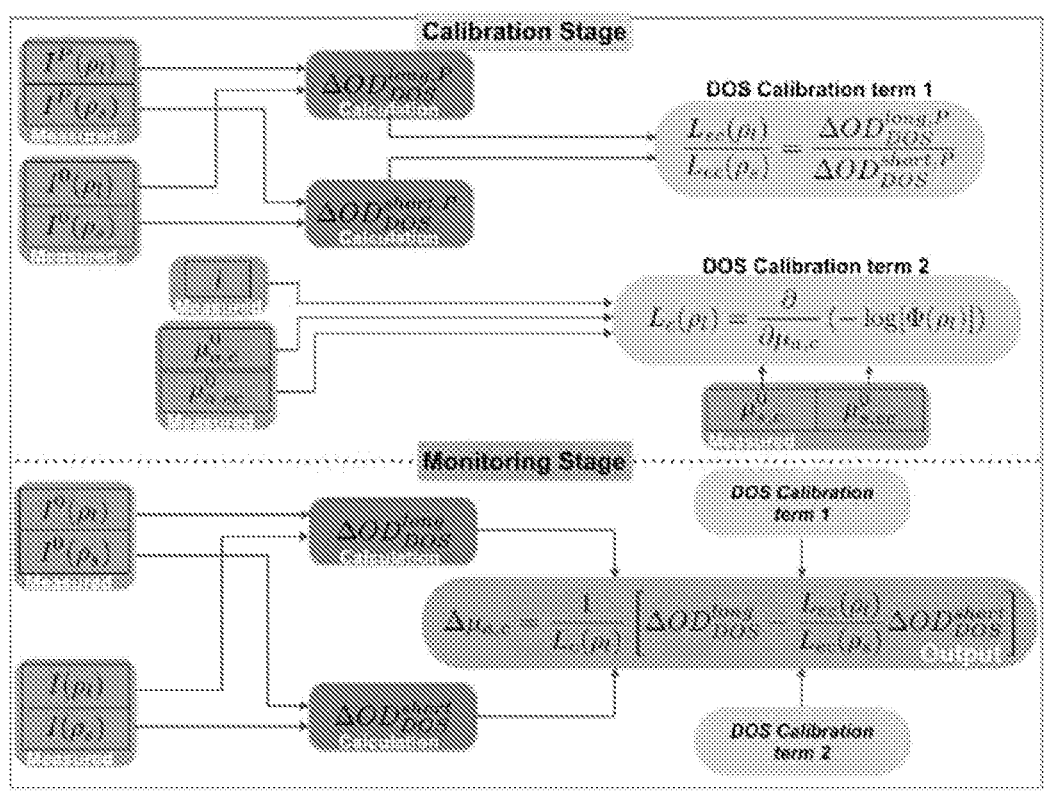
FIG. 31 is a flow chart of a probe pressure modulation algorithm for cerebral tissue absorption monitoring ($\Delta\mu_{a,c}$) with DOS/NIRS. In the calibration stage, baseline long and short separation intensities measured at probe pressure $P^0$ ($I^0(\rho_l)$, $I^0(\rho_s)$) and at probe pressure $P \neq P^0$ ($I^P(\rho_l)$, $I^P(\rho_s)$) are used to calculate $\Delta OD^{long,P}$ and $\Delta OD^{short,P}$, which are then used to estimate $L_{ec}(\rho_l)/L_{ec}(\rho_s)$ ("DOS Calibration term 1). "DOS Calibration term 2" is the numerical evaluation of $L_c(\rho_l)$, which requires knowledge of the baseline tissue optical properties and the extra-cerebral layer thickness (l). Ideally, these baseline tissue properties are measured. In the monitoring stage, DOS Calibration terms 1 and 2 are employed to convert subsequent measurements of differential long and short separation optical density changes, i.e., $\Delta OD^{long}$ and $\Delta OD^{short}$, to differential cerebral absorption changes via. Note that the baseline used for the calibration stage and for the monitoring stage is the same.

FIG. 31 is a flow chart summarizing the probe pressure modulation algorithm for cerebral tissue absorption monitoring ($\Delta \mu_{a,c}$) with DOS/NIRS. As shown in that figure, in the calibration stage, baseline long and short separation intensities measured at probe pressure $P^0$ ($I^0(\rho_l)$, $I^0(\rho_s)$) and at probe pressure $P \neq P^0$ ($I^P(\rho_l)$, $I^P(\rho_s)$) are used to calculate $\Delta OD^{long,P}$ and $\Delta OD^{short,P}$, which are then used to estimate $L_{ec}(\rho_1)/L_{ec}(\rho_s)$ ("DOS Calibration term 1"). "DOS Calibration term 2" is the numerical evaluation of $L_c(\rho_l)$, which requires knowledge of the baseline tissue optical properties and the extra-cerebral layer thickness (l). Ideally, these baseline tissue properties are measured. In the monitoring stage, DOS Calibration terms 1 and 2 are employed to convert subsequent measurements of differential long and short separation optical density changes, i.e., $\Delta OD^{long}$ and $\Delta OD^{short}$, to differential cerebral absorption changes. Note that the baseline used for the calibration stage and for the monitoring stage is the same.

The cerebral tissue absorption coefficient depends linearly on the concentrations of tissue chromophores. With NIR light, changes in cerebral absorption predominantly arise from changes in cerebral oxygenated hemoglobin ($HbO_c$) and de-oxygenated hemoglobin ($HbR_c$) concentrations, such that $$\Delta \mu_{a,c}(\rho_l, \lambda) \approx \varepsilon_{HbO}(\lambda)\Delta HbO_c + \varepsilon_{HbR}(\lambda)\Delta HbR_c. \quad (1.8)$$

Here, $\varepsilon_{HbO}(\lambda)$ and $\varepsilon_{HbR}(\lambda)$ and are wavelength-dependent extinction coefficients for oxygenated hemoglobin and de-oxygenated hemoglobin, which are both known and tabulated as a function of wavelength $\lambda$, and $\Delta HbO_c$ and $\Delta HbR_c$ are differential changes in cerebral oxygenated and de-oxygenated hemoglobin concentration from baseline. For multispectral cerebral absorption monitoring with (1.6) and (1.8) becomes a system of equations, i.e., one equation for each wavelength, which can then be solved for $\Delta HbO_c$ and $\Delta HbR_c$. A minimum of two wavelengths is required to solve for these two chromophores.

Finally, the baseline cerebral hemoglobin concentrations $HbO_c^0$ and $HbR_c^0$ can be calculated from multispectral measurements of $\mu_{a,c}^0(\lambda)$, which in turn enables the computation of cerebral tissue oxygen saturation, $StO_{2,c}$:

$$StO_{2,c} = \frac{HbO_c^0 + \Delta HbO_c}{HbO_c^0 + HbR_c^0 + \Delta HbO_c + \Delta HbR_c}.$$

Combining DOS/NIRS measurements of $StO_2$, with DCS measurements of cerebral blood flow ($F_c$) permits monitoring of cerebral oxygen metabolism. Any of the systems and/or components described herein may be configured to apply any aspect of the foregoing DCS, DOS, and NIRS analysis, e.g., the foregoing analysis of $StO_2$ and $F_c$.

Additional Aspects and Embodiments

In one aspect, the present disclosure provides methods. The methods suitably include measuring moving particles in a tissue. Such particles include red blood cells, white blood cells, leukocytes, lymphocytes, muscle fibers, and the like. Additionally, the methods are suitable for measuring exogenous moving particles, such as scattering contrast agents (e.g., ultrasound 'microbubbles'). The disclosed methods are applicable to motion of any particle of living tissue; red blood cells are considered especially suitable.

Measuring suitably includes illuminating a first tissue region through illumination of a second tissue region that is superficial to the first tissue region. The first tissue region may be a blood vessel, a muscle, a bone, and the like. Cerebral tissue is a particularly suitable first tissue region. As one example, a first tissue region may be cerebral tissue, and a second tissue region may be extracerebral tissue, e.g., scalp, skull, cerebro-spinal fluid located proximate to the cerebral tissue.

Illumination may be effected with a first source-detector pair and with a second source-detector pair. The sources suitably provide the illumination, and the detectors collect illumination scattered by the particles. Suitable illumination sources are long-coherence length lasers for DCS, and multi-mode lasers, LEDs, arc lamps, halogen lamps for DOS, lasers and LEDs being most suitable. Suitable detectors include photon counters, imagers, photodiodes, photomultiplier tubes and the like; photon counting avalanches photo diodes (APDs) are considered particularly suitable for DCS. Source-detector pairs may be maintained in position by being secured by elastic, a Velcro™ band, a balloon, a strap, a garment, or by other securing means known to those of ordinary skill in the art. The distance between sources and detectors may be fixed, but may also be variable. In some embodiments, the user may change the distance between the sources and detectors. It should be understood that in some embodiments, a single detector may collect illumination from one, two, or more sources. Two or more of such sources may be separated from their common detector by different distances. Similarly, a single source can supply illumination (concurrently) to one or more detectors, with different distances separating the common source from each detector.

The source and detector of the first source-detector pair are suitably separated by a first distance. Such a distance may be in the range of from 0.1 rum to about 1 mm, or from about 1 mm to about 10 cm, or from about 10 mm to about 0.5 cm. The source and detector of the second source-detector pair are also suitably separated by a distance. The separation of the source and detector of the second pair is suitably greater than the separation distance between the source and detector of the first pair. The separation of the source and detector of the second pair is may be 1.0001 times, 1.1 times, 1.5 times, 2 times, 5 times, 10 times, 100 times, 1000 times, or even 10,000 times the separation distance between the source and detector of the first pair.

Collection of the illumination is suitably performed under application of (a) one or more perturbations directed to the second tissue region (superficial region), (b) one or more perturbations proximate to the location of the first source-detector pair, proximate to the second source source-detector pair, or proximate to both the first and second source-detector pairs, or (c) any combination of (a) and (b). It should be understood that exposure to ambient conditions is considered a perturbation for purposes of this disclosure.

As an example, a user might collect illumination from the first and second detectors while the tissue is subjected to ambient pressure and then collect illumination from the first and second detectors while the tissue is subjected to a pressure that is 10 mm Hg greater than ambient pressure. Exemplary, non-limiting perturbations include pressure variation (positive and negative), thermal energy transfer (e.g., application or removal of heat), illumination, fluid, electric field, electric current, chemical treatment, sonication, magnetic stimulation, and the like. In some embodiments, illumination is collected under two or more conditions, two or more of which conditions differ in some aspect from ambient conditions. In other embodiments, illumination is collected under ambient conditions and under one other condition that differs in some aspect (e.g., pressure, temperature, humidity) from ambient conditions. The form of the pertubations can encompass a step change (e.g. ambient pressure to 10 mmHg greater than ambient pressure, and back to ambient pressure), or a modulation (e.g. pressure varying sinusoidally between ambient and 10 mmHg greater than ambient) of conditions.

A perturbation may be applied, in some embodiments, so as to effect a hemodynamic change in the second tissue region. Such a change may be a change in blood flow. As one example, pressure may be applied to a subject's extracerebral region so as to reduce extracerebral blood flow in and/or around the location of the applied pressure.

Users may estimate a blood flow of the first tissue region from the collected illumination. In one embodiment, this estimation may include application of the DCS Modified Beer-Lambert law, which is described elsewhere herein. In some embodiments, estimating blood flow may comprise application of the DCS Modified Beer-Lambert law for a multi-layer medium, e.g., a two-layer medium, a three-layer medium, or other multi-layer medium. As described elsewhere herein, application of the DCS Modified Beer-Lambert law for a two-layer medium is considered particularly suitable for some applications, including estimation of cerebral blood flow. In that particular application, extracerebral tissue is modeled as one layer, and cerebral tissue is modeled as another layer in the two-layer model.

In some embodiments, at least one of the parameters of the DCS Modified Beer-Lambert law is derived from illumination collected from a subject. In this way, the user may develop a model that is customized to a particular subject. In some embodiments, at least one of the parameters of the DCS Modified Beer-Lambert law is derived from population measurements. A population measurement may be a value based on two or more subjects, e.g., an average value based on a measurement of seven subjects. One may apply in the model one or more parameters derived from the subject under observation as well as one or more parameters derived from population measurements.

Deriving a parameter may include, e.g., calculating a value related to illumination gathered when tissue is subject to ambient conditions or subject to a perturbation such as pressure, a cold bar, and the like. The illumination may—as described elsewhere herein—be gathered from the first source-detector pair, from the second detector pair, or both.

One or more steps of the disclosed methods (including the estimation of blood flow) may be based on illumination collected at a number of delay time values, e.g., 1, 2, 3, 4, 5, or more delay time values. In some embodiments, the number of delay time values used is optimized to be the minimum number of delay time values to provide a sufficient or desired signal-to-noise ratio and sufficient measurement speed. In some embodiments, the one or more steps are based on illumination collected at one delay time value. In some embodiments, there are 1-5 delay times, ranging between, e.g., 0.1 and 1000 microseconds.

A user may estimate the first tissue region blood flow from the collected illumination before, during, and/or after delivery of an agent to the subject. An agent may be a contrast agent, a treatment agent, an agonist, and the like. Contrast agents include, e.g., indocyanine green (ICG, Cardio-Green, Akron Inc.), microbubbles utilized for ultrasound contrast, or boli/infusions of red blood cells. A user may estimate the first tissue region blood flow before, during, and/or after the subject engages in an activity, e.g., exercise, sleep, eating, treatment, and the like. A user may also estimate the blood flow during a procedure, e.g., surgery, stimulation, or other treatment. This estimation may be done in real time. The estimation may also be done after the treatment.

A user may also estimate the first tissue region blood flow before, during, and/or after physically manipulating the subject, or before, during and/or after any combination of the foregoing. As described elsewhere herein, the user may estimate the first tissue region blood flow from the collected illumination collected at a number of delay time values, including at a number optimized to be the minimum number of delay time values to provide a sufficient signal-to-noise ratio. A user may also perform the estimation based on illumination collected at one delay time value.

The present disclosure also provides systems. In one embodiment, a system comprises a first illumination source-detector pair having a source and detector separated by a first distance (a); a second illumination source-detector pair having a source and detector separated by a second distance (b), distances (a) and (b) being different from one another; an element configured to apply a pressure between the system and the subject's body; and a processor configured to estimate a tissue's blood flow from a signal related to illumination collected by at least one of the source-detector pairs.

Suitable sources, detectors, source-detector pairs, and source-detector separations are described elsewhere herein.

Balloons, pumps, servos, elastic bands, and other devices known to those of skill in the art are all suitable elements for applying a pressure between the system and the subject's body. It should be understood, however, that the disclosed systems may also include one or more elements configured to apply a perturbation other than pressure to the subject. As one example, a system may include a heater, a cooler, an injector, a source of vacuum, and like elements configured to deliver one or more perturbations to the subject. An element may be configured to apply a perturbation (e.g., pressure, heat) proximate to at least one of the first and second source-detector pairs. As described elsewhere herein, a system may include an accelerometer, which may be used to measure and account for the effect of a subject's motion or an instrument's motion. A pressure may be greater than ambient conditions (e.g, from 0.001 atm to 10 atm above ambient conditions). A pressure may also be less than ambient conditions (e.g., from 99.995% of atmospheric pressure to 50% of atmospheric pressure).

The disclosed systems may further comprise a device configured to compute intensity correlation functions from photon counts. Such a device may be in electronic communication, optical communication, or both with at least one of the detectors of the first and second source-detector pairs. Suitable such devices include computers (stationary and portable), smartphones, tablet computers, microcontrollers and processors, field programmable gate arrays, electronic circuits and the like.

The systems may include one or more elements—e.g., a computer, a tablet, or even a processor—configured to isolate blood flow signals from collected illumination. The processor may be configured to carry out one or more steps of the DCS Modified Beer-Lambert law, for example.

A system may include one or more detectors that are single-mode fibers or few-mode fibers. As described elsewhere herein, a detector of the system may be a photon-counting detector. In some embodiments, at least one source and one detector share a prism. In some embodiments at least two sources share a prism. In some embodiments at least two detectors share a prism, e.g., single mode fibers for DCS and multimode fibers for DOS.

A user may use the described systems to measure a motion of moving particles in a subject's tissue. One such motion is cerebral blood flow.

Further aspects are provided below.

Aspect 1: A system, comprising a first illumination source-detector pair having a source and detector separated by a first distance (a); a second illumination source-detector pair having a source and detector separated by a second distance (b), distances (a) and (b) being different from one another; an element configured to apply a pressure between the device and the subject's body; a processor configured to estimate a tissue blood flow, blood volume, saturation, or any combination thereof, from a signal related to illumination collected by at least one of the source-detector pairs.

Aspect 2. The system according to aspect 1, further comprising a device configured to compute intensity correlation functions from photon counts, the device being in electronic communication, optical communication, or both with at least one of the detectors of the first and second source-detector pairs.

Aspect 3. The system according to any of aspects 1-2, further comprising an element (e.g., a processor, a sensor, and the like) configured to isolate a hemodynamic signal from collected illumination. Such a signal may relate to blood flow, blood volume, saturation, or any combination thereof. The signal may be from DCS measurements, DOS measurements, or both.

Aspect 4. The system according to of any of aspects 1-3, further comprising an element configured to apply a perturbation to the subject.

Aspect 5. The system of aspect 4, wherein the element is configured to apply a pressure proximate to at least one of the first and second source-detector pairs.

Aspect 6. The system according to any of aspects 4-5, wherein the element comprises a balloon, a spring, a motor, a hydraulic element, or any combination thereof.

Aspect 7. The system of aspect 6, wherein the element comprises a balloon.

Aspect 8. The system of aspect 4, wherein the element is automated. The system may be configured such that a user sets a pressure (or other perturbation) that the element then applies to the subject. The user may set a perturbation profile (e.g., constant perturbation, alternating perturbations) for the element to apply.

Aspect 9. The system of any of aspects 1-8, wherein at least one detector is a single-mode, two mode, or few-mode fiber (e.g., a fiber having from 3 to 10 modes).

Aspect 10. The system of any of aspects 1-9, wherein at least one detector comprises a photon-counting detector.

Aspect 11. The system of any of aspects 1-10, wherein at least one source and one detector share a prism. The source and detector may both physically contact the prism. The source and detector may also be in optical communication with the prism.

Aspect 12. The system of any of aspects 1-11, wherein at least two sources share a prism. In any of the foregoing aspects (i.e., aspects 1-11), at least one DCS detector and at least one DOS detector may share a prism. Thus, detectors for DOS and DCS may be in connection with or even reside on the same prism. Such devices may include multi-mode (including few-mode) and single-mode fibers.

Aspect 13. The system of any of aspects 1-12, the system further comprising an element configured to maintain at least one source-detector pair in a position on a subject. As described elsewhere herein, the element may be a band, a cap, a sleeve, or other element that secures onto a subject. A cap or band—such as a headband—is considered especially suitable. The system may include a hat or cap to maintain the position of one or more system components on a user, which hat or cap may be adjustable.

Aspect 14. The system of aspect 13, wherein the element comprises a band, a cap, a sleeve, or any combination thereof.

Aspect 15. The system of any of aspects 1-14, wherein at least one source is configured to deliver illumination at between about 300 nm and 1500 nm in wavelength.

Aspect 16. The system of aspect 15, wherein the at least one source is configured to deliver illumination at between about 660 nm and about 930 nm in wavelength.

Aspect 17. The system of any of aspect 1-16, wherein the system further comprises a fiber optic connection to a source, a detector, or both.

Aspect 18. The system of aspect 1, wherein the processor is configured to apply a DCS Modified Beer Lambert Law. a DOS/NIRS Modified Beer Lambert Law, or any combination thereof to the signal related to illumination collected by at least one of the source-detector pairs. The Modified Beer Lambert Law is described elsewhere herein. A system may also include an amount of optical coupling gel. Such gel may be dispensed by the system. The gel may be used to place a portion of the system into optical communication with a subject, or even to enhance the system's optical communication with the subject. The system may include a gel dispenser. During (or even before) operation, one or more system components may be in physical or optical contact with the optical coupling gel.

It should also be understood that systems according to any of the preceding aspects may be configured to collect DCS information, DOS/NIRS information, or both. A system may include a processor that is configured to collect and/or process either type of information. A system may be dedicated to DCS or DOS/NIRS, or may be switchable between the two, or may even operate in DCS and DOS modes simultaneously.

Aspect 19. A component, comprising: an illumination source and an illumination detector, the source and detector being secured to an element configured to maintain at least one source-detector pair in a position on a subject; and a fiber optic in optical communication with at least one of the source and detector. Suitable sources and detectors are described elsewhere herein. A component may be configured such that the source and detector are maintained at a constant separation. The component may be configured such that the user may set the location of one or both of the source and detector. As one example, the component may include multiple anchor points (e.g., snaps, velcro, hooks) at which a user may fasten the source and/or detector. A component may also be configured such that the locations of the source and detector may not be modified. As described elsewhere herein, the component may be configured for DCS, DOS, or both measurements.

Aspect 20. The component of aspect 19, further comprising an element configured to apply a perturbation to the subject. As described elsewhere herein, the element may be configured to deliver a pressure; other perturbations include heat, cold, agents, and the like.

Aspect 21. The component of aspect 20, wherein the element is configured to apply a pressure proximate (e.g., within about 20 cm or less, 10 cm or less, or even within about 5 cm or less) to at least one of the source and detector.

Aspect 22. The component of aspect 21, wherein the source is configured to deliver illumination at between about 300 nm and 1500 nm in wavelength.

Aspect 23. The component of any of aspects 19-22, further comprising a processor configured to apply a DCS Modified Beer Lambert Law, a DOS/NIRS Modified Beer-Lambert law, any combination thereof to the signal related to illumination collected by at least one of the source-detector pairs.

Aspect 24. The component of any of aspects 19-24, wherein the component is configured to collect one or more of DCS or DOS information.

The present disclosure also provides methods of estimating a hemodynamic quantity (e.g., a cerebral blood flow), as well as systems configured to perform these methods. These methods may include formulating a first estimate of extracerebral blood flow. This estimate may include DCS measurement, as described elsewhere herein.

The methods also include perturbing extracerebral tissue. Suitable perturbations—e.g., pressure application—are described elsewhere herein. A user may apply one, two, or more perturbations during the course of a blood flow estimation.

A user may also formulate a second estimate of extracerebral blood. The second estimate may be related to perturbation of extracerebral tissue, as described elsewhere herein.

The methods may also include formulating a final estimate of cerebral blood flow related at least in part to the first and second estimates of extracerebral blood flow. The first estimate of extracerebral blood flow may be obtained under ambient conditions, but may also be related to perturbation of extracerebral tissue. Thus, both estimates of extracerebral blood flow may be related to perturbations of the extracerebral tissue.

The methods may also include formulating at least a first estimate of cerebral blood flow. This estimate may be based on DCS results, DOS results, or any combination thereof. A user may also relate the final cerebral blood flow estimate at least in part to an estimate of extracerebral blood flow and to the first estimate of cerebral blood flow.

In a further aspect, the present disclosure provides methods of monitoring a blood flow. These methods include illuminating a tissue and a region superficial to the tissue. Suitable illumination techniques and illuminators are set forth elsewhere herein. A user may also apply and/or modulate one or more perturbations (e.g., pressures, administration of agents, environmental changes such as heat, cold, light, and darkness) that affect or otherwise applied to the region superficial to the tissue. A user may also collect a blood flow signal that is related to illumination reflected by the tissue and to illumination reflected by the region superficial to the tissue. A user may also remove from that signal at least a portion of the illumination reflected by the region superficial to the tissue. This may also be characterized as removing from that signal the contribution to that signal from the illumination reflected by the region superficial to the tissue.

What is claimed:

1. A system, comprising:
  a first device that comprises
    a first illumination source-detector pair having a source and a detector separated by a first distance (a);
    a second illumination source-detector pair having a source and a detector separated by a second distance (b),
  distances (a) and (b) being different from one another such that the first illumination source-detector pair is configured to illuminate and detect scattered light from a deep tissue region of a tissue and the second illumination source-detector pair is configured to illuminate and detect scattered light from superficial tissue region disposed between the deep tissue region and the first illumination source-detector pair and the second illumination source-detector pair;
  a first element configured to apply a varying perturbation to the surface of the tissue such that the deep tissue region is substantially unaffected; and
  a processor configured to estimate at least one of regional blood flow, blood volume, and regional saturation in the deep tissue region from (i) signals related to scattered light collected by at least the first illumination source-detector pair and the second illumination source-detector pair during application of a first pressure to the tissue surface, and (ii) signals related to scattered light collected by the first illumination source-detector pair and the second illumination source-detector pair during application of a second pressure to the tissue surface.

2. The system of claim 1, further comprising a second device configured to compute intensity correlation functions from photon counts, the second device being in electronic communication, optical communication, or both with at least one of the detectors of the source-detector pairs.

3. The system of claim 1, further comprising a second element configured to isolate a hemodynamic superficial tissue signal from collected illumination.

4. The system of claim 1, wherein the first element is configured to apply a pressure proximate to at least one of the source-detector pairs.

5. The system of claim 4, wherein the first element comprises a balloon, a spring, a motor, a hydraulic element, or any combination thereof.

6. The system of claim 5, wherein the first element comprises a balloon.

7. The system of claim 1, wherein the first element is automated.

8. The system of claim 1, wherein at least one detector of the first source-detector pair and the second source-detector pair is a single-mode or few-mode fiber.

9. The system of claim 1, wherein at least one detector of the first source-detector pair and the second source-detector pair comprises a photon-counting detector.

10. The system of claim 1, wherein at least one source of the first source-detector pair and the second source-detector pair and one detector of the first source-detector pair and the second source-detector pair share a prism.

11. The system of claim 1, wherein the source of the first source-detector pair and the source of the second source-detector pair share a prism.

12. The system of claim 1, wherein at least one detector of the first source-detector pair and the second source-detector pair is a Diffuse Optical Spectroscopy (DOS) detector and at least one detector of the first source-detector pair and the second source-detector pair is a Diffuse Correlation Spectroscopy (DCS) detector, and wherein the at least one DOS detector and the at least one DCS detector share a prism.

13. The system of claim 1, the system further comprising a third element configured to maintain at least one source-detector pair in a position on a subject.

14. The system of claim 13, wherein the third element comprises a band, a cap, a sleeve, or any combination thereof.

15. The system of claim 1, wherein at least one source of the first source-detector pair and the second source-detector pair is configured to deliver illumination at between about 300 nm and 1500 nm in wavelength.

16. The system of claim 14, wherein the at least one source of the first source-detector pair and the second source-detector pair is configured to deliver illumination at between about 660 nm and about 930 nm in wavelength.

17. The system of claim 1, wherein the system further comprises a fiber optic connection to a source of the first source-detector pair and the second source-detector pair, a detector of the first source-detector pair and the second source-detector pair, or both.

18. The system of claim 1, wherein the processor is configured to apply a DCS Lambert Law, a DOS/Near Infrared Spectroscopy (NIRS) Modified Beer-Lambert law, any combination thereof to the signal related to illumination collected by at least one of the source-detector pairs.

19. The system of claim 1, further comprising an amount of scattering optical coupling gel configured to be placed between the optical elements and the tissue surface to minimize light reflected from the diffuse-non-diffuse boundary.

20. The system of claim 1, further comprising a pressure sensor configured to monitor a pressure exerted by the first device against a subject.

21. The system of claim 1, wherein the processor is configured to estimate a tissue blood flow from (i) a first signal related to illumination collected by at least one of the source-detector pairs during application of a first pressure to a subject's body, and (ii) a second signal related to illumination collected by at least one of the source-detector pairs during application of a second pressure to a subject's body.

22. The system of claim 1, wherein the first element is configured to moveably advance a portion of the first element so as to increase a pressure between the first device and a subject's body.

* * * * *